(12) United States Patent
Fujii

(10) Patent No.: US 10,451,968 B2
(45) Date of Patent: Oct. 22, 2019

(54) RESIST COMPOSITION AND METHOD OF FORMING RESIST PATTERN

(71) Applicant: TOKYO OHKA KOGYO CO., LTD., Kawasaki-shi (JP)

(72) Inventor: Tatsuya Fujii, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 121 days.

(21) Appl. No.: 15/697,115

(22) Filed: Sep. 6, 2017

(65) Prior Publication Data

US 2018/0072651 A1    Mar. 15, 2018

(30) Foreign Application Priority Data

Sep. 15, 2016 (JP) ................. 2016-181007

(51) Int. Cl.
| | |
|---|---|
| G03F 7/004 | (2006.01) |
| H01L 21/027 | (2006.01) |
| G03F 7/26 | (2006.01) |
| G03F 7/20 | (2006.01) |
| C08F 220/26 | (2006.01) |
| C07C 69/54 | (2006.01) |
| C07D 307/93 | (2006.01) |
| C07D 309/12 | (2006.01) |
| C08F 12/24 | (2006.01) |
| C08F 220/18 | (2006.01) |
| C08F 220/30 | (2006.01) |
| G03F 7/039 | (2006.01) |
| G03F 7/32 | (2006.01) |
| C08F 220/28 | (2006.01) |
| C08F 212/14 | (2006.01) |

(52) U.S. Cl.
CPC ............ *G03F 7/0045* (2013.01); *C07C 69/54* (2013.01); *C07D 307/93* (2013.01); *C07D 309/12* (2013.01); *C08F 12/24* (2013.01); *C08F 220/18* (2013.01); *C08F 220/26* (2013.01); *C08F 220/28* (2013.01); *C08F 220/30* (2013.01); *G03F 7/0046* (2013.01); *G03F 7/0397* (2013.01); *G03F 7/2037* (2013.01); *G03F 7/2041* (2013.01); *G03F 7/26* (2013.01); *G03F 7/322* (2013.01); *H01L 21/0274* (2013.01); *C08F 212/14* (2013.01)

(58) Field of Classification Search
CPC ... G03F 7/004; G03F 7/11; G03F 7/26; G03F 7/2041; G03F 7/2037; C08F 12/24; C08F 212/14; C08F 220/18; C08F 220/28; C08F 220/30; C08F 220/26; H01L 21/0274

USPC ................. 430/270.1, 271.1, 273.1
See application file for complete search history.

(56) References Cited

U.S. PATENT DOCUMENTS

| | | | | |
|---|---|---|---|---|
| 8,617,794 | B2* | 12/2013 | Tsubaki ................ | G03F 7/0392 430/270.1 |
| 9,128,376 | B2* | 9/2015 | Kato ..................... | G03F 7/0392 |
| 9,502,231 | B2* | 11/2016 | Liu ...................... | H01L 21/0212 |
| 9,523,912 | B2* | 12/2016 | Kataoka ................. | G03F 7/038 |
| 9,551,931 | B2* | 1/2017 | Ito .......................... | G03F 7/038 |
| 2007/0178405 | A1* | 8/2007 | Kanda .................. | G03F 7/0045 430/270.1 |
| 2010/0183977 | A1* | 7/2010 | Wang ..................... | C08L 33/16 430/270.1 |
| 2011/0294069 | A1* | 12/2011 | Bae ....................... | G03F 7/0392 430/283.1 |
| 2012/0258402 | A1 | 10/2012 | Sato et al. | |
| 2014/0032102 | A1* | 1/2014 | Egoshi ................ | G01C 21/3469 701/454 |
| 2015/0378257 | A1* | 12/2015 | Yamaguchi ............. | C08L 33/16 430/17 |

FOREIGN PATENT DOCUMENTS

| | | |
|---|---|---|
| JP | A-2009-114381 | 5/2009 |
| JP | A-2012-220800 | 11/2012 |
| WO | WO 2010/095698 A1 | 8/2010 |
| WO | WO 2013/042694 A1 | 3/2013 |

* cited by examiner

*Primary Examiner* — Amanda C. Walke
(74) *Attorney, Agent, or Firm* — Knobbe, Martens, Olson & Bear LLP

(57) ABSTRACT

A resist composition which generates acid upon exposure and exhibits changed solubility in a developing solution under action of acid, and which includes a base component (A) which exhibits changed solubility in a developing solution under action of acid and a fluorine additive component (F) which exhibits decomposability to an alkali developing solution, the fluorine additive component (F) including a fluorine resin component (F1) having a structural unit (f1) containing a base dissociable group and a structural unit (f2) containing a group represented by general formula (f2-r-1) shown below in which each $Rf^{21}$ independently represents a hydrogen atom, an alkyl group, an alkoxy group, a hydroxy group, a hydroxyalkyl group or a cyano group; $n''$ represents an integer of 0 to 2; and * represents a valence bond.

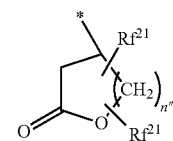

(f2-r-1)

17 Claims, No Drawings

RESIST COMPOSITION AND METHOD OF FORMING RESIST PATTERN

TECHNICAL FIELD

The present invention relates to a resist composition and a method of forming a resist pattern.

This application claims priority to Japanese Patent Application No. 2016-181007, filed Sep. 15, 2016, the entire content of which is incorporated herein by reference.

DESCRIPTION OF RELATED ART

In lithography techniques, for example, a resist film composed of a resist material is formed on a substrate, and the resist film is subjected to selective exposure, followed by development, thereby forming a resist pattern having a predetermined shape on the resist film. A resist material in which the exposed portions of the resist film become soluble in a developing solution is called a positive-type, and a resist material in which the exposed portions of the resist film become insoluble in a developing solution is called a negative-type.

In recent years, in the production of semiconductor elements and liquid crystal display elements, advances in lithography techniques have led to rapid progress in the field of pattern miniaturization. Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are used in mass production. Furthermore, research is also being conducted into lithography techniques that use an exposure light source having a wavelength shorter (energy higher) than these excimer lasers, such as electron beam (EB), extreme ultraviolet radiation (EUV), and X ray.

In addition, currently, as the resist material in EUV lithography and EB lithography, chemically amplified resists proposed for KrF excimer laser and ArF excimer laser have been generally used since such chemically amplified resists exhibit excellent lithography properties, such as sensitivity to EUV and EB, and resolution sufficient to form a fine resist pattern as a target. In particular, chemically amplified resist containing an acrylic resin as the base material are known to be advantageous in such lithography properties.

Regarding the resist material, particularly in EUV exposure, acid diffusion control was a problem. For controlling acid diffusion, the anion structure of the acid generator is generally changed. Acid generators having an anion structure with a short acid diffusion length are already applied.

For further controlling acid diffusion, methods in which designs of polymeric compounds are variously changed have been employed.

For example, in Patent Literatures 1 to 4, there are described resist compositions in which a polymeric compound having a specific acid dissociable functional group is used to improve the reactivity to acid, thereby contributing to improvement of solubility in a developing solution.

DOCUMENTS OF RELATED ART

Patent Literature

[Patent Literature 1] WO2013/042694
[Patent Literature 2] Japanese Unexamined Patent Application, First Publication No. 2009-114381
[Patent Literature 3] Japanese Unexamined Patent Application, First Publication No. 2012-220800
[Patent Literature 4] WO2010/095698

SUMMARY OF THE INVENTION

As the lithography technique further progresses and the miniaturization of the resist pattern progresses more and more, for example, a target of the lithography performed by electron beams and EUV is to form fine resist patterns of several tens of nanometers.

As miniaturization of pattern progress, improvement will be demanded for resist materials with respect to not only various lithography properties, but also suppressing generation of defects.

The term "defects" refers to general deficiencies within a resist film that are detected when observed from directly above the developed resist pattern using, for example, a surface defect detection apparatus (product name: "KLA") manufactured by KLA-TENCOR Corporation. Examples of these deficiencies include deficiencies caused by adhesion of foreign matters and precipitates on the surface of the resist pattern, such as post-developing scum (residual resist), foam and dust; deficiencies related to resist pattern shape, such as bridges formed between line patterns, and filling-up of holes of a contact hole pattern; and color irregularities of a pattern.

The present invention takes the above circumstances into consideration, with an object of providing a resist composition which can improve lithography properties, and reduce generation of defects.

A first aspect of the present invention is a resist composition which generates acid upon exposure and exhibits changed solubility in a developing solution under action of acid, and which includes a base component (A) which exhibits changed solubility in a developing solution under action of acid and a fluorine additive component (F) which exhibits decomposability to an alkali developing solution, the fluorine additive component (F) including a fluorine resin component (F1) having a structural unit (f1) containing a base dissociable group and a structural unit (f2) containing a group represented by general formula (f2-r-1) shown below.

[Chemical Formula 1.]

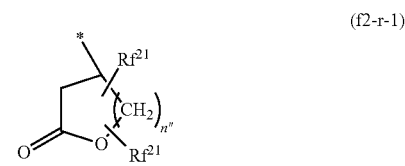

In the formula, each $Rf^{21}$ independently represents a hydrogen atom, an alkyl group, an alkoxy group, a hydroxy group, a hydroxyalkyl group or a cyano group; n" represents an integer of 0 to 2; and * represents a valence bond.

A second aspect of the present invention is a method of forming a resist pattern, including: using a resist composition according to the first aspect to form a resist film on a substrate, exposing the resist film, and alkali developing the exposed resist film to form a resist pattern.

According to the present invention, there are provided a resist composition and a method of forming a resist pattern which can improve lithography properties, and reduce generation of defects.

DETAILED DESCRIPTION OF THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic, divalent saturated hydrocarbon, unless otherwise specified.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with a fluorine atom.

The term "structural unit" refers to a monomer unit that contributes to the formation of a polymeric compound (resin, polymer, copolymer).

The expression "may have a substituent" means that a case where a hydrogen atom (—H) is substituted with a monovalent group, or a case where a methylene (—CH$_2$—) group is substituted with a divalent group.

The term "exposure" is used as a general concept that includes irradiation with any form of radiation.

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid (CH$_2$=CH—COOH) has been substituted with an organic group.

The acrylate ester may have the hydrogen atom bonded to the carbon atom on the α-position substituted with a substituent. The substituent ($R^{\alpha 0}$) that substitutes the hydrogen atom bonded to the carbon atom on the α-position is an atom other than hydrogen or a group, and examples thereof include an alkyl group of 1 to 5 carbon atoms and a halogenated alkyl group of 1 to 5 carbon atoms. Further, an acrylate ester having the hydrogen atom bonded to the carbon atom on the α-position substituted with a substituent ($R^{\alpha 0}$) in which the substituent has been substituted with a substituent containing an ester bond (e.g., an itaconic acid diester), or an acrylic acid having the hydrogen atom bonded to the carbon atom on the α-position substituted with a substituent ($R^{\alpha 0}$) in which the substituent has been substituted with a hydroxyalkyl group or a group in which the hydroxy group within a hydroxyalkyl group has been modified (e.g., α-hydroxyalkyl acrylate ester) can be mentioned as an acrylate ester having the hydrogen atom bonded to the carbon atom on the α-position substituted with a substituent. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester".

A "structural unit derived from acrylamide" refers to a structural unit that is formed by the cleavage of the ethylenic double bond of acrylamide.

The acrylamide may have the hydrogen atom bonded to the carbon atom on the α-position substituted with a substituent, and may have either or both terminal hydrogen atoms on the amino group of acrylamide substituted with a substituent. A carbon atom on the α-position of an acrylamide refers to the carbon atom bonded to the carbonyl group, unless specified otherwise.

As the substituent which substitutes the hydrogen atom on the α-position of acrylamide, the same substituents as those described above for the substituent ($R^{\alpha 0}$) on the α-position of the aforementioned α-position of the aforementioned α-substituted acrylate ester can be mentioned.

A "structural unit derived from hydroxystyrene" refers to a structural unit that is formed by the cleavage of the ethylenic double bond of hydroxystyrene. A "structural unit derived from a hydroxystyrene derivative" refers to a structural unit that is formed by the cleavage of the ethylenic double bond of a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxy group has been substituted with an organic group and may have the hydrogen atom on the α-position substituted with a substituent; and hydroxystyrene which has a substituent other than a hydroxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

As the substituent which substitutes the hydrogen atom on the α-position of hydroxystyrene, the same substituents as those described above for the substituent on the α-position of the aforementioned α-substituted acrylate ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include benzoic acid in which the hydrogen atom of the carboxy group has been substituted with an organic group and may have the hydrogen atom on the α-position substituted with a substituent; and benzoic acid which has a substituent other than a hydroxy group and a carboxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

The term "styrene" is a concept including styrene and compounds in which the hydrogen atom at the α-position of styrene is substituted with other substituent such as an alkyl group and a halogenated alkyl group.

The term "styrene derivative" includes compounds in which the hydrogen atom at the α-position of styrene has been substituted with another substituent such as an alkyl group or a halogenated alkyl group; and derivatives thereof.

Examples of the derivatives thereof include hydroxystyrene which has a substituent other than a hydroxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

A "structural unit derived from styrene" or "structural unit derived from a styrene derivative" refers to a structural unit that is formed by the cleavage of the ethylenic double bond of styrene or a styrene derivative.

As the alkyl group as a substituent on the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

(Resist Composition)

The resist composition according to a first aspect of the present invention is a resist composition which generates acid upon exposure and exhibits changed solubility in a developing solution under action of acid, and which includes a base component (A) (hereafter, sometimes referred to as "component (A)") which exhibits changed solubility in a developing solution under action of acid and a fluorine additive component (F) (hereafter, sometimes referred to as "component (F)") which exhibits decomposability to an alkali developing solution, the fluorine additive component (F) including a fluorine resin component (F1) having a structural unit (f1) containing a base dissociable group and a structural unit (f2) containing a group represented by general formula (f2-r-1) shown below.

In the present embodiment, the component (A) may be constituted of a single polymeric compound, or a mixture of a plurality of polymeric compounds.

When a resist film is formed using the resist composition and the formed resist film is subjected to a selective exposure, acid is generated at exposed portions, and the generated acid acts on the component (A) to change the solubility of the component (A) in a developing solution, whereas the solubility of the component (A) in a developing solution is not changed at unexposed portions, thereby generating difference in solubility in a developing solution between exposed portions and unexposed portions. Therefore, by subjecting the resist film to development, the exposed portions are dissolved and removed to form a positive-tone resist pattern in the case of a positive resist, whereas the unexposed portions are dissolved and removed to form a negative-tone resist pattern in the case of a negative resist.

In the present specification, a resist composition which forms a positive resist pattern by dissolving and removing the exposed portions is called a positive resist composition, and a resist composition which forms a negative resist pattern by dissolving and removing the unexposed portions is called a negative resist composition.

In the present embodiment, the resist composition may be either a positive resist composition or a negative resist composition.

Further, in the present invention, the resist composition is applicable to an alkali developing process using an alkali developing solution in the developing treatment, or a solvent developing process using a developing solution containing an organic solvent (organic developing solution) in the developing treatment, but is preferably applicable to an alkali developing process.

In the present embodiment, the resist composition has a function of generating acid upon exposure, and in the resist composition, the component (A) may generate acid upon exposure, or an additive component other than the component (A) may generate acid upon exposure.

More specifically, in the present embodiment, the resist composition may be a resist composition (1) containing an acid generator component (B) which generates acid upon exposure (hereafter, referred to as "component (B)");

a resist composition (2) in which the component (A) is a component which generates acid upon exposure; or a resist composition (3) in which the component (A) is a component which generates acid upon exposure, and further containing an acid generator component (B).

That is, when the resist composition of the present invention is the aforementioned resist composition (2) or (3), the component (A) is a "base component which generates acid upon exposure and exhibits changed solubility in a developing solution under action of acid". In the case where the component (A) is a base component which generates acid upon exposure and exhibits changed solubility in a developing solution under action of acid, the component (A) described later is preferably a polymeric compound which generates acid upon exposure and exhibits changed solubility in a developing solution under action of acid. As the polymeric compound, a resin having a structural unit which generates acid upon exposure can be used. As the structural unit which generates acid upon exposure, a conventional structural unit can be used.

In the present embodiment, it is particularly desirable that the resist composition is the aforementioned resist composition (1).

<Component (A)>

In the present invention, the term "base component" refers to an organic compound capable of forming a film, and is preferably an organic compound having a molecular weight of 500 or more. When the organic compound has a molecular weight of 500 or more, the film-forming ability is improved, and a photosensitive resin pattern of nano level can be easily formed.

The organic compound used as the base component is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. Hereafter, a "resin" refers to a polymer having a molecular weight of 1,000 or more.

As the molecular weight of the polymer, the weight average molecular weight in terms of the polystyrene equivalent value determined by gel permeation chromatography (GPC) is used.

As the component (A'), a resin, a low molecular weight compound, or a combination thereof may be used.

The component (A) may be a resin that exhibits increased solubility in a developing solution under action of acid or a resin that exhibits decreased solubility in a developing solution under action of acid.

In the present invention, the component (A) may be a component that generates acid upon exposure.

In the present invention, the component (A) preferably includes a resin component (A1) (hereafter, sometimes referred to as "component (A1)") which has at least one structural unit selected from the group consisting of the structural units (a10), (a1), (a2) and (a3) described later.

(Structural Unit (a1))

The structural unit (a1) is a structural unit containing an acid decomposable group that exhibits increased polarity by the action of acid.

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group (—SO₃H). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

The "acid dissociable group" refers to both (i) a group in which the bond between the acid dissociable group and the adjacent atom is cleaved by the action of acid; and (ii) a group in which one of the bonds is cleaved by the action of acid, and then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

Examples of the acid dissociable group include groups which have been proposed as acid dissociable groups for the base resin of a conventional chemically amplified resist composition.

Specific examples of acid dissociable groups for the base resin of a conventional chemically amplified resist composition include "acetal-type acid dissociable group", "tertiary alkyl ester-type acid dissociable group" and "tertiary alkyloxycarbonyl acid dissociable group" described below.

Acetal-Type Acid Dissociable Group

Examples of the acid dissociable group for protecting the carboxy group or hydroxy group as a polar group include the acid dissociable group represented by general formula (a1-r-1) shown below (hereafter, referred to as "acetal-type acid dissociable group").

[Chemical Formula 2.]

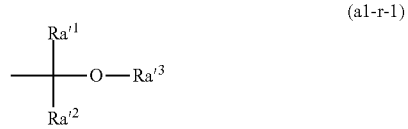

(a1-r-1)

In the formula, $Ra'^1$ and $Ra'^2$ each independently represents a hydrogen atom or an alkyl group; and $Ra'^3$ represents a hydrocarbon group, provided that $Ra'^3$ may be bonded to $Ra'^1$ or $Ra'^2$.

In the formula (a1-r-1), it is preferable that at least one of $Ra'^1$ and $Ra'^2$ represents a hydrogen atom, and it is more preferable that both of $Ra'^1$ and $Ra'^2$ represent a hydrogen atom.

In the case where $Ra'^1$ or $Ra'^2$ is an alkyl group, as the alkyl group, the same alkyl groups as those described above the for the substituent which may be bonded to the carbon atom on the α-position of the aforementioned α-substituted acrylate ester can be mentioned, and an alkyl group of 1 to 5 carbon atoms is preferable. Specific examples include linear or branched alkyl groups. Specific examples of the alkyl group include a methyl group, an ethyl group, a propyl group, an isopropyl group, an n-butyl group, an isobutyl group, a tert-butyl group, a pentyl group, an isopentyl group and a neopentyl group. Of these, a methyl group or an ethyl group is preferable, and a methyl group is particularly preferable.

In formula (a1-r-1), examples of the hydrocarbon group for $Ra'^3$ include a linear or branched alkyl group and a cyclic hydrocarbon group.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

In the case where $Ra'^3$ represents a cyclic hydrocarbon group, the cyclic hydrocarbon group may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

When the monovalent hydrocarbon group for $Ra^{t3}$ is an aromatic hydrocarbon group, the aromatic hydrocarbon group is a hydrocarbon group having at least one aromatic ring.

The aromatic ring is not particularly limited, as long as it is a cyclic conjugated compound having (4n+2) π electrons, and may be either monocyclic or polycyclic. The aromatic ring preferably has 5 to 30 carbon atoms, more preferably 5 to 20, still more preferably 6 to 15, and most preferably 6 to 12.

Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group for $Ra^{t3}$ include a group in which one hydrogen atom has been removed from the aforementioned aromatic hydrocarbon ring or aromatic hetero ring (aryl group or heteroaryl group); a group in which one hydrogen atom has been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aforementioned aromatic hydrocarbon ring or the aromatic hetero ring preferably has 1 to 4 carbon atoms, more preferably 1 or 2 carbon atoms, and most preferably 1 carbon atom.

The cyclic hydrocarbon group for $Ra^{t3}$ may have a substituent. Examples of the substituent include —$R^{P1}$, —$R^{P2}$—O—$R^{P1}$, —$R^{P2}$—CO—$R^{P1}$, —$R^{P2}$—CO—O$R^{P1}$, —$R^{P2}$—O—CO—$R^{P1}$, —$R^{P2}$—OH, —$R^{P2}$—CN or —$R^{P2}$—COOH (hereafter, these substituents are sometimes collectively referred to as "$Ra^{05}$").

Here, $R^{P1}$ is a monovalent chain saturated hydrocarbon group having 1 to 10 carbon atoms, a monovalent aliphatic cyclic saturated hydrocarbon group having 3 to 20 carbon atoms, or a monovalent aromatic hydrocarbon group having 6 to 30 carbon atoms. Further, $R^{P2}$ is a single bond, a divalent chain saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms.

Here, a portion or all of the hydrogen atoms having the chain saturated hydrocarbon group, the aliphatic cyclic saturated hydrocarbon group, and the aromatic hydrocarbon group for $R^{P1}$ and $R^{P2}$ may be substituted with a fluorine atom. The aliphatic cyclic hydrocarbon group may have 1 or more substituents of 1 kind, or 1 or more substituents of a plurality of kinds.

Examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; and a polycyclic aliphatic saturated hydrocarbon group such as a bicyclo[2.2.2]octanyl group, a tricyclo[5.2.1.0$^{2,6}$]decanyl group, a tricyclo[3.3.1.1$^{3,7}$]decanyl group, a tetracyclo[6.2.1.13,6.0$^{2,7}$]dodecanyl group, and an adamantyl group.

Examples of the monovalent aromatic hydrocarbon group having 6 to 30 carbon atoms include a group obtained by removing one hydrogen atom from the aromatic hydrocarbon ring such as benzene, biphenyl, fluorene, naphthalene, anthracene, and phenanthrene.

In the case where $Ra^{t3}$ is bonded to $Ra^{t1}$ or $Ra^{t2}$ to form a ring, the cyclic group is preferably a 4 to 7-membered ring, and more preferably a 4 to 6-membered ring. Specific examples of the cyclic group include tetrahydropyranyl group and tetrahydrofuranyl group.

Tertiary Alkyl Ester-Type Acid Dissociable Group

Examples of the acid dissociable group for protecting the carboxy group as a polar group include the acid dissociable group represented by general formula (a1-r-2) shown below.

Among the acid dissociable groups represented by general formula (a1-r-2), for convenience, a group which is constituted of alkyl groups is referred to as "tertiary ester-type acid dissociable group".

[Chemical Formula 3.]

(a1-r-2)

In the formula, $Ra^{t4}$ to $Ra^{t6}$ each independently represents a hydrocarbon group, provided that $Ra^{t5}$ and $Ra^{t6}$ may be mutually bonded to form a ring.

Examples of the hydrocarbon group for $Ra^{t4}$ include a linear or branched alkyl group, a chain or cyclic alkenyl group, and a cyclic hydrocarbon group.

The linear or branched alkyl group and the cyclic hydrocarbon group (monocyclic aliphatic hydrocarbon group, polycyclic aliphatic hydrocarbon group or aromatic hydrocarbon group) for $Ra^{t4}$ are the same as defined for $Ra^{t3}$.

The chain or cyclic alkenyl group for $Ra^{t4}$ is preferably an alkenyl group having 2 to 10 carbon atoms.

The hydrocarbon group for $Ra^{t5}$ and $Ra^{t6}$ is the same as defined for $Ra^{t3}$.

In the case where $Ra^{t5}$ and $Ra^{t6}$ are mutually bonded to form a ring, a group represented by general formula (a1-r2-1) shown below, a group represented by general formula (a1-r2-2) shown below, and a group represented by general formula (a1-r2-3) shown below may be given as preferable examples.

On the other hand, in the case where $Ra^{t4}$ to $Ra^{t6}$ are not mutually bonded and independently represent a hydrocarbon group, the group represented by general formula (a1-r2-4) shown below may be given as a preferable example.

[Chemical Formula 4.]

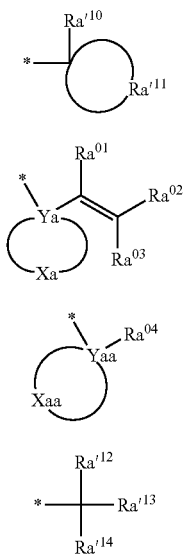

(a1-r2-1)
(a1-r2-2)
(a1-r2-3)
(a1-r2-4)

In formula (a1-r2-1), $Ra'^{10}$ represents an alkyl group of 1 to 10 carbon atoms; $Ra'^{11}$ is a group which forms an aliphatic cyclic group together with a carbon atom having $Ra'^{10}$ bonded thereto. In formula (a1-r2-2), Ya represents a carbon atom; Xa represents a group which forms a cyclic hydrocarbon group together with Ya, provided that part or all of the hydrogen atoms of the cyclic hydrocarbon group may be substituted; $Ra^{01}$ to $Ra^{03}$ each independently represents a hydrogen atom, a monovalent saturated chain hydrocarbon group of 1 to 10 carbon atoms or a monovalent saturated aliphatic cyclic hydrocarbon group of 3 to 20 carbon atoms, provided that part or all of the hydrogen atoms of the saturated chain hydrocarbon or the saturated aliphatic cyclic hydrocarbon may be substituted; two or more of $Ra^{01}$ to $Ra^{03}$ may be mutually bonded to form a cyclic structure; and * represents a valence bond. In formula (a1-r2-3), Yaa represents a carbon atom; Xaa represents a group which forms an aliphatic cyclic group together with Yaa; $Ra^{04}$ represents an aromatic hydrocarbon group which may have a substituent; and * represents a valence bond. In formula (a1-r2-4), $Ra'^{12}$ and $Ra'^{13}$ each independently represents a hydrogen atom or a monovalent saturated hydrocarbon group of 1 to 10 carbon atoms, provided that part or all of the hydrogen atoms of the saturated hydrocarbon group may be substituted; $Ra'^{14}$ represents an aromatic hydrocarbon group which may have a substituent; and * represents a valence bond (the same definition hereafter).

In the formula (a1-r2-1), as the alkyl group of 1 to 10 carbon atoms for $Ra'^{10}$, the same groups as described above for the linear or branched alkyl group for $Ra'^{3}$ in the formula (a1-r-1) are preferable.

$Ra'^{10}$ is preferably an alkyl group of 1 to 5 carbon atoms.

In formula (a1-r2-1), the aliphatic cyclic group which is formed by $Ra'^{11}$ together with the carbon atom bonded to $Ra'^{10}$, the same groups as those described above for the monocyclic or polycyclic aliphatic hydrocarbon group for $Ra'^{3}$ in formula (a1-r-1) are preferable.

In formula (a1-r2-2), as the cyclic hydrocarbon group formed by Xa together with Ya, a group in which 1 or more hydrogen atoms have been removed from the monovalent cyclic hydrocarbon group (aliphatic hydrocarbon group or aromatic hydrocarbon group) for $Ra'^{3}$ in the aforementioned formula (a1-r-1) may be mentioned.

The cyclic hydrocarbon group which Xa forms with Ya may have a substituent. Examples of substituents include the same substituents as those which the cyclic hydrocarbon group for $Ra'^{3}$ may have.

In formula (a1-r2-2), examples of the monovalent saturated chain hydrocarbon group of 1 to 10 carbon atoms for $Ra^{01}$ to $Ra^{03}$ include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms for $Ra^{01}$ to $Ra^{03}$ include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; and a polycyclic aliphatic saturated hydrocarbon group such as a bicyclo[2.2.2]octanyl group, a tricyclo[5.2.1.0$^{2,6}$]decanyl group, a tricyclo[3.3.1.1$^{3,7}$]decanyl group, a tetracyclo[6.2.1.13,6.0$^{2,7}$]dodecanyl group, and an adamantyl group.

Among these examples, as $Ra^{01}$ to $Ra^{03}$, in terms of ease in synthesis of the monomeric compound which derives the structural unit (a1), a hydrogen atom or a saturated chain hydrocarbon group having 1 to 10 carbon atoms is preferable, a hydrogen atom, a methyl group or an ethyl group is more preferable, and a hydrogen atom is most preferable.

As the substituent for the saturated chain hydrocarbon group or saturated cyclic aliphatic hydrocarbon group represented by $Ra^{01}$ to $Ra^{03}$, for example, the same substituents as those described above for $Ra^{05}$ may be mentioned.

Examples of the group containing a carbon-carbon double bond which is generated by forming a cyclic structure in which two or more of $Ra^{01}$ to $Ra^{03}$ are bonded to each other include a cyclopentenyl group, a cyclohexenyl group, a methyl cyclopentenyl group, a methyl cyclohexenyl group, a cyclopentylideneethenyl group, and a cyclohexylideneethenyl group. Among these examples, from the viewpoint of the ease of synthesis of the monomer compound which derives the structural unit (a1), a cyclopentenyl group, a cyclohexenyl group, and a cyclopentylideneethenyl group are preferable.

In formula (a1-r2-3), an aliphatic cyclic group which is formed of Xaa together with Yaa is preferably a group exemplified as an aliphatic hydrocarbon group which is a monocyclic group or a polycyclic group of $Ra'^{3}$ in general formula (a1-r-1).

In general formula (a1-r2-3), examples of the aromatic hydrocarbon group for $Ra^{04}$ include a group obtained by removing one or more hydrogen atoms from an aromatic hydrocarbon ring having 5 to 30 carbon atoms. Among these examples, $R^{04}$ is preferably a group obtained by removing one or more hydrogen atoms from an aromatic hydrocarbon ring having 6 to 15 carbon atoms, a group obtained by removing one or more hydrogen atoms from benzene, naphthalene, anthracene, or phenanthrene is further preferable, a group obtained by removing one or more hydrogen atoms from benzene, naphthalene, or anthracene is still further preferable, a group obtained by removing one or more hydrogen atoms from benzene and naphthalene is particularly preferable, and a group obtained by removing one or more hydrogen atoms from benzene is most preferable.

Examples of the substituent that $Ra^{04}$ in general formula (a1-r2-3) may have include a methyl group, an ethyl group, a propyl group, a hydroxyl group, a carboxyl group, a halogen atom (a fluorine atom, a chlorine atom, a bromine atom, or the like), an alkoxy group (a methoxy group, an ethoxy group, a propoxy group, a butoxy group, or the like), and an alkyloxycarbonyl group.

In general formula (a1-r2-4), $Ra'^{12}$ and $Ra'^{13}$ each independently represent a monovalent chain saturated hydrocarbon group having 1 to 10 carbon atoms or a hydrogen atom. With respect to $Ra'^{12}$ and $Ra'^{13}$, examples of the monovalent chain saturated hydrocarbon group having 1 to 10 carbon atoms include the same monovalent chain saturated hydrocarbon group having 1 to 10 carbon atoms as that for $Ra^{01}$ to $Ra^{03}$, provided that part or all of the hydrogen atoms of the saturated hydrocarbon group may be substituted;

Among these examples, as $Ra'^{12}$ and $Ra'^{13}$, a hydrogen atom and an alkyl group having 1 to 5 carbon atoms are preferable, an alkyl group having 1 to 5 carbon atoms is further preferable, a methyl group and an ethyl group are still further preferable, and a methyl group is particularly preferable.

In the case where the chain saturated hydrocarbon group represented by $Ra'^{12}$ and $Ra'^{13}$ is substituted, examples of the substituent include the same group as that of $Ra^{05}$.

In general formula (a1-r2-4), $Ra'^{14}$ is an aromatic hydrocarbon group which may have a substituent. Examples of the hydrocarbon group for $Ra'^{14}$ include the same aromatic hydrocarbon groups as those exemplified in the description for $Ra^{04}$. Among these examples, $Ra'^{14}$ is preferably a group obtained by removing one or more hydrogen atoms from the aromatic hydrocarbon group having 6 to 15 carbon atoms, is further preferably a group obtained by removing one or more hydrogen atoms from benzene, naphthalene, anthracene, or phenanthrene, is still further preferably a group obtained by removing one or more hydrogen atoms from benzene, naphthalene, or anthracene, is particularly preferably a group obtained by removing one or more hydrogen atoms from naphthalene or anthracene, and is most preferably a group obtained by removing one or more hydrogen atoms from naphthalene.

Examples of the substituent that $Ra'^{14}$ may have include the same group as the substituent that $Ra^{04}$ may have.

In the case where $Ra'^{14}$ in general formula (a1-r2-4) is a naphthyl group, a position which is bonded to a tertiary carbon atom in general formula (a1-r2-4) may be 1-position and 2-position of the naphthyl group.

In the case where $Ra'^{14}$ in general formula (a1-r2-4) is an anthryl group, a position which is bonded to a tertiary carbon atom in general formula (a1-r2-4) may be any one of 1-position, 2-position, and 9-position of the anthryl group.

Specific examples of the group represented by the aforementioned formula (a1-r2-1) are shown below.

[Chemical Formula 5.]

(r-pr-m1)

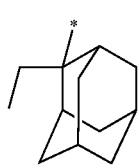

(r-pr-m2)

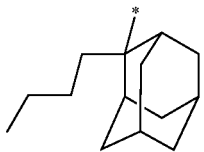

(r-pr-m3)

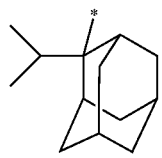

(r-pr-m4)

(r-pr-m5)

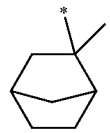

(r-pr-m6)

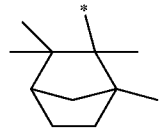

(r-pr-m7)

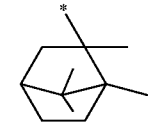

(r-pr-m8)

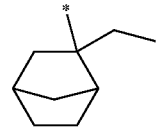

(r-pr-m9)

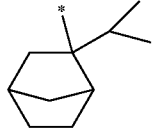

(r-pr-m10)

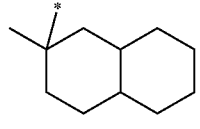

(r-pr-m11)

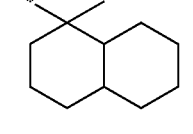

(r-pr-m12)

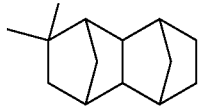

(r-pr-m13)

-continued
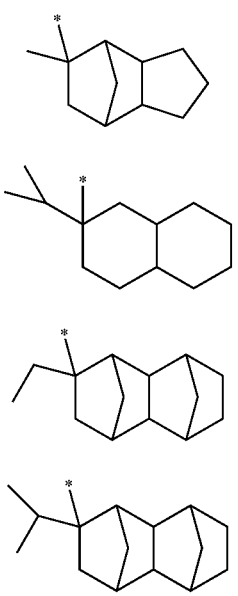
[Chemical Formula 6.]
(r-pr-m14)
(r-pr-m15)
(r-pr-m16)
(r-pr-m17)
(r-pr-s1)
(r-pr-s2)
(r-pr-s3)
(r-pr-s4)
(r-pr-s5)
(r-pr-s6)
(r-pr-s7)
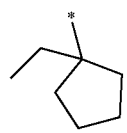
(r-pr-s8)
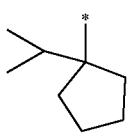
(r-pr-s9)
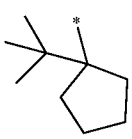
(r-pr-s10)
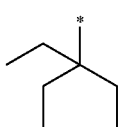
(r-pr-s11)
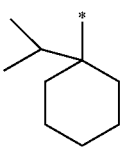
(r-pr-s12)
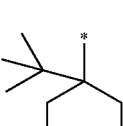
(r-pr-s13)
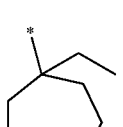
(r-pr-s14)
(r-pr-s15)
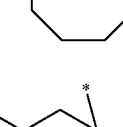
(r-pr-s16)
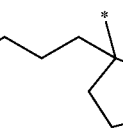

-continued
(r-pr-s17)
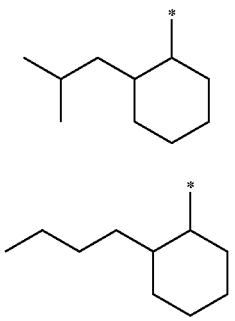
(r-pr-s18)
Specific examples of the group represented by the aforementioned formula (a1-r2-2) are shown below.
[Chemical Formula 7.]
(r-pr-sv1)
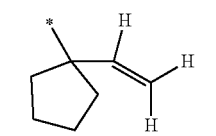
(r-pr-sv2)
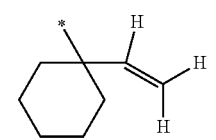
(r-pr-sv3)
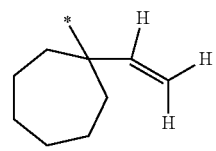
(r-pr-sv4)
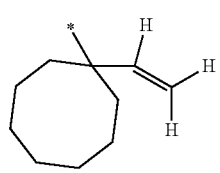
(r-pr-sv5)
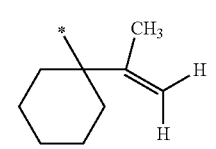
(r-pr-sv6)
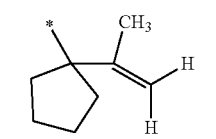
(r-pr-sv7)
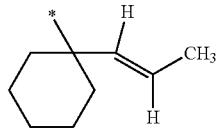
-continued
(r-pr-sv8)
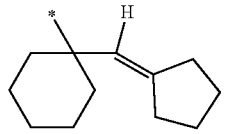
(r-pr-sv9)
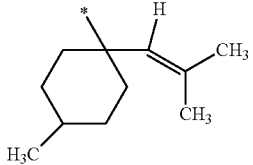
(r-pr-sv10)
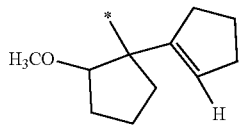
(r-pr-sv11)
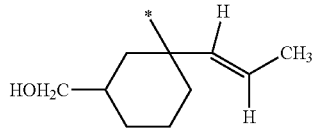
(r-pr-sv12)
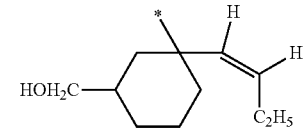
[Chemical Formula 8.]
(r-pr-mv1)
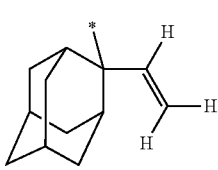
(r-pr-mv2)
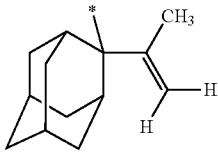
(r-pr-mv3)
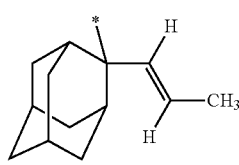
(r-pr-mv4)
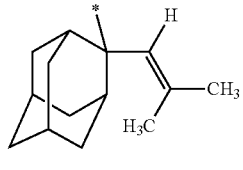
(r-pr-mv5)
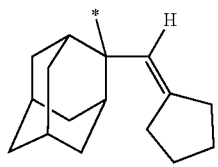

(r-pr-mv6)
(r-pr-mv7)
(r-pr-mv8)
(r-pr-mv9)

[Chemical Formula 9.]

(r-pr-mv10)
(r-pr-mv11)
(r-pr-mv12)
(r-pr-mv13)

(r-pr-mv14)
(r-pr-mv15)
(r-pr-mv16)
(r-pr-mv17)
(r-pr-mv18)
(r-pr-mv19)
(r-pr-mv20)
(r-pr-mv21)

21
-continued
[Chemical Formula 10.]
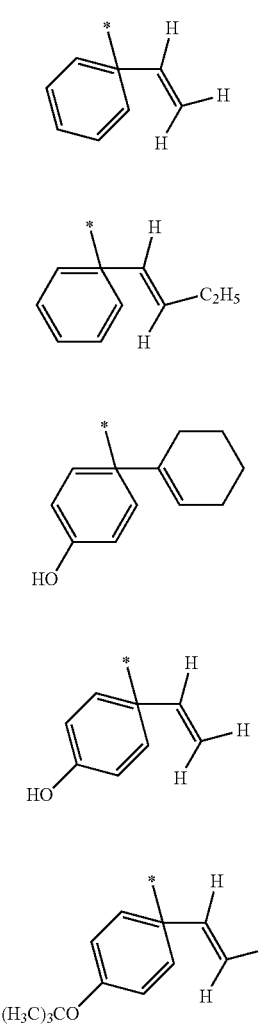
(r-pr-av1)
(r-pr-av2)
(r-pr-av3)
(r-pr-av4)
(r-pr-av5)
Specific examples of the group represented by the aforementioned formula (a1-r2-3) are shown below.
[Chemical Formula 11.]
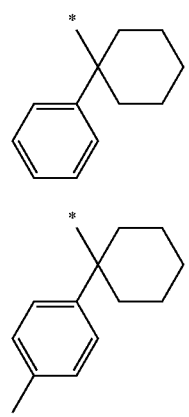
(r-pr-sa1)
(r-pr-sa2)
22
-continued
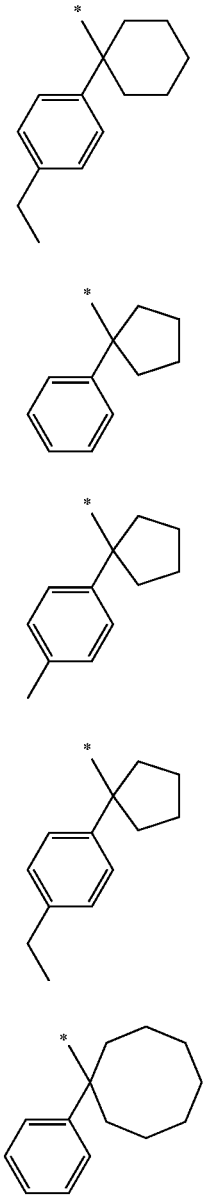
(r-pr-sa3)
(r-pr-sa4)
(r-pr-sa5)
(r-pr-sa6)
(r-pr-sa7)
(r-pr-sa8)
(r-pr-sa9)

-continued (r-pr-ma1)
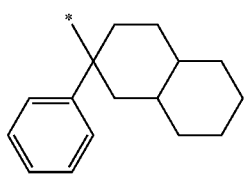

(r-pr-ma2)
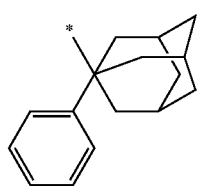

Specific examples of the group represented by the aforementioned formula (a1-r2-4) are shown below.

[Chemical Formula 12.]

(r-pr-cm1)
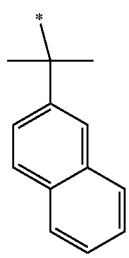

(r-pr-cm2)
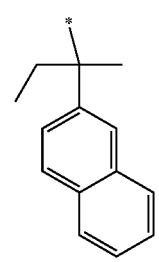

(r-pr-cm3)
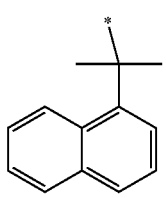

(r-pr-cm4)
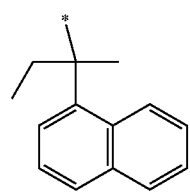

-continued (r-pr-cs1)
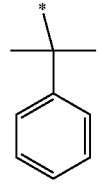

(r-pr-cs2)
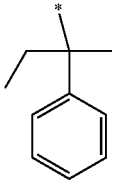

Tertiary Alkyloxycarbonyl Acid Dissociable Group

Examples of the acid dissociable group for protecting a hydroxy group as a polar group include the acid dissociable group represented by general formula (a1-r-3) shown below (hereafter, for convenience, referred to as "tertiary alkyloxycarbonyl-type acid dissociable group").

[Chemical Formula 13.]

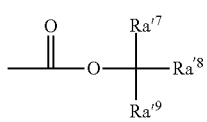
(a1-r-3)

In the formula, $Ra'^7$ to $Ra'^9$ each independently represents an alkyl group.

In the formula (a1-r-3), $Ra'^7$ to $Ra'^9$ is preferably an alkyl group of 1 to 5 carbon atoms, and more preferably an alkyl group of 1 to 3 carbon atoms.

Further, the total number of carbon atoms within the alkyl group is preferably 3 to 7, more preferably 3 to 5, and most preferably 3 or 4.

Examples of the structural unit (a1) include a structural unit derived from an acrylate ester which may have the hydrogen atom bonded to the carbon atom on the α-position substituted with a substituent; a structural unit derived from an acrylamide; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

As the structural unit (a1), a structural unit derived from an acrylate ester which may have the hydrogen atom bonded to the carbon atom on the α-position substituted with a substituent is preferable.

Specific examples of preferable structural units for the structural unit (a1) include structural units represented by general formula (a1-1) or (a1-2) shown below.

[Chemical Formula 14.]

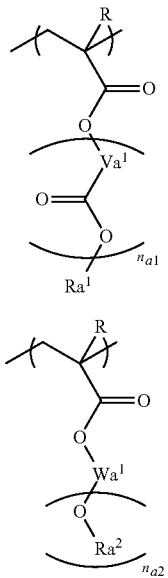

(a1-1)

(a1-2)

In the formula, R represents a hydrogen atom, an alkyl group of 1 to 5 carbon atoms or a halogenated alkyl group of 1 to 5 carbon atoms; $Va^1$ represents a divalent hydrocarbon group optionally having an ether bond; $n_{a1}$ represents an integer of 0 to 2; $Ra^1$ represents an acid dissociable group represented by the aforementioned formula(a1-r-1) or (a1-r-2); $Wa^1$ represents a hydrocarbon group having a valency of $n_{a2}+1$; $n_{a2}$ represents an integer of 1 to 3; and $Ra^2$ represents an acid dissociable group represented by the aforementioned formula (a1-r-1) or (a1-r-3).

In the aforementioned formula (a1-1), as the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In formula (a1-1), the divalent hydrocarbon group for $V^1$ may be either an aliphatic hydrocarbon group or an aromatic hydrocarbon group.

The aliphatic hydrocarbon group as the divalent hydrocarbon group for $Va^1$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched aliphatic hydrocarbon group preferably has 3 to 10 carbon atoms, more preferably 3 to 6 carbon atoms, still more preferably 3 or 4 carbon atoms, and most preferably 3 carbon atoms.

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. The linear or branched aliphatic hydrocarbon group is the same as defined for the aforementioned linear aliphatic hydrocarbon group or the aforementioned branched aliphatic hydrocarbon group.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group as the divalent hydrocarbon group for $Va^1$ is a hydrocarbon group having an aromatic ring.

The aromatic hydrocarbon group preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2, and most preferably 1.

In formula (a1-1), Ra$^1$ represents an acid dissociable group represented by the aforementioned formula (a1-r-1) or (a1-r-2).

In the aforementioned formula (a1-2), the hydrocarbon group for Wa$^1$ having a valency of $n_{a2}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof.

The valency of $n_{a2}+1$ is preferably divalent, trivalent or tetravalent, and divalent or trivalent is more preferable.

Specific examples of structural unit represented by formula (a1-1) are shown below. In the formulae shown below, R$^\alpha$ represents a hydrogen atom, a methyl group or a trifluoromethyl group.

[Chemical Formula 15.]

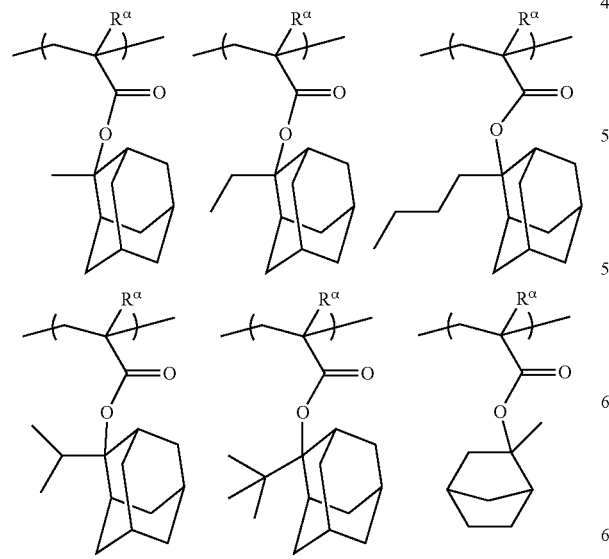

[Chemical Formula 16.]

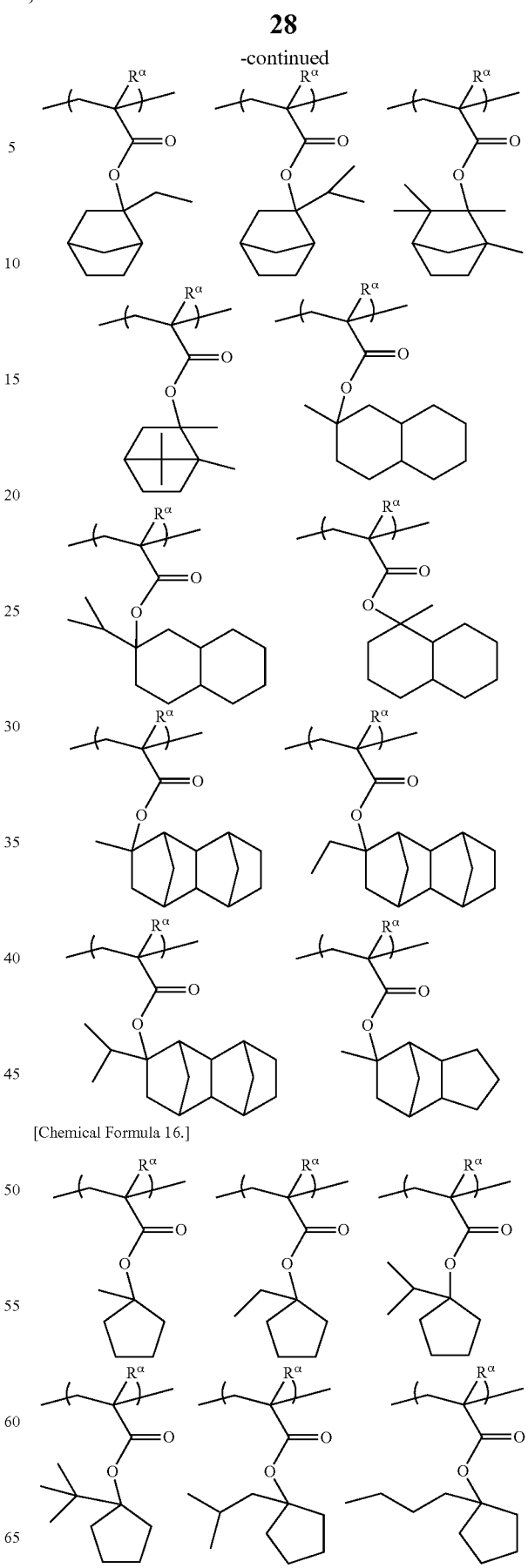

-continued
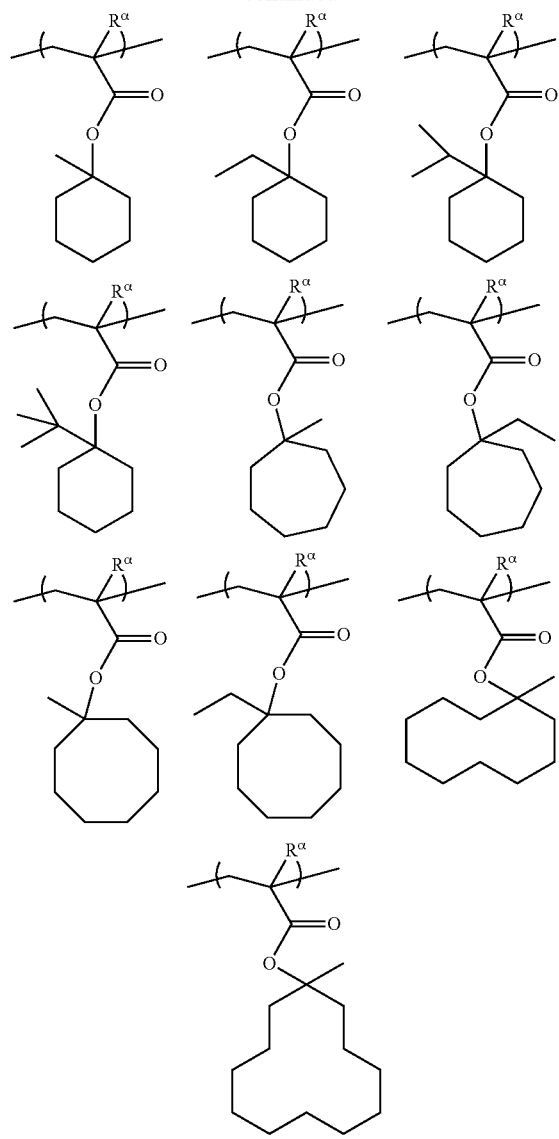
[Chemical Formula 17.]
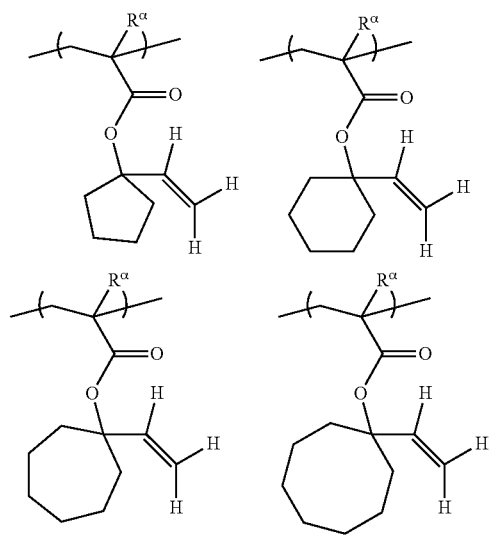
-continued
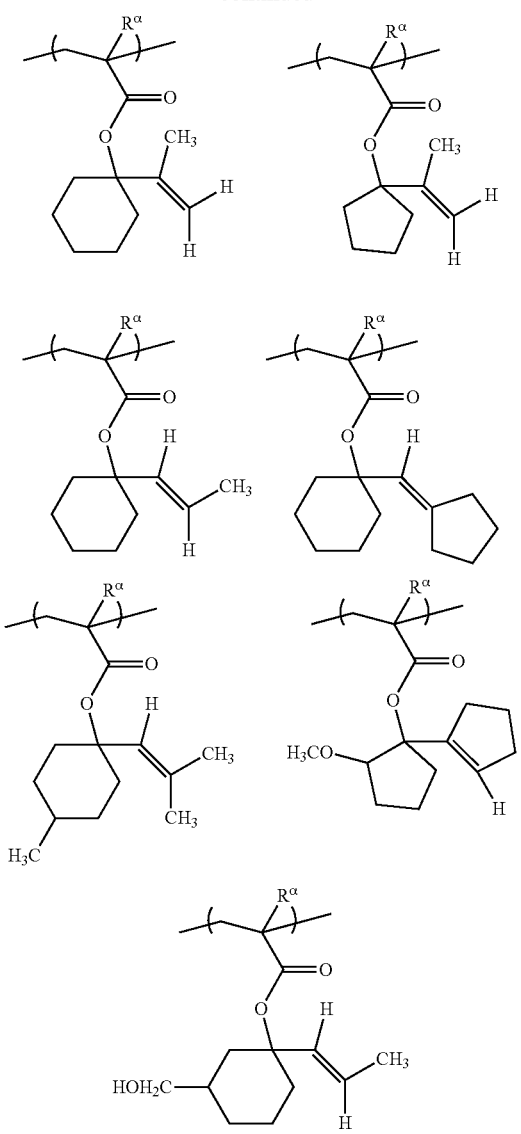
[Chemical Formula 18.]
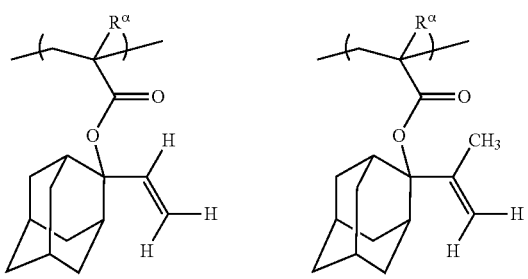

-continued
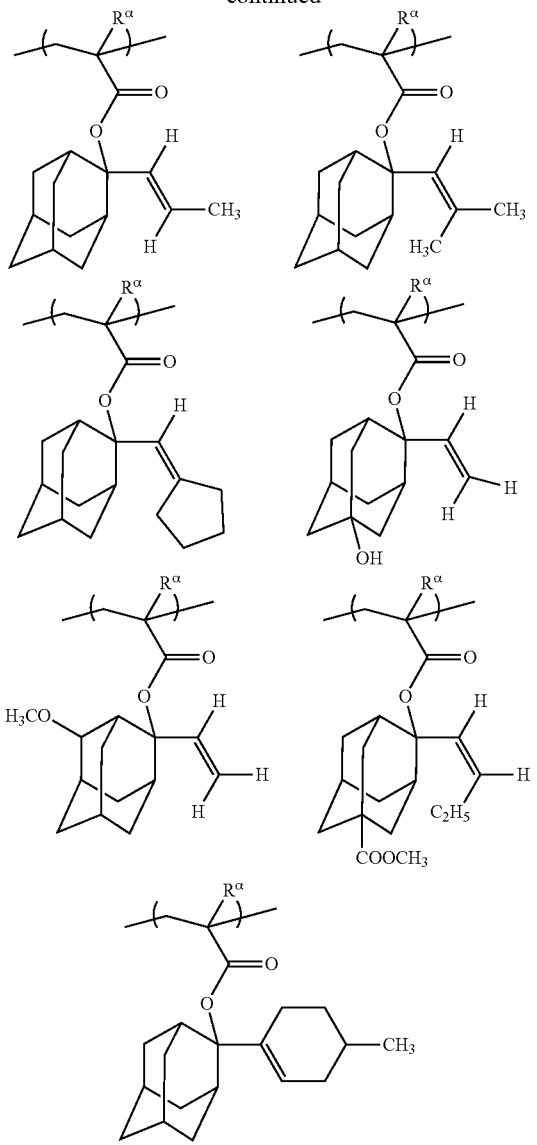
[Chemical Formula 19.]
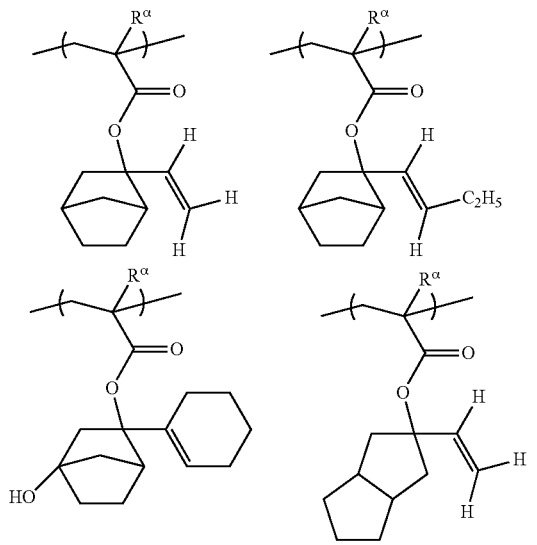
-continued
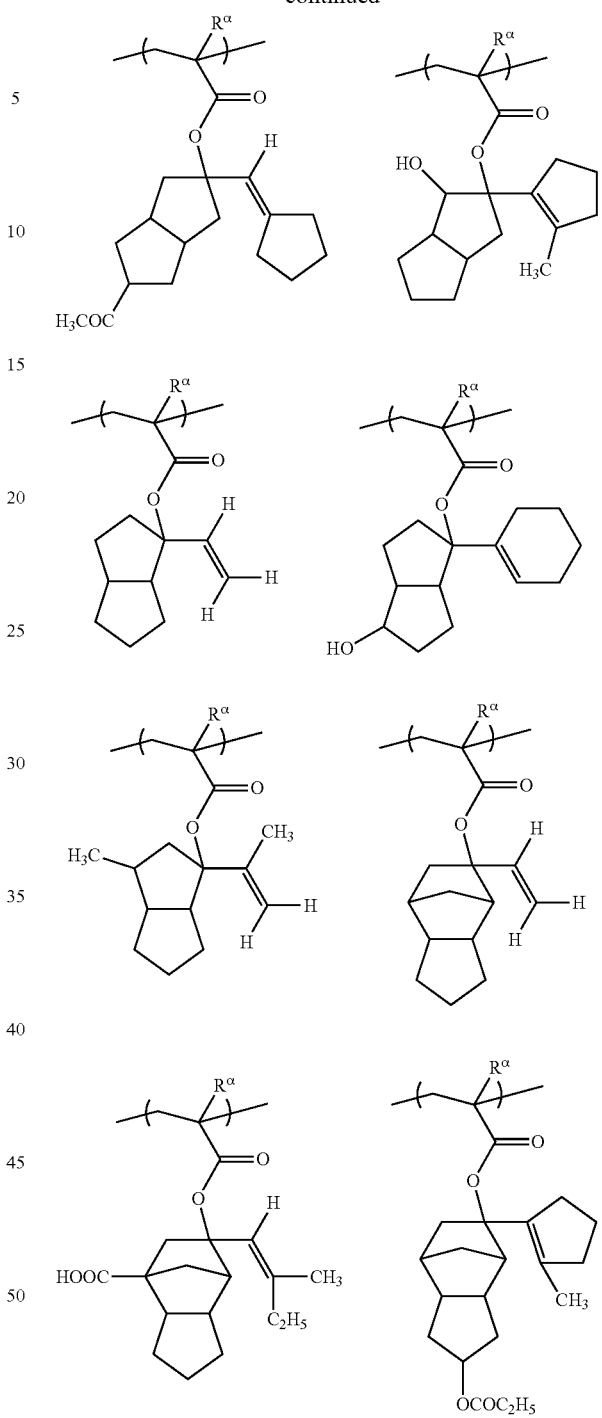
[Chemical Formula 20.]
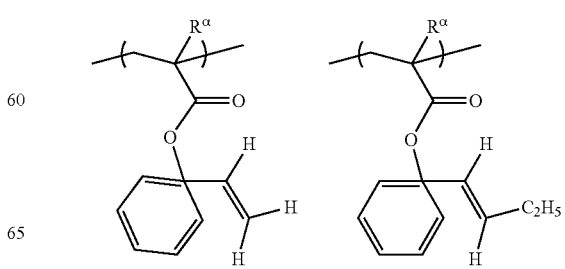

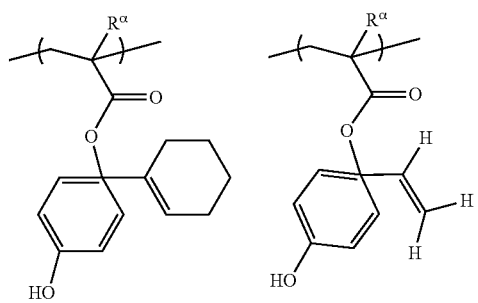
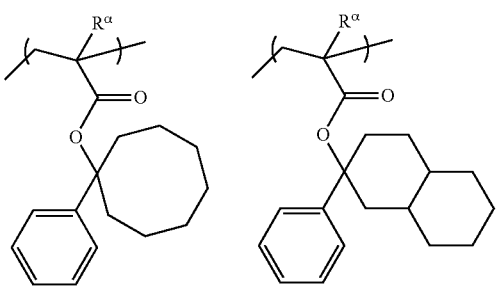
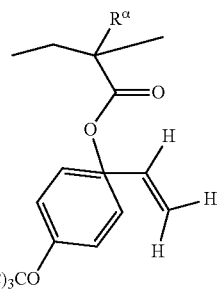
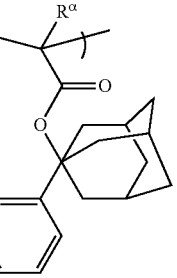
[Chemical Formula 21.]
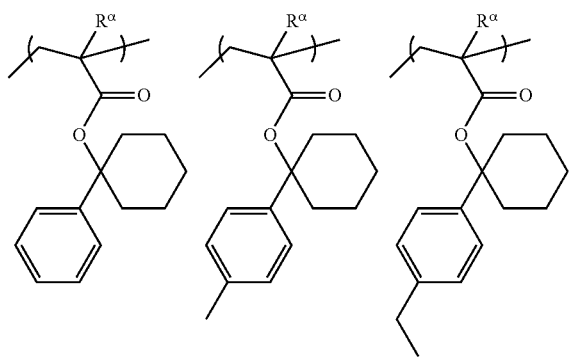
[Chemical Formula 22.]
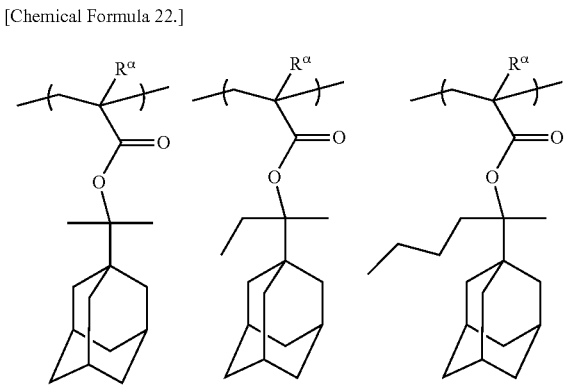
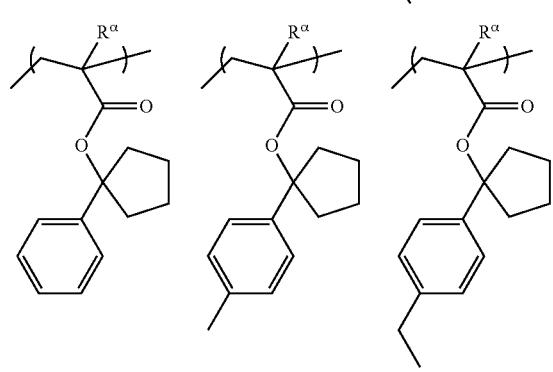
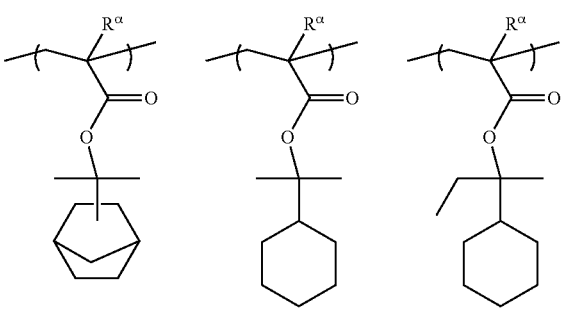
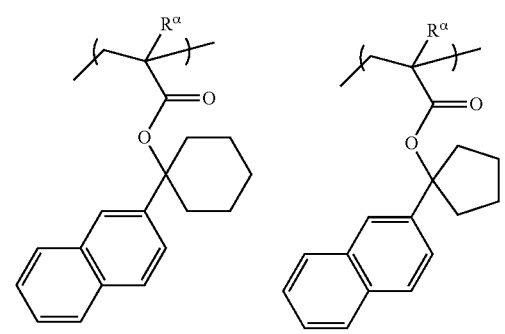
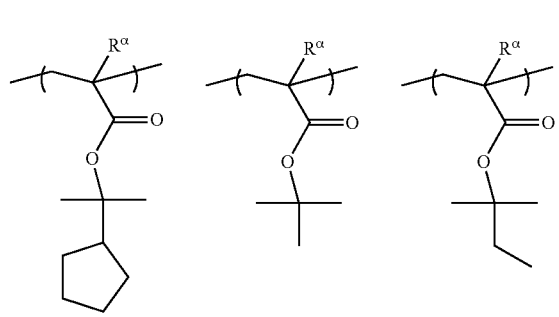

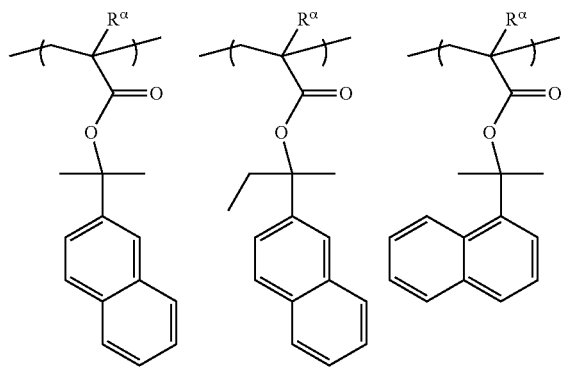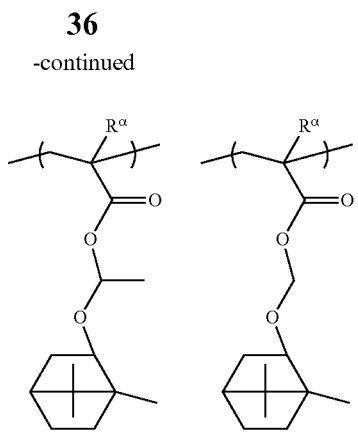
[Chemical Formula 23.]
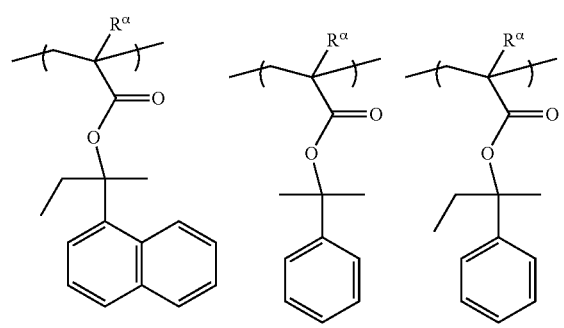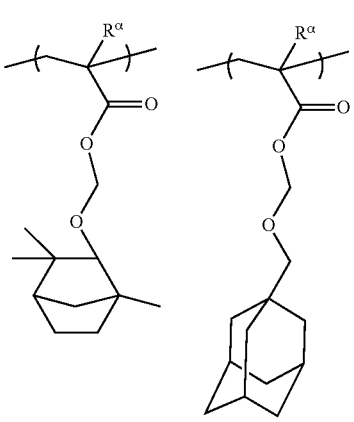
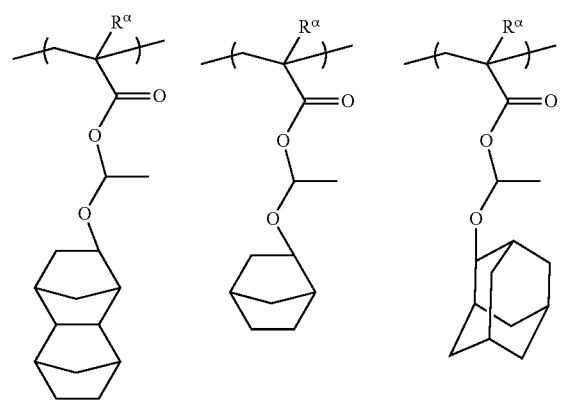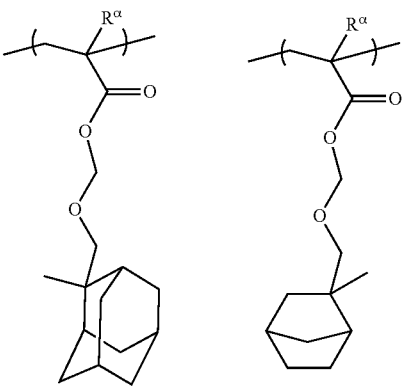
[Chemical Formula 24.]
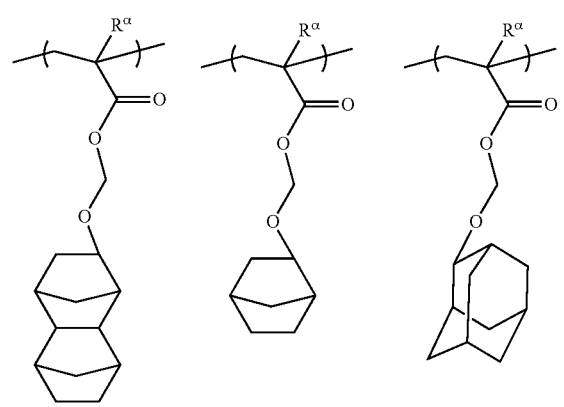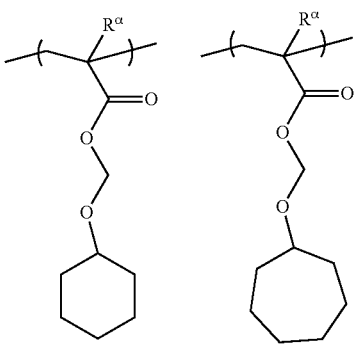

-continued
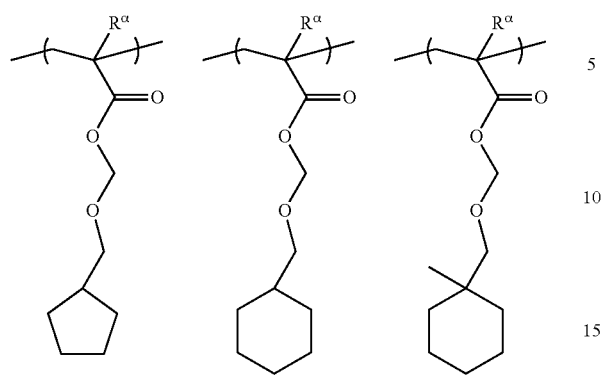
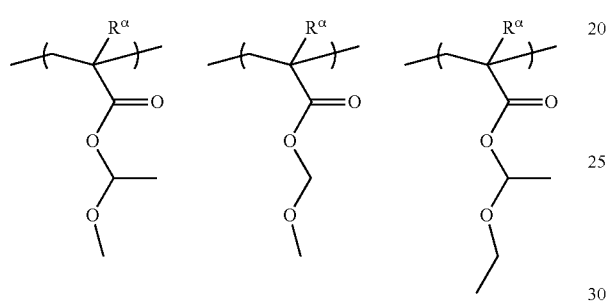
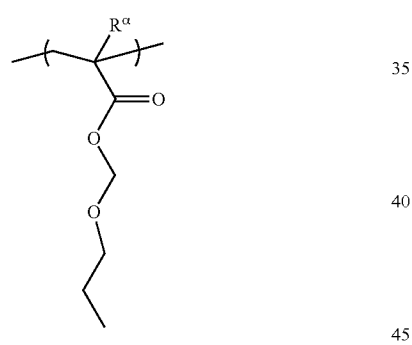
[Chemical Formula 25.]
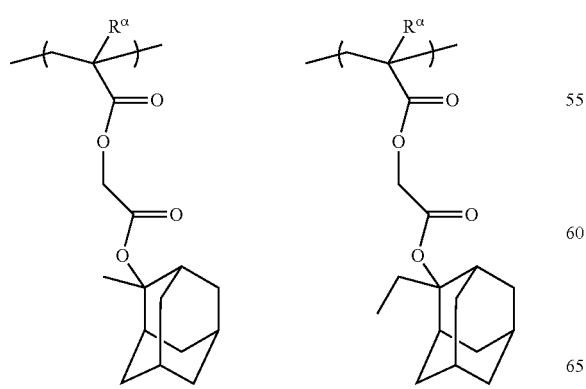
-continued
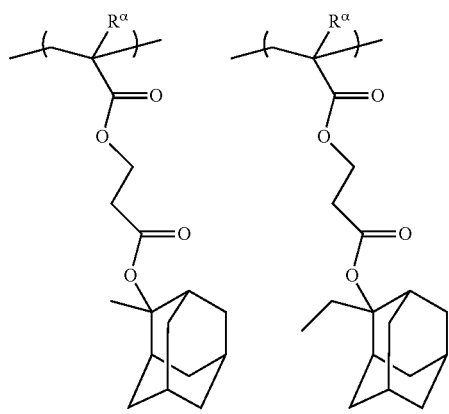
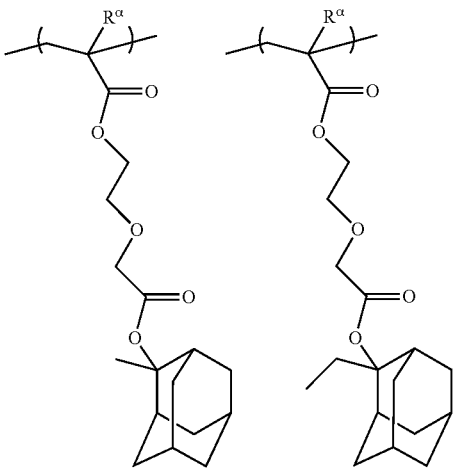
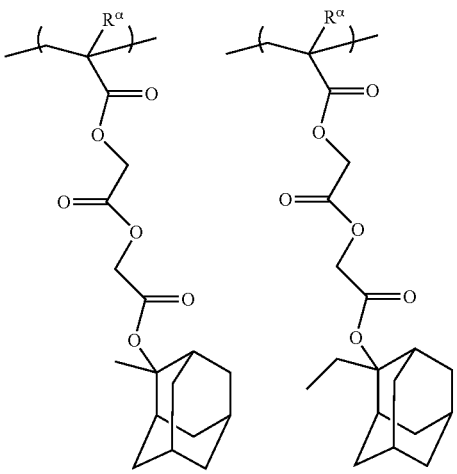
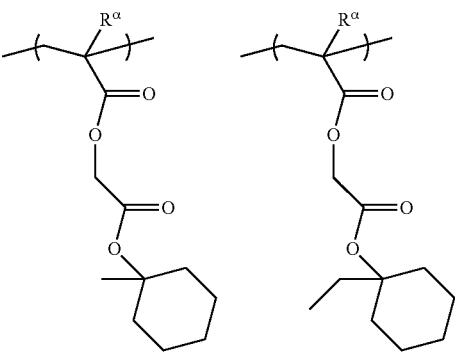

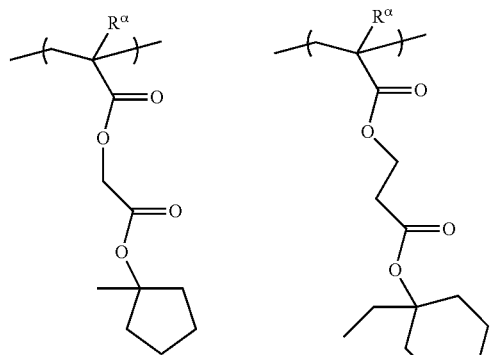
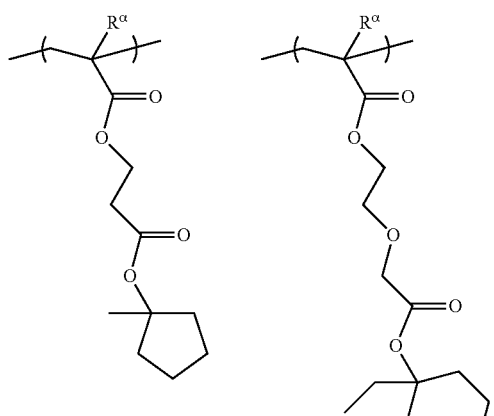
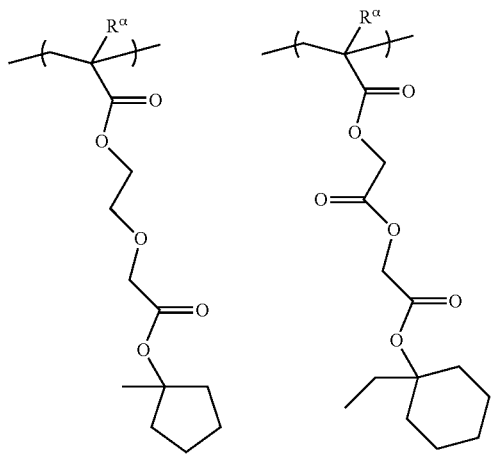
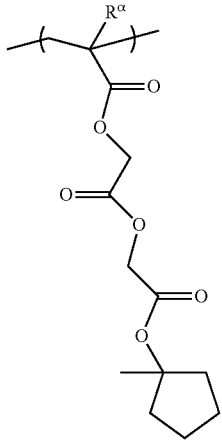
Specific examples of structural unit represented by formula (a1-2) are shown below.
[Chemical Formula 26.]
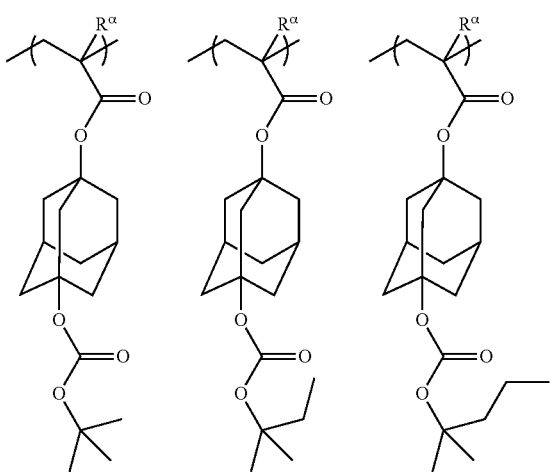
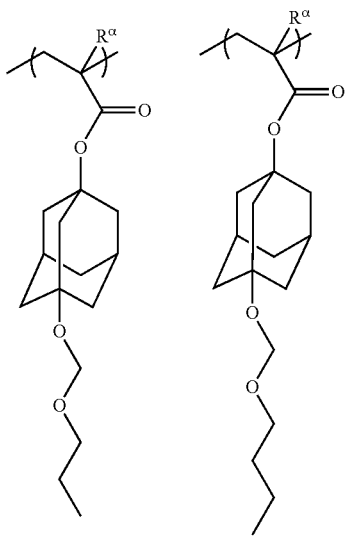

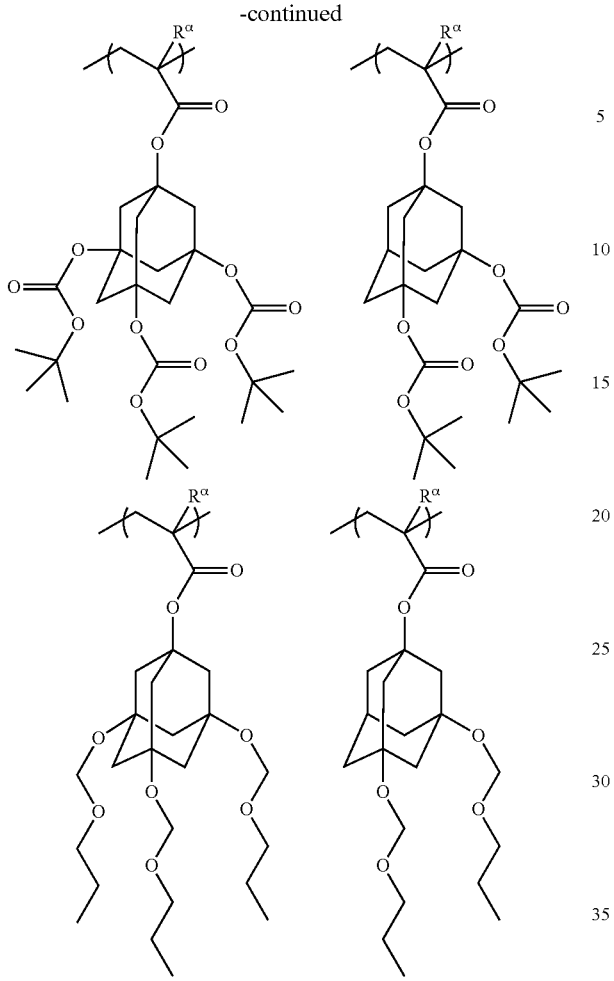

As the structural unit (a1) contained in the component (A1), 1 kind of structural unit may be used, or 2 or more kinds may be used.

From the viewpoint that the properties of the lithography (sensitivity, shape, and the like) by electron beam and EUV are more likely to be enhanced, the structural unit (a1) is further preferably a structural unit represented by general formula (a1-1).

Among these examples, as the structural unit (a1), a structural unit represented by general formula (a1-1-1) is particularly preferable.

[Chemical Formula 27.]

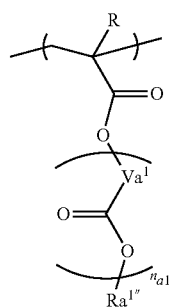

(a1-1-1)

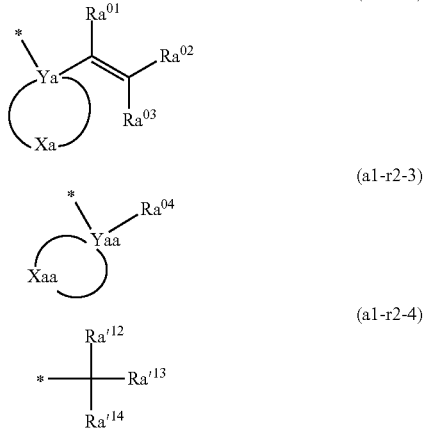

In the formula, $Ra^{1\prime\prime\prime}$ is an acid dissociable group represented by general formula (a1-r2-2), (a1-r2-3), or (a1-r2-4).

In general formula (a1-1-1), R, $Va^1$ and $n_{a1}$ are the same as defined for R, $Va^1$ and $n_{a1}$ in general formula (a1-1).

The description of the acid dissociable group represented by general formula (a1-r2-2), (a1-r2-3), or (a1-r2-4) is the same as described above.

In the component (A1), the amount of the structural unit (a1) based on the combined total (100 mol %) of all structural units constituting the component (A1) is preferably 30 mol % or more, more preferably 40 mol % or more, and still more preferably 50 mol % or more. The upper limit of the amount of the structural unit (a1) is not particularly limited, but is preferably 70 mol % or less, more preferably 65 mol % or less, and still more preferably 60 mol % or less.

When the amount of the structural unit (a1) is at least as large as the lower limit of the above-mentioned range, a resist pattern can be reliably obtained, and various lithography properties such as resolution and roughness are further improved. On the other hand, when the amount of the structural unit (a1) is no more than the upper limit of the above-mentioned range, a good balance can be achieved with the other structural units.

(Structural Unit (a10))

The component (A1) may include a structural unit (a10) represented by general formula (a10-1) shown below.

[Chemical Formula 28.]

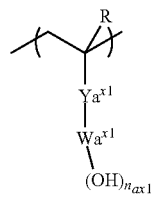

(a10-1)

In the formula, R represents a hydrogen atom, an alkyl group of 1 to 5 carbon atoms or a halogenated alkyl group of 1 to 5 carbon atoms; $Ya^{x1}$ represents a single bond or a divalent linking group; $Wa^{x1}$ represents an aromatic hydrocarbon group having a valency of ($na_{x1}$+1), optionally having a substituent; and $na_{x1}$ represents an integer of 1 to 3.

In the aforementioned formula (a10-1), as the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In general formula (a10-1), the divalent linking group for $Ya^{x1}$ is the same as defined for the divalent linking group for $Ya^{21}$ in the aforementioned general formula (a2-1). $Ya^{x1}$ is preferably a single bond.

Examples of the aromatic hydrocarbon group for $Wa^{x1}$ include a group obtained by removing $(n_{ax1}+1)$hydrogen atoms from an aromatic ring. The aromatic ring is not particularly limited, as long as it is a cyclic conjugated compound having $(4n+2)\pi$ electrons, and may be either monocyclic or polycyclic. The aromatic ring preferably has 5 to 30 carbon atoms, more preferably 5 to 20, still more preferably 6 to 15, and most preferably 6 to 12. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

In formula (a10-1), $n_{ax1}$ is an integer of 1 to 3, preferably 1 or 2, and more preferably 1.

Specific examples of structural unit represented by formula (a10-1) are shown below. In the following formulae, $R^{\alpha}$ represents a hydrogen atom, a methyl group or a trifluoromethyl group.

[Chemical Formula 29.]

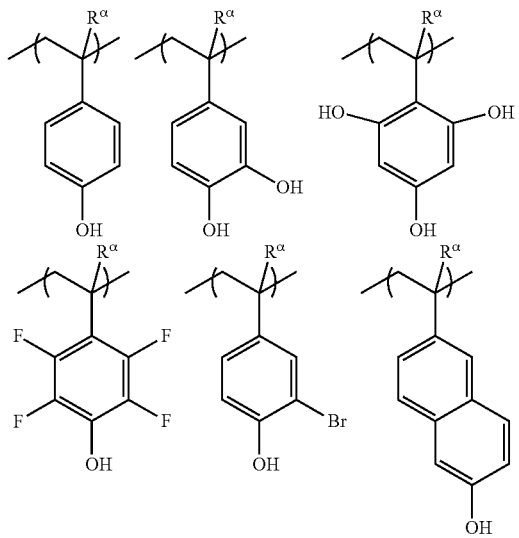

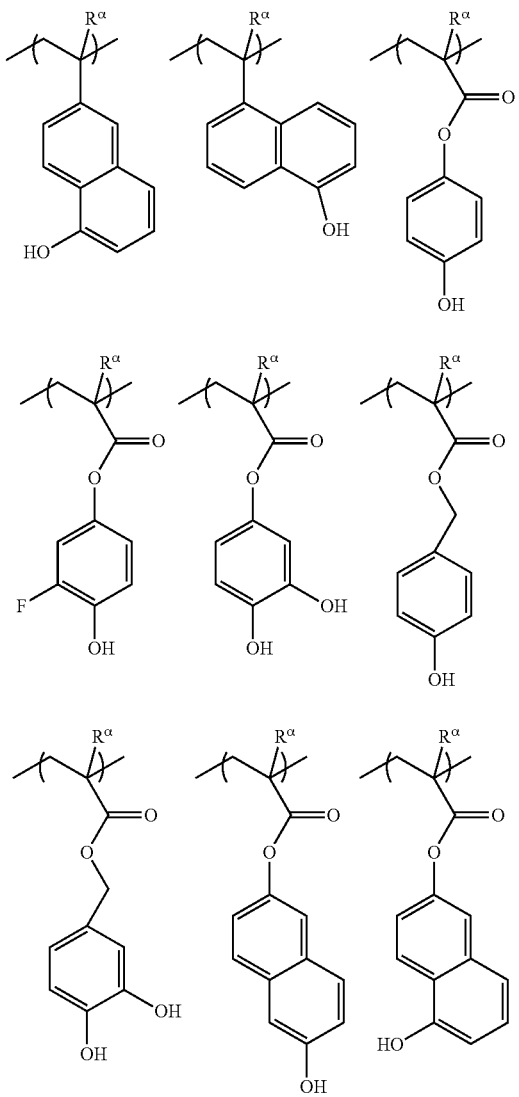

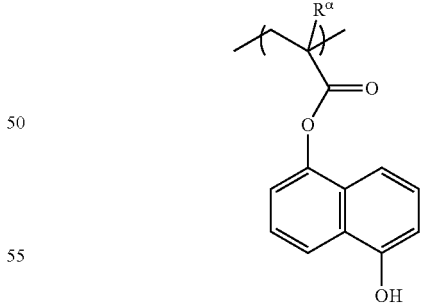

As the structural unit (a10) contained in the component (A1), 1 kind of structural unit may be used, or 2 or more kinds may be used.

Among these examples, the structural unit (a10) is preferably a structural unit containing a hydroxystyrene skeleton, and for example, a structural unit represented by general formula (a10-1-1) is particularly preferable.

[Chemical Formula 30.]

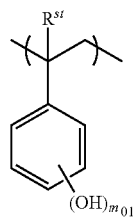

(a10-1-1)

In the formula, $R^{st}$ represents a hydrogen atom or a methyl group; and $m_{01}$ represents an integer of 1 to 3.

When the component (A1) includes the structural unit (a10), the amount of the structural unit (a10) based on the combined total (100 mol %) of all structural units constituting the component (A1) is preferably 10 mol % or more, and more preferably 20 mol % or more. The upper limit of the amount of the structural unit (a10) is not particularly limited, but is preferably 70 mol % or less, more preferably 65 mol % or less, and still more preferably 60 mol % or less.

When the amount of the structural unit (a10) is at least as large as the lower limit of the above-mentioned range, various lithography properties such as sensitivity, resolution and EL margin are improved. On the other hand, when the amount of the structural unit (a10) is no more than the upper limit of the above-mentioned range, a good balance can be reliably achieved with the other structural units.

(Structural Unit (a2))

The component (A1) may further include a structural unit (a2) which contains a lactone-containing cyclic group, an —$SO_2$— containing cyclic group or a carbonate-containing cyclic group (provided that structural units which fall under the definition of the structural unit (a1) are excluded).

When the component (A1) is used for forming a resist film, the lactone-containing cyclic group, the —$SO_2$— containing cyclic group or the carbonate-containing cyclic group within the structural unit (a2) is effective in improving the adhesion between the resist film and the substrate. Further, by virtue of including the structural unit (a2), in an alkali developing process, during developing, the solubility of the resist film in an alkali developing is enhanced.

The term "lactone-containing cyclic group" refers to a cyclic group including a ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for the structural unit (a2) is not particularly limited, and an arbitrary structural unit may be used. Specific examples include groups represented by general formulae (a2-r-1) to (a2-r-7) shown below.

[Chemical Formula 31.]

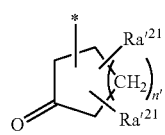

(a2-r-1)

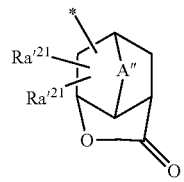

(a2-r-2)

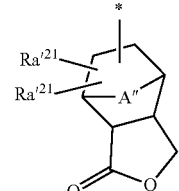

(a2-r-3)

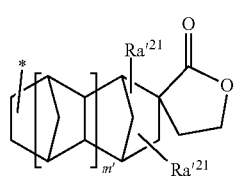

(a2-r-4)

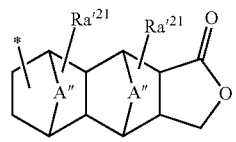

(a2-r-5)

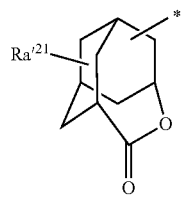

(a2-r-6)

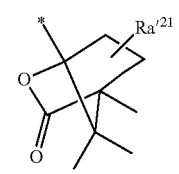

(a2-r-7)

In the formulae, each $Ra'^{21}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —$SO_2$— containing cyclic group; A" represents an oxygen atom (—O—), a sulfur atom (—S—) or an alkylene group of 1 to 5 carbon atoms which may contain an oxygen atom or a sulfur atom; n' represents an integer of 0 to 2; and m' represents 0 or 1.

In formulae (a2-r-1) to (a2-r-7), the alkyl group for $Ra'^{21}$ is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

The alkoxy group for Ra'$^{21}$ is preferably an alkoxy group of 1 to 6 carbon atoms.

Further, the alkoxy group is preferably a linear or branched alkoxy group. Specific examples of the alkoxy groups include the aforementioned alkyl groups for Ra'$^{21}$ having an oxygen atom (—O—) bonded thereto.

As examples of the halogen atom for Ra'$^{21}$, a fluorine atom, chlorine atom, bromine atom and iodine atom can be given. Among these, a fluorine atom is preferable.

Examples of the halogenated alkyl group for Ra'$^{21}$ include groups in which part or all of the hydrogen atoms within the aforementioned alkyl group for Ra'$^{21}$ has been substituted with the aforementioned halogen atoms. As the halogenated alkyl group, a fluorinated alkyl group is preferable, and a perfluoroalkyl group is particularly desirable.

With respect to —COOR" and —OC(=O)R" for Ra'$^{21}$, R" represents a hydrogen atom, an alkyl group, a lactone-containing cyclic group, a carbonate-containing cyclic group or an —SO$_2$— containing cyclic group.

The alkyl group for R" may be linear, branched or cyclic, and preferably has 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. Specific examples include groups in which one or more hydrogen atoms have been removed from a monocycloalkane or a polycycloalkane such as a bicycloalkane, tricycloalkane or tetracycloalkane which may or may not be substituted with a fluorine atom or a fluorinated alkyl group. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

Examples of the lactone-containing cyclic group for R" include groups represented by the aforementioned general formulae (a2-r-1) to (a2-r-7).

The carbonate-containing cyclic group for R" is the same as defined for the carbonate-containing cyclic group described later. Specific examples of the carbonate-containing cyclic group include groups represented by general formulae (ax3-r-1) to (ax3-r-3).

The —SO$_2$— containing cyclic group for R" is the same as defined for the —SO$_2$— containing cyclic group described later. Specific examples of the —SO$_2$— containing cyclic group include groups represented by general formulae (a5-r-1) to (a5-r-4).

The hydroxyalkyl group for Ra'$^{21}$ preferably has 1 to 6 carbon atoms, and specific examples thereof include the alkyl groups for Ra'$^{21}$ in which at least one hydrogen atom has been substituted with a hydroxy group.

In formulae (a2-r-2), (a2-r-3) and (a2-r-5), as the alkylene group of 1 to 5 carbon atoms represented by A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH$_2$—, —CH$_2$—O—CH$_2$—, —S—CH$_2$— and —CH$_2$—S—CH$_2$—. As A", an alkylene group of 1 to 5 carbon atoms or —O— is preferable, more preferably an alkylene group of 1 to 5 carbon atoms, and most preferably a methylene group.

Specific examples of the groups represented by the aforementioned general formulae (a2-r-1) to (a2-r-7) are shown below.

[Chemical Formula 32.]

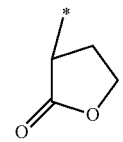 (r-lc-1-1)

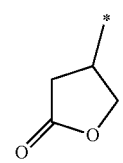 (r-lc-1-2)

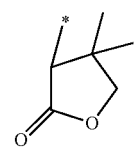 (r-lc-1-3)

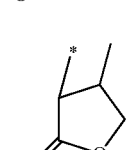 (r-lc-1-4)

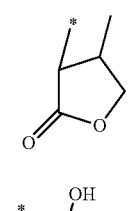 (r-lc-1-5)

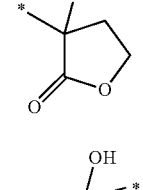 (r-lc-1-6)

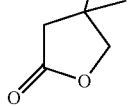 (r-lc-1-7)

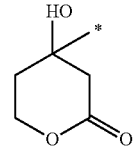

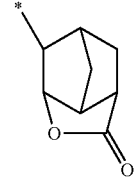 (r-lc-2-1)

(r-Ic-2-2)
(r-Ic-2-3)
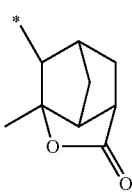
(r-Ic-2-4)
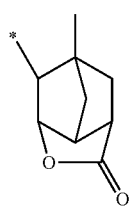
(r-Ic-2-5)
(r-Ic-2-6)
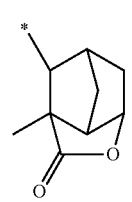
(r-Ic-2-7)
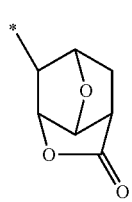
(r-Ic-2-8)
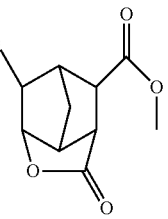
(r-Ic-2-9)
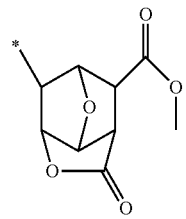
(r-Ic-2-10)
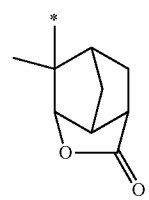
(r-Ic-2-11)
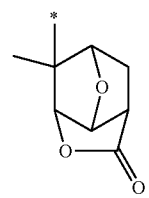
(r-Ic-2-12)
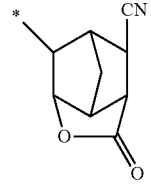
(r-Ic-2-13)
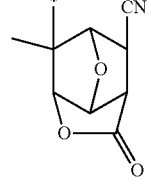
(r-Ic-2-14)
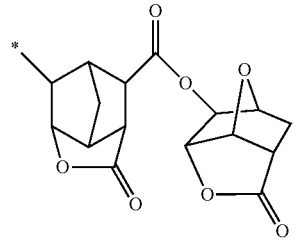
(r-Ic-2-15)
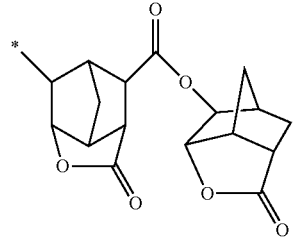

(r-Ic-2-16)
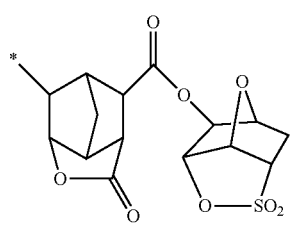
(r-Ic-2-17)
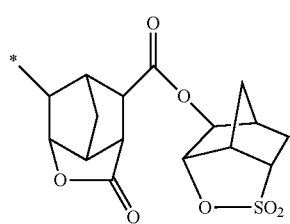
(r-Ic-2-18)
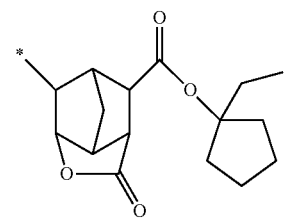
(r-Ic-3-1)
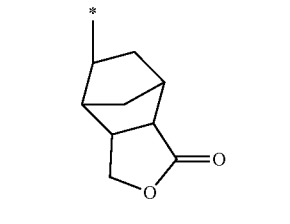
(r-Ic-3-2)
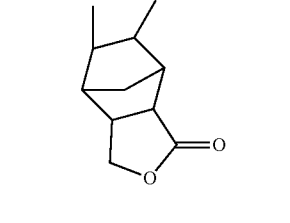
(r-Ic-3-3)
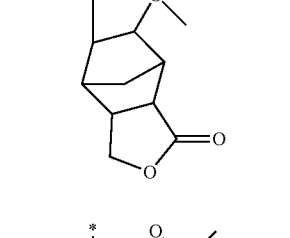
(r-Ic-3-4)
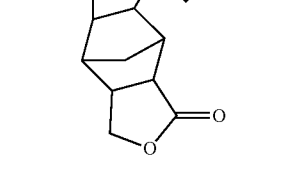
(r-Ic-3-5)
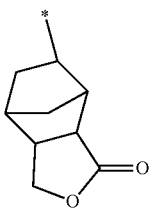
[Chemical Formula 33.]
(r-Ic-4-1)
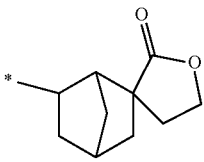
(r-Ic-4-2)
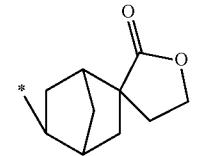
(r-Ic-4-3)
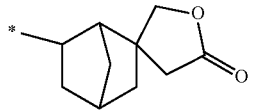
(r-Ic-4-4)
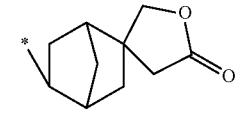
(r-Ic-4-5)
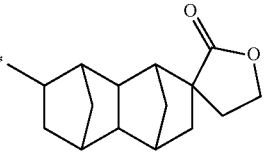
(r-Ic-4-6)
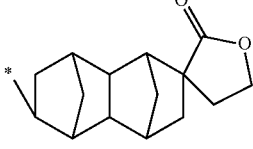
(r-Ic-4-7)
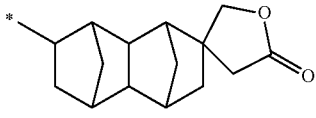
(r-Ic-4-8)
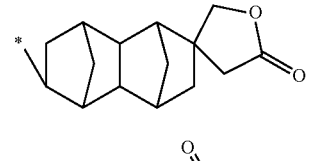
(r-Ic-4-9)
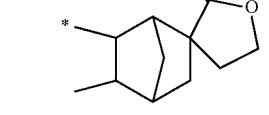

(r-Ic-5-1)
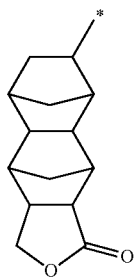

(r-Ic-5-2)
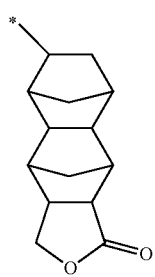

(r-Ic-5-3)
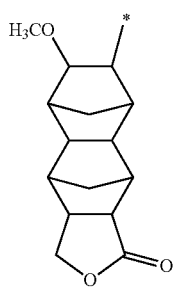

(r-Ic-5-4)
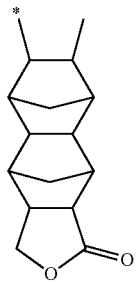

(r-Ic-6-1)
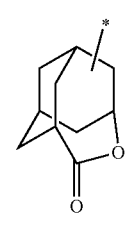

(r-Ic-7-1)
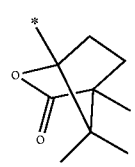

An "—$SO_2$— containing cyclic group" refers to a cyclic group having a ring containing —$SO_2$— within the ring structure thereof, i.e., a cyclic group in which the sulfur atom (S) within —$SO_2$— forms part of the ring skeleton of the cyclic group. The ring containing —$SO_2$— within the ring skeleton thereof is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings. The —$SO_2$— containing cyclic group may be either a monocyclic group or a polycyclic group.

As the —$SO_2$— containing cyclic group, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable.

More specific examples of the —$SO_2$— containing cyclic group include groups represented by general formulas (a5-r-1) to (a5-r-4) shown below.

[Chemical Formula 34.]

(a5-r-1)
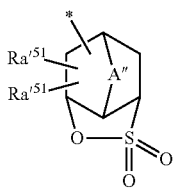

(a5-r-2)
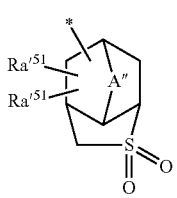

(a5-r-3)
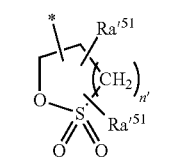

(a5-r-4)
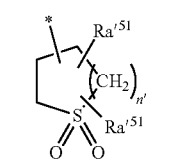

In the formulae, each $Ra'^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —$SO_2$— containing cyclic group; A" represents an oxygen atom, a sulfur atom or an alkylene group of 1 to 5 carbon atoms which may contain an oxygen atom or a sulfur atom; and n' represents an integer of 0 to 2.

In general formulae (a5-r-1) and (a5-r-2), A" is the same as defined for A" in general formulae (a2-r-2), (a2-r-3) and (a2-r-5).

Examples of the alkyl group, alkoxy group, halogen atom, halogenated alkyl group, —COOR", —OC(=O)R" and hydroxyalkyl group for $Ra'^{51}$ include the same groups as those described above in the explanation of $Ra'^{21}$ in the general formulas (a2-r-1) to (a2-r-7).
Specific examples of the groups represented by the aforementioned general formulae (a5-r-1) to (a5-r-4) are shown below. In the formulae shown below, "Ac" represents an acetyl group.
[Chemical Formula 35.]
(r-sl-1-1)
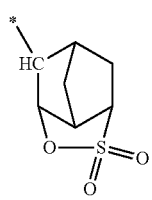
(r-sl-1-2)
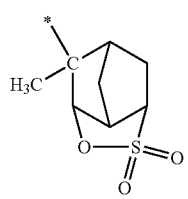
(r-sl-1-3)
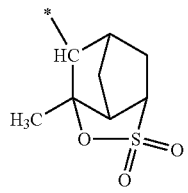
(r-sl-1-4)
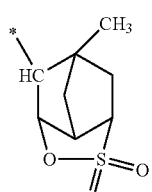
(r-sl-1-5)
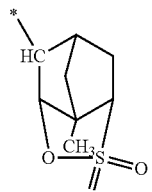
(r-sl-1-6)
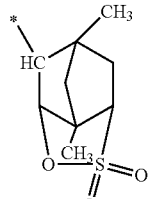
-continued
(r-sl-1-7)
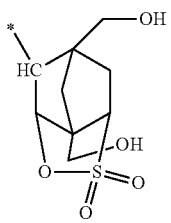
(r-sl-1-8)
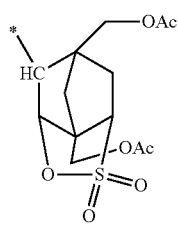
(r-sl-1-9)
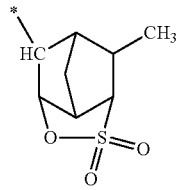
(r-sl-1-10)
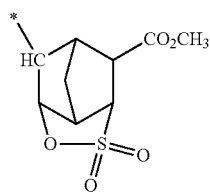
(r-sl-1-11)
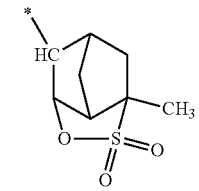
(r-sl-1-12)
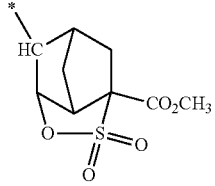
(r-sl-1-13)
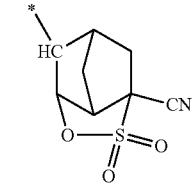

(r-sl-1-14)
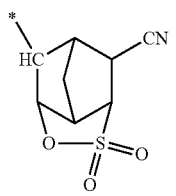
(r-sl-1-15)
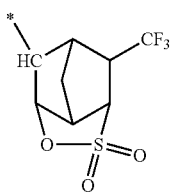
(r-sl-1-16)
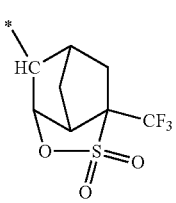
(r-sl-1-17)
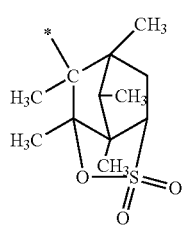
(r-sl-1-18)
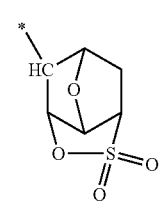
(r-sl-1-19)
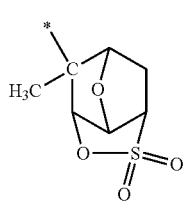
(r-sl-1-20)
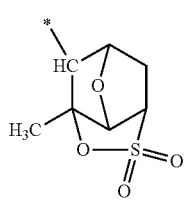
(r-sl-1-21)
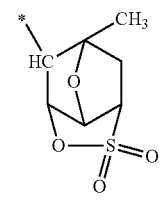
[Chemical Formula 36.]
(r-sl-1-22)
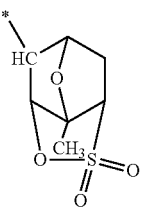
(r-sl-1-23)
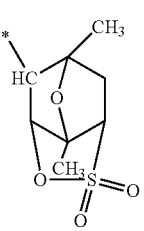
(r-sl-1-24)
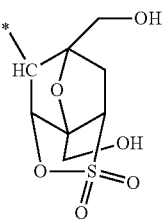
(r-sl-1-25)
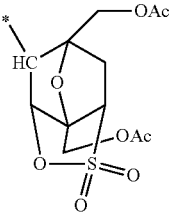
(r-sl-1-26)
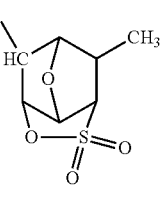
(r-sl-1-27)
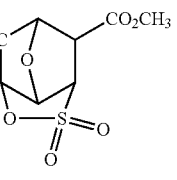
(r-sl-1-28)
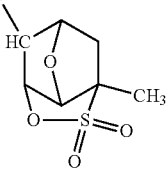

-continued (r-sl-1-29)
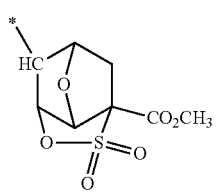

(r-sl-1-30)
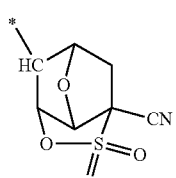

(r-sl-1-31)
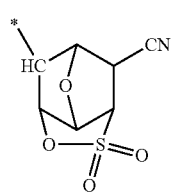

(r-sl-1-32)
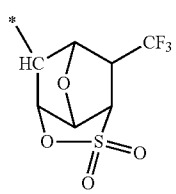

(r-sl-1-33)
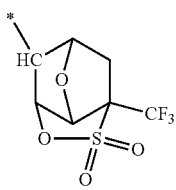

[Chemical Formula 37.]

(r-sl-2-1)
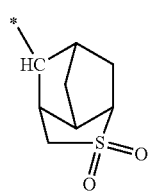

(r-sl-2-2)
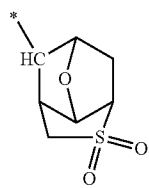

(r-sl-3-1)
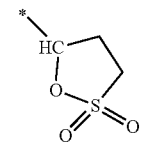

(r-sl-4-1)
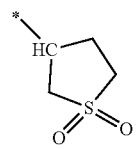

The term "carbonate-containing cyclic group" refers to a cyclic group including a ring containing a —O—C(═O)—O— structure (carbonate ring). The term "carbonate ring" refers to a single ring containing a —O—C(═O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group is not particularly limited, and an arbitrary group may be used. Specific examples include groups represented by general formulae (ax3-r-1) to (ax3-r-3) shown below.

[Chemical Formula 38.]

(ax3-r-1)
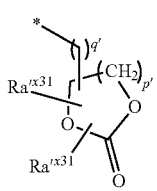

(ax3-r-2)
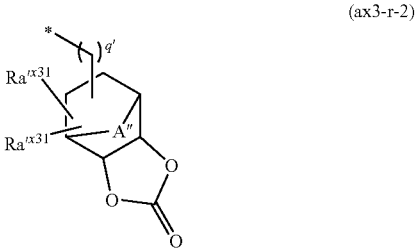

(ax3-r-3)
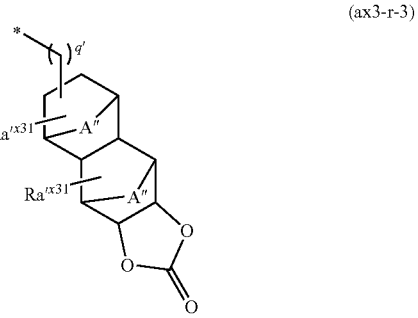

In the formulae, each $Ra'^{x31}$ independently represents a hydrogen atom, an alkyl group, an alkoxy group, a halogen atom, a halogenated alkyl group, a hydroxy group, —COOR″, —OC(═O)R″, a hydroxyalkyl group or a cyano group; R″ represents a hydrogen atom, an alkyl group, a lactone-containing cyclic group, a carbonate-containing cyclic group or an —$SO_2$— containing cyclic group; A″ represents an oxygen atom, a sulfur atom or an alkylene group of 1 to 5 carbon atoms which may contain an oxygen atom or a sulfur atom; p' represents an integer of 0 to 3; and q' represents 0 or 1.

In general formulae (ax3-r-2) and (ax3-r-3), A" is the same as defined for A" in general formulae (a2-r-2), (a2-r-3) and (a2-r-5).

Examples of the alkyl group, alkoxy group, halogen atom, halogenated alkyl group, —COOR", —OC(=O)R" and hydroxyalkyl group for $Ra'^{31}$ include the same groups as those described above in the explanation of $Ra'^{21}$ in the general formulas (a2-r-1) to (a2-r-7).

Specific examples of the groups represented by the aforementioned general formulae (ax3-r-1) to (ax3-r-3) are shown below.

[Chemical Formula 39.]

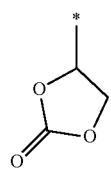 (r-cr-1-1)

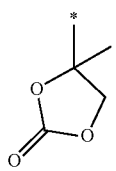 (r-cr-1-2)

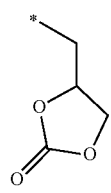 (r-cr-1-3)

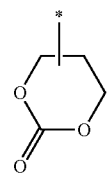 (r-cr-1-4)

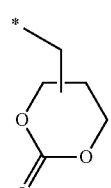 (r-cr-1-5)

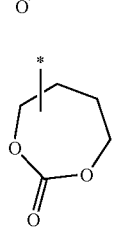 (r-cr-1-6)

-continued

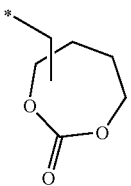 (r-cr-1-7)

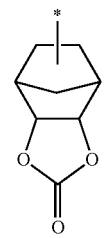 (r-cr-2-1)

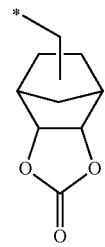 (r-cr-2-2)

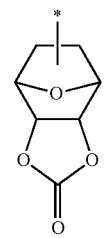 (r-cr-2-3)

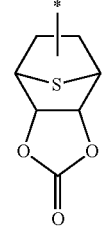 (r-cr-2-4)

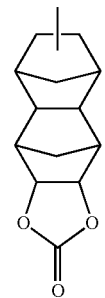 (r-cr-3-1)

(r-cr-3-2)
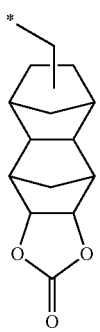

(r-cr-3-3)
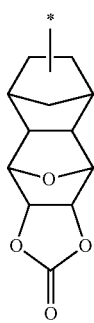

(r-cr-3-4)

(r-cr-3-5)
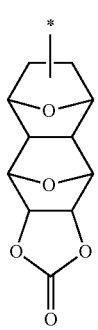

As the structural unit (a2), a structural unit derived from an acrylate ester which may have the hydrogen atom bonded to the carbon atom on the α-position substituted with a substituent is preferable.

The structural unit (a2) is preferably a structural unit represented by general formula (a2-1) shown below.

[Chemical Formula 40.]

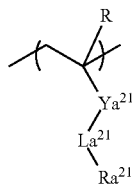
(a2-1)

In the formula, R represents a hydrogen atom, an alkyl group of 1 to 5 carbon atoms or a halogenated alkyl group of 1 to 5 carbon atoms; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group; provided that, when $La^{21}$ represents —O—, $Ya^{21}$ does not represents —CO—; and $Ra^{21}$ represents a lactone-containing cyclic group, a carbonate-containing cyclic group or an —$SO_2$— containing cyclic group.

In the formula (a2-1), R is the same as defined above.

The divalent linking group for $Ya^{21}$ is not particularly limited, and preferable examples thereof include a divalent hydrocarbon group which may have a substituent and a divalent linking group containing a hetero atom.

Divalent Hydrocarbon Group Which May Have a Substituent:

In the case where $Ya^{21}$ is a divalent linking group which may have a substituent, the hydrocarbon group may be either an aliphatic hydrocarbon group or an aromatic hydrocarbon group.

Aliphatic Hydrocarbon Group for $Ya^{21}$

The "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof can be given.

Linear or Branched Aliphatic Hydrocarbon Group

The linear aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched aliphatic hydrocarbon group preferably has 3 to 10 carbon atoms, more preferably 3 to 6 carbon atoms, still more preferably 3 or 4 carbon atoms, and most preferably 3 carbon atoms.

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)$ $CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group may or may not have a substituent. Examples of the substituent include a fluorine atom, a fluorinated alkyl group of 1 to 5 carbon atoms, and a carbonyl group.

Aliphatic Hydrocarbon Group Containing a Ring in the Structure Thereof

As examples of the hydrocarbon group containing a ring in the structure thereof, a cyclic aliphatic hydrocarbon group containing a hetero atom in the ring structure thereof and may have a substituent (a group in which two hydrogen atoms have been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic group is interposed within the aforementioned linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

Aromatic Hydrocarbon Group for Ya$^{21}$

The aromatic hydrocarbon group is a hydrocarbon group having at least one aromatic ring.

The aromatic ring is not particularly limited, as long as it is a cyclic conjugated compound having (4n+2) π electrons, and may be either monocyclic or polycyclic. The aromatic ring preferably has 5 to 30 carbon atoms, more preferably 5 to 20, still more preferably 6 to 15, and most preferably 6 to 12. Here, the number of carbon atoms within a substituent(s) is not included in the number of carbon atoms of the aromatic hydrocarbon group. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hetero ring include a pyridine ring and a thiophene ring.

Specific examples of the aromatic hydrocarbon group include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group). The alkylene group which is bonded to the aforementioned aryl group or heteroaryl group preferably has 1 to 4 carbon atoms, more preferably 1 or 2 carbon atoms, and most preferably 1 carbon atom.

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is particularly desirable.

As the alkoxy group, the halogen atom and the halogenated alkyl group for the substituent, the same groups as the aforementioned substituent groups for substituting a hydrogen atom within the cyclic aliphatic hydrocarbon group can be used.

Divalent Linking Group Containing a Hetero Atom

In the case where Ya$^{21}$ represents a divalent linking group containing a hetero atom, preferable examples of the linking group include —O—, —C(=O)—O—, —C(=O)—, —O—C(=O)—O—, —C(=O)—NH—, —NH—, —NH—C(=NH)— (may be substituted with a substituent such as an alkyl group, an acyl group or the like), —S—, —S(=O)$_2$—, —S(=O)$_2$—O—, and a group represented by general formula: —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$— or —Y$^{21}$—S(=O)$_2$—O—Y$^{22}$— [in the formulae, Y$^{21}$ and Y$^{22}$ each independently represents a divalent hydrocarbon group which may have a substituent, O represents an oxygen atom, and m' represents an integer of 0 to 3].

In the case where the divalent linking group containing a hetero atom is —C(=O)—NH—, —C(=O)—NH—C(=O)—, —NH— or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In general formulae —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$— or —$Y^{21}$—S(=O)$_2$—O—$Y^{22}$—, $Y^{21}$ and $Y^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m''}$—$Y^{22}$—, m'' represents an integer of 0 to 3, preferably an integer of 0 to 2, more preferably 0 or 1, and most preferably 1. Namely, it is particularly desirable that the group represented by the formula —[$Y^{21}$—C(=O)—O]$_{m''}$—$Y^{22}$— is a group represented by the formula —$Y^{21}$—C(=O)—O—$Y^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

$Ya^{21}$ preferably represents an ester bond [—C(=O)—O—], an ether bond (—O—), a linear or branched alkylene group, a combination of these, or a single bond.

In the formula (a2-1), $Ra^{21}$ represents a lactone-containing cyclic group, an —SO$_2$— containing cyclic group or a carbonate-containing cyclic group.

Preferable examples of the lactone-containing cyclic group, the —SO$_2$— containing cyclic group and the carbonate-containing cyclic group for $Ra^{21}$ include groups represented by general formulae (a2-r-1) to (a2-r-7), groups represented by general formulae (a5-r-1) to (a5-r-4) and groups represented by general formulae (ax3-r-1) to (ax3-r-3).

Among the above examples, a lactone-containing cyclic group or a —SO$_2$— containing cyclic group is preferable, and a group represented by general formula (a2-r-1), (a2-r-2), (a2-r-6) or (a5-r-1) is more preferable. Specifically, a group represented by any of chemical formulae (r-lc-1-1) to (r-lc-1-7), (r-lc-2-1) to (r-lc-2-18), (r-lc-6-1), (r-sl-1-1) and (r-sl-1-18) is still more preferable.

As the structural unit (a2) contained in the component (A1), 1 kind of structural unit may be used, or 2 or more kinds may be used.

When the component (A1) contains the structural unit (a2), the amount of the structural unit (a2) based on the combined total (100 mol %) of all structural units constituting the component (A1) is preferably 1 to 80 mol %, more preferably 10 to 70 mol %, still more preferably 10 to 65 mol %, and most preferably 10 to 60 mol %.

When the amount of the structural unit (a2) is at least as large as the lower limit of the above preferable range, the effect of using the structural unit (a2) can be satisfactorily achieved. On the other hand, when the amount of the structural unit (a2) is no more than the upper limit of the above preferable range, a good balance can be achieved with the other structural units, and various lithography properties and pattern shape can be improved.

(Structural Unit (a3))

The structural unit (a3) is a structural unit containing a polar group-containing aliphatic hydrocarbon group (provided that the structural units that fall under the definition of structural units (a1) and (a2) are excluded).

When the component (A1) includes the structural unit (a3), it is presumed that the hydrophilicity of the component (A1) is enhanced, thereby contributing to improvement in resolution.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 41.]

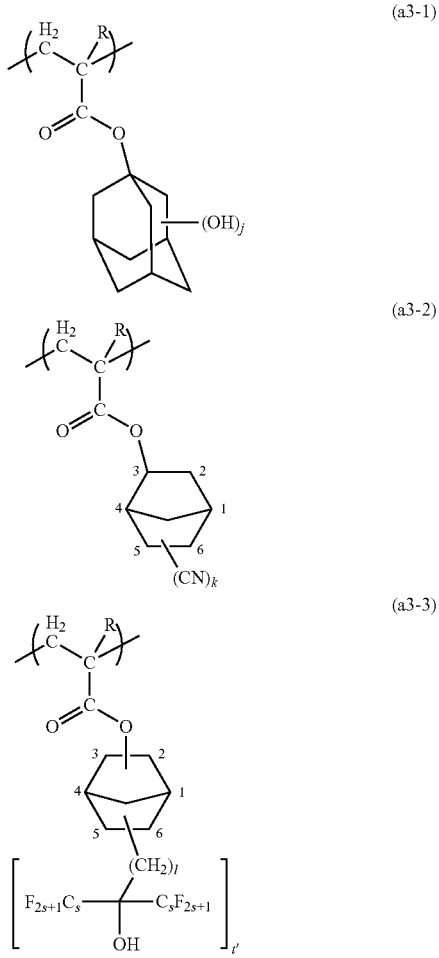

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A), 1 kind of structural unit may be used, or 2 or more kinds may be used.

When the component (A1) includes the structural unit (a3), the amount of the structural unit (a3) based on the combined total (100 mol %) of all structural units constituting the component (A1) is preferably 5 to 50 mol %, more preferably 5 to 40 mol %, and still more preferably 5 to 25 mol %.

When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

<<Other Structural Units>>

The component (A1) may be further include a structural unit other than the structural units (a10), (a1), (a2) and (a3).

Examples of the other structural units include a structural unit derived from styrene (provided that structural units which fall under the definition of the structural unit (a10) are excluded), a structural unit (a9) represented by general formula (a9-1) shown below, and a structural unit containing an acid non-dissociable aliphatic polycyclic group.

(Structural Unit (a9))

The structural unit (a9) is represented by general formula (a9-1) shown below.

[Chemical Formula 42.]

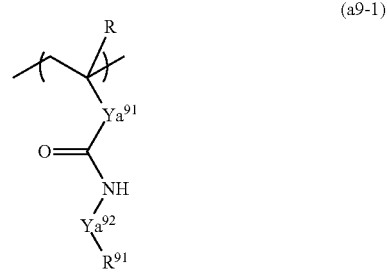

In the formula, R represents a hydrogen atom, an alkyl group of 1 to 5 carbon atoms or a halogenated alkyl group of 1 to 5 carbon atoms; $Ya^{91}$ represents a single bond or a divalent linking group; $Ya^{92}$ represents a divalent linking group; and $R^{91}$ represents a hydrocarbon group which may have a substituent.

In the general formula (a9-1), R is the same as defined above.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In general formula (a9-1), the divalent linking group for $Ya^{91}$ is the same as defined for the divalent linking group for $Ya^{21}$ in the aforementioned general formula (a2-1). $Ya^{91}$ is preferably a single bond.

In general formula (a9-1), the divalent linking group for $Ya^{92}$ is the same as defined for the divalent linking group for $Ya^{21}$ in the aforementioned general formula (a2-1).

With respect to the divalent linking group for $Ya^{92}$, as the divalent hydrocarbon group which may have a substituent, a linear or branched aliphatic hydrocarbon group is preferable.

The linear aliphatic hydrocarbon group preferably has 1 to 10 carbon atoms, more preferably 1 to 6, still more preferably 1 to 4, and most preferably 1 to 3. As the linear aliphatic hydrocarbon group, a linear alkylene group is preferable. Specific examples thereof include a methylene group [—CH$_2$—], an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

The branched aliphatic hydrocarbon group preferably has 3 to 10 carbon atoms, more preferably 3 to 6 carbon atoms, still more preferably 3 or 4 carbon atoms, and most preferably 3 carbon atoms. As the branched aliphatic hydrocarbon group, branched alkylene groups are preferred, and specific examples include various alkylalkylene groups, including alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. As the alkyl group within the alkylalkylene group, a linear alkyl group of 1 to 5 carbon atoms is preferable.

In the case where Ya$^{92}$ represents a divalent linking group containing a hetero atom, examples of the linking group include —O—, —C(=O)—O—, —C(=O)—, —C(=O)—NH—, —NH—, —NH—C(=NH)— (wherein H may be substituted with a substituent such as an alkyl group or an acyl group), —S—, —S(=O)$_2$—, —S(=O)$_2$—, C(=S), a group represented by general formula —Y$^{21}$—O—Y$^{22}$, —Y$^{21}$—O—, —Y$^{21}$—C(=O)—O—, —C(=O)—O—Y$^{21}$, —[Y$^{21}$—C(=O)—O]$_{m'}$—Y$^{22}$— or —Y$^{21}$—O—C(=O)—Y$^{22}$— [in the formulae, Y$^{21}$ and Y$^{22}$ each independently represents a divalent hydrocarbon group which may have a substituent, and O represents an oxygen atom; and m' represents an integer of 0 to 3. Among these examples, —C(=O)— and —C(=S)— are preferable.

In general formula (a9-1), examples of the hydrocarbon group for R$^{91}$ include an alkyl group, a monovalent alicyclic hydrocarbon group, an aryl group and an aralkyl group.

The alkyl group for R$^{91}$ preferably has 1 to 8 carbon atoms, more preferably 1 to 6 carbon atoms, and still more preferably 1 to 4 carbon atoms. The alkyl group may be linear or branched. Specific examples of preferable alkyl groups include a methyl group, an ethyl group, a propyl group, a butyl group, a hexyl group and an octyl group.

The monovalent alicyclic hydrocarbon group for R$^{91}$ preferably has 3 to 20 carbon atoms, and more preferably 3 to 12 carbon atoms. The monovalent alicyclic hydrocarbon group may be polycyclic or monocyclic. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclobutane, cyclopentane and cyclohexane. As the polycyclic alicyclic hydrocarbon group, a group in which one or more hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aryl group for R$^{91}$ preferably has 6 to 18 carbon atoms, and more preferably 6 to 10 carbon atoms. Specifically, a phenyl group is particularly desirable.

As the aralkyl group for R$^{91}$, an aralkyl group in which an alkylene group having 1 to 8 carbon atoms has been bonded to the aforementioned "aryl group for R$^{91}$" is preferable, an aralkyl group in which an alkylene group of 1 to 6 carbon atoms has been bonded to the aforementioned "aryl group for R$^{91}$" is more preferable, and an aralkyl group in which an alkylene group having 1 to 4 carbon atoms has been bonded to the aforementioned "aryl group for R$^{91}$" is most preferable.

The hydrocarbon group for R$^{91}$ preferably has part or all of the hydrogen atoms within the hydrocarbon group substituted with fluorine, and the hydrocarbon group more preferably has 30 to 100% of the hydrogen atoms substituted with fluorine. Among these, a perfluoroalkyl group in which all of the hydrogen atoms within the alkyl group have been substituted with fluorine atoms is particularly desirable.

The hydrocarbon group for R$^{91}$ may have a substituent. Examples of the substituent include a halogen atom, an oxo group (=O), a hydroxy group (—OH), an amino group (—NH$_2$) and —SO$_2$—NH$_2$. Further, part of the carbon atoms constituting the hydrocarbon group may be substituted with a substituent containing a hetero atom. Examples of the substituent containing a hetero atom include —O—, —NH—, —N=, —C(=O)—O—, —S—, —S(=O)$_2$— and —S(=O)$_2$—O—.

As the hydrocarbon group for R$^{91}$, examples of the hydrocarbon group having a substituent include lactone-containing cyclic groups represented by the aforementioned general formulae (a2-r-1) to (a2-r-7).

Further, as R$^{91}$, examples of the hydrocarbon group having a substituent include —SO$_2$— containing cyclic groups represented by general formulae (a5-r-1) to (a5-r-4); and substituted aryl groups and monocyclic heterocyclic groups represented by chemical formulae shown below.

[Chemical Formula 43.]

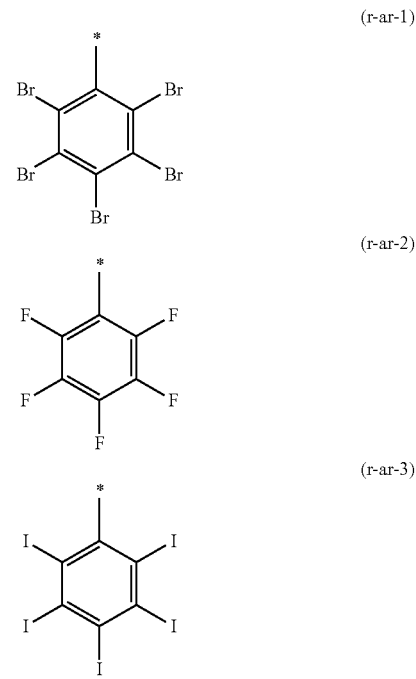

-continued
(r-ar-4)
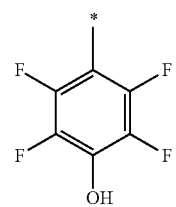
(r-ar-5)
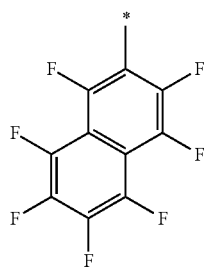
(r-ar-6)
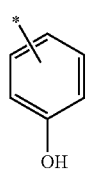
(r-ar-7)
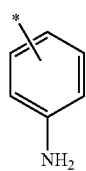
(r-ar-8)
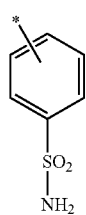
(r-hr-1)
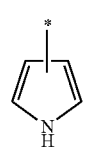
(r-hr-2)
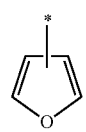
(r-hr-3)
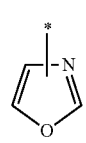
-continued
(r-hr-4)
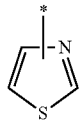
(r-hr-5)
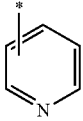
(r-hr-6)
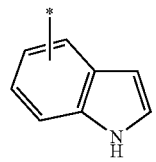
(r-hr-7)
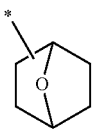
(r-hr-8)
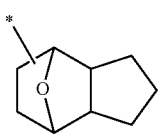
(r-hr-9)
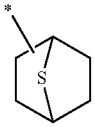
(r-hr-10)
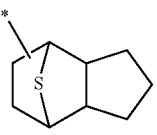
(r-hr-11)
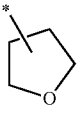
(r-hr-12)
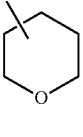
(r-hr-13)
(r-hr-14)

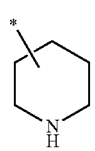
(r-hr-15)

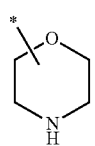
(r-hr-16)

As the structural unit (a9), a structural unit represented by general formula (a9-1-1) shown below is preferable.

[Chemical Formula 44.]

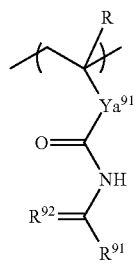
(a9-1-1)

In the formula, R is the same as defined above; $Ya^{91}$ represents a single bond or a divalent linking group; $R^{91}$ represents a hydrocarbon group optionally having a substituent; and $Ya^{92}$ represents an oxygen atom or a sulfur atom.

In general formula (a9-1-1), $Ya^{91}$, $R^{91}$ and R are the same as defined above.

$R^{92}$ represents an oxygen atom or a sulfur atom.

Specific examples of structural units represented by general formula (a9-1) or (a9-1-1) are shown below. In the following formulae, $R^\alpha$ represents a hydrogen atom, a methyl group or a trifluoromethyl group.

[Chemical Formula 45.]

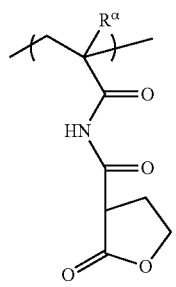 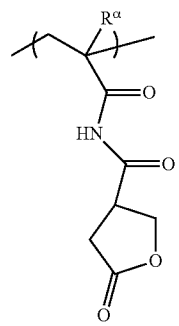 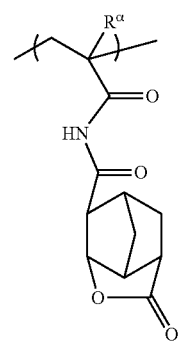

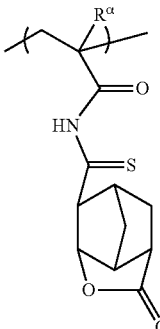 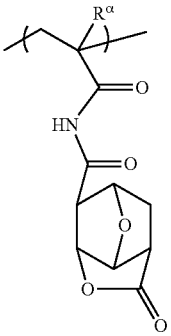

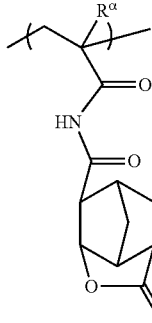 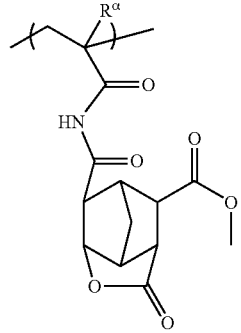

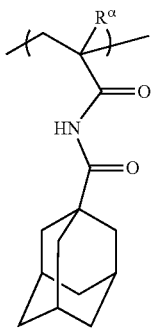 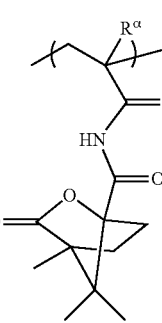 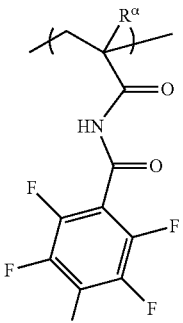

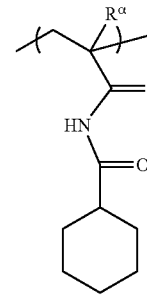 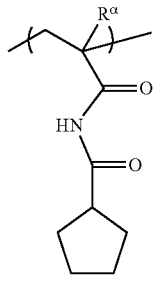 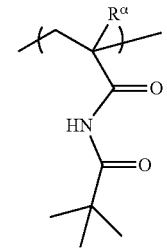

-continued

[Chemical Formula 46.]

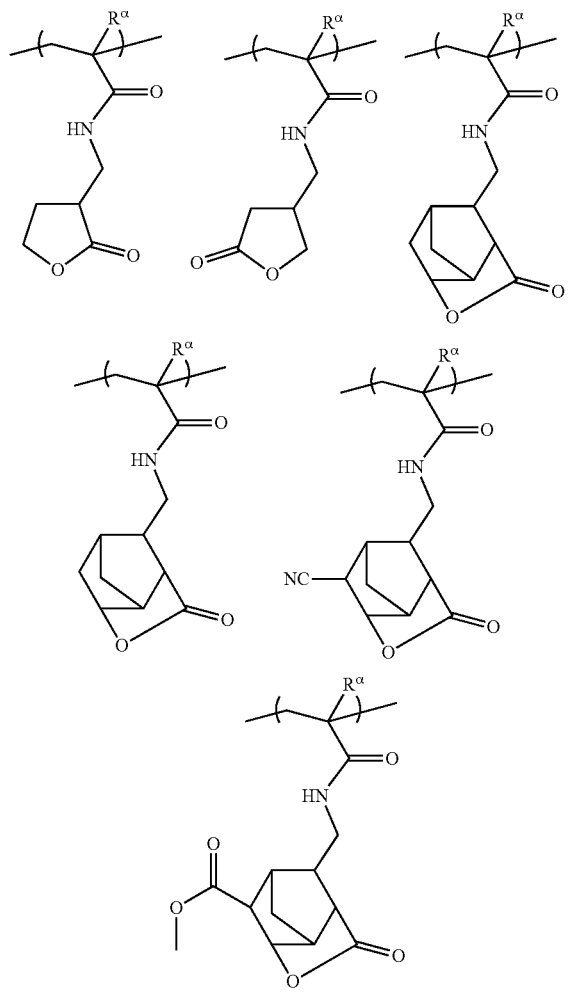

[Chemical Formula 47.]

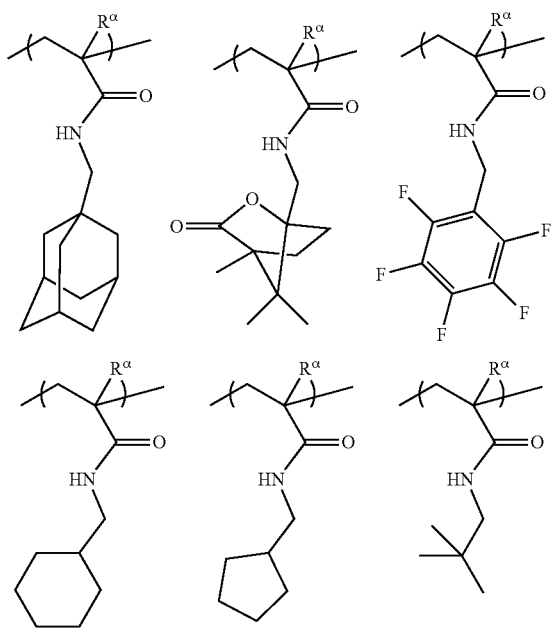

-continued

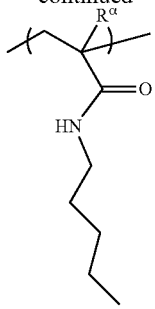

As the structural unit (a9) contained in the component (A1), 1 kind of structural unit may be used, or 2 or more kinds may be used. When the component (A1) includes the structural unit (a9), the amount of the structural unit (a9) based on the combined total (100 mol %) of all structural units constituting the component (A1) is preferably 1 to 40 mol %, more preferably 3 to 30 mol %, and still more preferably 10 to 30 mol %.

When the amount of the structural unit (a9) is at least as large as the lower limit of the above-mentioned range, various lithography properties such as development properties and EL margin are improved. On the other hand, when the amount of the structural unit (a9) is no more than the upper limit of the above-mentioned range, a good balance can be reliably achieved with the other structural units.

The component (A1) is preferably a copolymer having the structural unit (a1), the structural unit (a2) and the structural unit (a3), and more preferably a copolymer having the structural unit (a10), the structural unit (a1), the structural unit (a2) and the structural unit (a3).

The component (A) can be obtained, for example, by a conventional radical polymerization or the like of the monomers corresponding with each of the structural units, using a radical polymerization initiator such as azobisisobutyronitrile (AIBN) or dimethyl 2,2'-azobis(isobutyrate).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

In the present invention, the weight average molecular weight (Mw) (the polystyrene equivalent value determined by gel permeation chromatography) of the component (A) is not particularly limited, but is preferably 1,000 to 50,000, more preferably 1,500 to 30,000, and most preferably 2,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

In the resist composition of the present invention, as the component (A), one kind may be used, or two or more kinds of compounds may be used in combination.

In the resist composition of the present invention, the amount of the component (A) can be appropriately adjusted depending on the thickness of the resist film to be formed, and the like.

<<Fluorine Additive Component; Component (F)>>

The fluorine additive component (F) exhibits decomposability to an alkali developing solution, and includes a fluorine resin component (F1) (hereafter, sometimes referred to as "component (F1)") having a structural unit (f1) containing a base dissociable group and a structural unit (f2) containing a group represented by general formula (f2-r-1) shown below.

(Structural Unit (f1))

The structural unit (f1) is a structural unit having a base dissociable group.

In the present invention, the term "base dissociable group" refers to an organic group which can be dissociated from the structural unit (f1) by the action of a base.

Examples of the base include alkali developing solutions generally used in the fields of lithography. That is, the "base dissociable group" refers to a group which is dissociated by the action of an alkali developing solution (for example, a 2.38% by weight aqueous solution of tetramethylammonium hydroxide (TMAH) at 23° C.).

A base dissociable group dissociates due to hydrolysis caused by the action of an alkali developing solution.

Therefore, a hydrophilic group is formed when the base dissociable group is dissociated, and the hydrophilicity of the component (F) is enhanced, such that the affinity of the component (F) for the alkali developing solution is appropriately improved.

Specific examples of the base dissociable group include those represented by general formulas (II-1) to (II-5) shown below.

In the present invention, the base dissociable group is preferably at least one base dissociable group selected from those represented by general formulas (II-1) to (II-5) shown below. In consideration of improvement in hydrophilicity during development, and ease in synthesis, a group represented by general formula (II-1), (II-4) or (II-5) shown below is particularly desirable.

[Chemical Formula 48.]

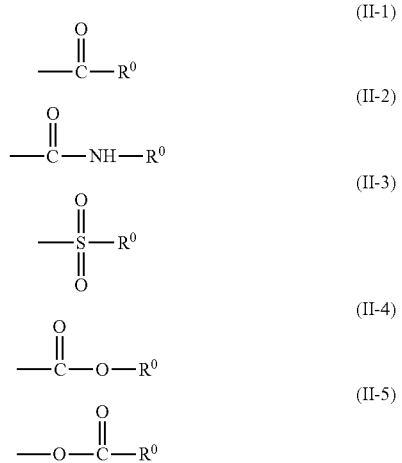

In the formulas, each $R^0$ independently represents an organic group which may have a fluorine atom.

In general formulas (II-1) to (II-5), each $R^0$ independently represents an organic group which may have a fluorine atom.

An "organic group" is a group containing at least one carbon atom.

The structure of $R^0$ may be linear, branched or cyclic, and is preferably linear or branched.

In $R^0$, the organic group preferably has 1 to 20 carbon atoms, more preferably 1 to 15 carbon atoms, still more preferably 1 to 10 carbon atoms, and most preferably 1 to 5 carbon atoms.

The fluorination ratio of $R^0$ preferably 25% or more, more preferably 50% or more, and most preferably 60% or more.

The term "fluorination ratio" refers to the percentage (%) of the number of fluorine atoms based on the total number of hydrogen atoms and fluorine atoms contained within the organic group.

As a preferable example of $R^0$, a fluorinated hydrocarbon group which may or may not have a substituent such as a methyl group or an ethyl group can be given.

With respect to the fluorinated hydrocarbon group for $R^0$ which may have a substituent, the hydrocarbon group may be either an aliphatic hydrocarbon group or an aromatic hydrocarbon group, and an aliphatic hydrocarbon group is preferable.

An aliphatic hydrocarbon group refers to a hydrocarbon group having no aromaticity. The aliphatic hydrocarbon group may be either saturated or unsaturated, but in general, the aliphatic hydrocarbon group is preferably saturated.

As $R^0$, a fluorinated, saturated hydrocarbon group or a fluorinated, unsaturated hydrocarbon group is preferable, more preferably a fluorinated, saturated hydrocarbon group, and most preferably a fluorinated alkyl group.

Examples of fluorinated alkyl groups include groups in which part or all of the hydrogen atoms within the below described unsubstituted alkyl groups have been substituted with a fluorine atom. The fluorinated alkyl group may be either a group in which part of the hydrogen atoms within an unsubstituted alkyl group described below has been substituted with a fluorine atom, or a group in which all of the hydrogen atoms within an unsubstituted alkyl group described below has been substituted with a fluorine atom (i.e., a perfluoroalkyl group).

The unsubstituted alkyl group may be linear, branched or cyclic. Alternatively, the unsubstituted alkyl group may be a combination of a linear or branched alkyl group with a cyclic alkyl group.

The unsubstituted linear alkyl group preferably has 1 to 10 carbon atoms, and more preferably 1 to 8. Specific examples include a methyl group, an ethyl group, an n-propyl group, an n-butyl group, an n-pentyl group, an n-hexyl group, an n-heptyl group, an n-octyl group, an n-nonyl group and an n-decyl group.

The unsubstituted branched alkyl group preferably has 3 to 10 carbon atoms, and more preferably 3 to 8. As the branched alkyl group, a tertiary alkyl group is preferable.

As an example of an unsubstituted cyclic alkyl group, a group in which one hydrogen atom has been removed from a monocycloalkane or a polycycloalkane such as a bicycloalkane, tricycloalkane or tetracycloalkane can be given. Specific examples include monocycloalkyl groups such as a cyclopentyl group and a cyclohexyl group; and polycycloalkyl groups such as an adamantyl group, a norbornyl group, an isobornyl group, a tricyclodecyl group and a tetracyclododecyl group.

Examples of the combination of a linear or branched alkyl group with a cyclic alkyl group include groups in which a cyclic alkyl group as a substituent is bonded to a linear or branched alkyl group, and groups in which a linear or branched alkyl group as a substituent is bonded to a cyclic alkyl group.

Examples of substituents for the fluorinated hydrocarbon group include an alkyl group of 1 to 5 carbon atoms.

As the fluorinated alkyl group for $R^0$, a linear or branched fluorinated alkyl group is preferable. In particular, a group represented by general formula (III-1) or (III-2) shown below is desirable, and a group represented by general formula (III-1) is most preferable.

[Chemical Formula 49.]

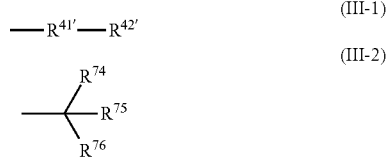

In general formula (III-1), $R^{41'}$ represents an unsubstituted alkylene group of 1 to 9 carbon atoms, and $R^{42'}$ represents a fluorinated alkyl group of 1 to 9 carbon atoms, provided that the total number of carbon atoms of $R^{41'}$ and $R^{42'}$ is no more than 10. In general formula (III-2), each of $R^{74}$ to $R^{76}$ independently represents a linear alkyl group of 1 to 5 carbon atoms, with the provision that at least one of $R^{74}$ to $R^{76}$ represents an alkyl group having a fluorine atom.

In general formula (III-1), the alkylene group for $R^{41'}$ may be linear, branched or cyclic, and is preferably linear or branched. Further, the number of carbon atoms within the alkylene group is preferably within a range of from 1 to 5.

As $R^{41'}$, a methylene group, an ethylene group or a propylene group is particularly desirable.

As $R^{42'}$, a linear or branched fluorinated alkyl group of 1 to 5 carbon atoms is preferable, and a perfluoroalkyl group is particularly desirable. Among perfluoroalkyl groups, a trifluoromethyl group ($—CF_3$), a tetrafluoroethyl group ($—C_2F_4H$) or $—C_2F_5$ is preferable.

In general formula (III-2), as the alkyl group for $R^{74}$ to $R^{76}$, an ethyl group or a methyl group is preferable, and a methyl group is particularly desirable. At least one of the alkyl groups for $R^{74}$ to $R^{76}$ is a fluorinated alkyl group, and all of the alkyl groups for $R^{74}$ to $R^{76}$ may be fluorinated alkyl groups.

In the present invention, the component (F1) preferably contains, as the structural unit (II), a structural unit represented by general formula (f1-1) shown below, or a structural unit represented by general formula (f1-2) shown below.

[Chemical Formula 50.]

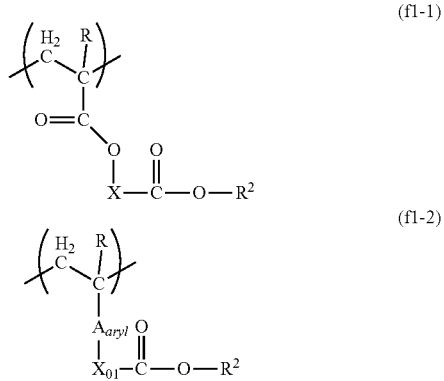

In the formula, each R independently represents a hydrogen atom, an alkyl group of 1 to 5 carbon atoms or a halogenated alkyl group of 1 to 5 carbon atoms; X represents a divalent linking group having no acid dissociable portion; $A_{aryl}$ represents a divalent aromatic cyclic group which may have a substituent; $X_{01}$ represents a single bond or a divalent linking group; and each $R^2$ independently represents an organic group having a fluorine atom.

In general formula (f1-1) and (f1-2), R is the same as defined above.

In general formula (f1-1), X represents a divalent linking group having no acid dissociable portion.

An "acid dissociable portion" refers to a portion within the organic group which is dissociated from the organic group by the action of acid generated upon exposure.

Examples of the divalent linking group having no acid dissociable portion for X include a divalent hydrocarbon group which may have a substituent, and a divalent group containing a hetero atom.

(Hydrocarbon Group which May have a Substituent)

With respect to the group other than the polymerizable group, the hydrocarbon group may "have a substituent" means that part or all of the hydrogen atoms of the hydrocarbon group may be substituted with groups or atoms other than hydrogen atoms.

The hydrocarbon group may be either an aliphatic hydrocarbon group or an aromatic hydrocarbon group.

An "aliphatic hydrocarbon group" refers to a hydrocarbon group that has no aromaticity. The aliphatic hydrocarbon group may be either saturated or unsaturated, but in general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 8, still more preferably 1 to 5, still more preferably 1 to 3, and most preferably 2.

As a linear aliphatic hydrocarbon group, a linear alkylene group is preferable, and specific examples include a methylene group, an ethylene group [$—(CH_2)_2—$], a trimethylene group [$—(CH_2)_3—$], a tetramethylene group [$—(CH_2)_4—$] and a pentamethylene group [$—(CH_2)_5—$].

As a branched aliphatic hydrocarbon group, a branched alkylene group is preferable, and specific examples include alkylmethylene groups such as $—CH(CH_3)—$, $—CH(CH_2CH_3)—$, $—C(CH_3)_2—$, $—C(CH_3)(CH_2CH_3)—$, $—C(CH_3)(CH_2CH_2CH_3)—$, and $—C(CH_2CH_3)_2—$; alkylethylene groups such as $—CH(CH_3)CH_2—$, $—CH(CH_3)CH(CH_3)—$, $—C(CH_3)_2CH_2—$, $—CH(CH_2CH_3)CH_2—$, and $—CH(CH_2CH_3)CH_2—$; alkyltrimethylene groups such as $—CH(CH_3)CH_2CH_2—$, and $—CH_2CH(CH_3)CH_2—$; and alkyltetramethylene groups such as $—CH(CH_3)CH_2CH_2CH_2—$, and $—CH_2CH(CH_3)CH_2CH_2—$. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated lower alkyl group of 1 to 5 carbon atoms, and an oxygen atom ($=O$).

As examples of the aliphatic hydrocarbon group containing a ring, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include a lower alkyl group of 1 to 5 carbon atoms, a fluorine atom, a fluorinated lower alkyl group of 1 to 5 carbon atoms, and an oxygen atom (=O).

Examples of aromatic hydrocarbon groups include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group;

an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

Among these examples, the aforementioned divalent aromatic hydrocarbon group is preferable, and an aromatic hydrocarbon group in which one hydrogen atom has been removed from a phenyl group, or an aromatic hydrocarbon group in which one hydrogen atom has been removed from a naphthyl group is particularly desirable.

The alkyl chain within the arylalkyl group preferably has 1 to 4 carbon atom, more preferably 1 or 2, and most preferably 1.

The aromatic hydrocarbon group may or may not have a substituent. Examples of the substituent include a lower alkyl group of 1 to 5 carbon atoms, a fluorine atom, a fluorinated lower alkyl group of 1 to 5 carbon atoms, and an oxygen atom (=O).

Among the above-mentioned examples, as the hydrocarbon group which may have a substituent, a linear, branched or cyclic aliphatic hydrocarbon group or a divalent aromatic hydrocarbon group is preferable, and a methylene group, and ethylene group, —CH(CH$_3$)—, a group in which one hydrogen atom has been removed from a tetracyclododecyl group, or an aromatic hydrocarbon group in which one hydrogen atom has been removed from a phenyl group is particularly desirable.

(Divalent Linking Group Containing a Hetero Atom)

A hetero atom is an atom other than carbon and hydrogen, and examples thereof include an oxygen atom, a nitrogen atom, a sulfur atom and a halogen atom.

Examples of the divalent linking group containing a hetero atom include —O—, —C(=O)—, —C(=O)—O—, a carbonate bond (—O—C(=O)—O—), —NH—, —NR$^{04}$— (wherein R$^{04}$ represents an alkyl group), —NH—C(=O)—, =N—, and a combination of any of these "groups" with a divalent hydrocarbon group.

As examples of the divalent hydrocarbon group, the same groups as those described above for the hydrocarbon group which may have a substituent can be given, and a linear or branched aliphatic hydrocarbon group is preferable.

Among the above-mentioned examples, as the divalent linking group containing a hetero atom, a combination of any of the aforementioned "groups" with a divalent hydrocarbon group is preferable. More specifically, it is particularly desirable to use a combination of any of the aforementioned "groups" with the aforementioned aliphatic hydrocarbon group, or a combination of the aforementioned aliphatic hydrocarbon group, any of the aforementioned "groups" and the aforementioned aliphatic hydrocarbon group.

In general formula (f1-2), $A_{aryl}$ represents a divalent aromatic cyclic group which may have a substituent. A specific example of $A_{aryl}$ includes an aromatic hydrocarbon ring (which may have a substituent) having two hydrogen atoms removed therefrom.

The ring skeleton of the aromatic cyclic group for $A_{aryl}$ preferably has 6 to 15 carbon atoms. Examples of the ring skeleton include a benzene ring, a naphthalene ring, a phenanthrene ring and an anthracene ring. Among these, a benzene ring or a naphthalene ring is particularly desirable.

Examples of substituents for the aromatic cyclic group represented by $A_{aryl}$ include a halogen atom, an alkyl group, an alkoxy group, a halogenated alkyl group of 1 to 5 carbon atoms, and an oxygen atom (=O). Examples of the halogen atom include a fluorine atom, a chlorine atom, an iodine atom and a bromine atom. As the substituent for the aromatic cyclic group represented by $A_{aryl}$, a fluorine atom is preferable.

$A_{aryl}$ may be either an aromatic cyclic group having no substituent, or an aromatic cyclic group having a substituent, although an aromatic cyclic group having no substituent is preferable.

When $A_{aryl}$ represents an aromatic cyclic group having a substituent, the number of the substituent may be 1 or more, preferably 1 or 2, and more preferably 1.

In general formula (f1-2), $X^{01}$ represents a single bond or a divalent linking group. Examples of divalent linking groups include an alkylene group of 1 to 10 carbon atoms, —O—, —C(=O)—, —C(=O)—O—, a carbonate bond (—O—C(=O)—O—), —NH—C(=O)—, and a combination of these groups. Of these, a combination of —O— with an alkylene group of 1 to 10 carbon atoms is particularly desirable.

Examples of alkylene groups of 1 to 10 carbon atoms include linear, branched or cyclic alkylene groups, and a linear or branched alkylene group of 1 to 5 carbon atoms and a cyclic alkylene group of 4 to 10 carbon atoms are preferable.

Among structural units represented by general formula (f1-1), structural units represented by general formulas (f1-11) to (f1-15) shown below are preferable.

Further, among structural units represented by general formula (f1-2), structural units represented by general formulas (f1-21) to (f1-27) are preferable.

[Chemical Formula 51.]
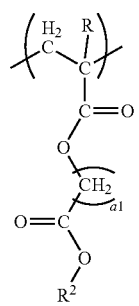
(f1-11)
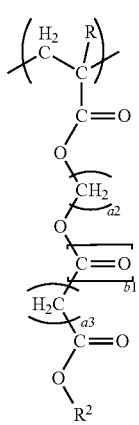
(f1-12)
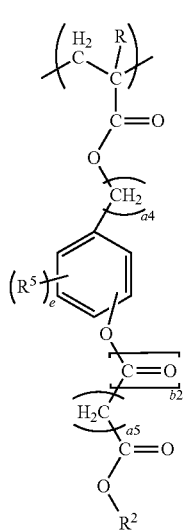
(f1-13)
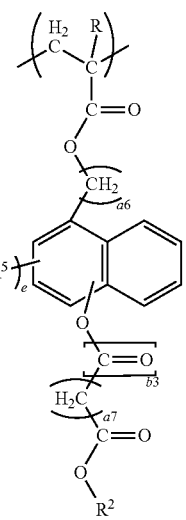
(f1-14)
[Chemical Formula 52.]
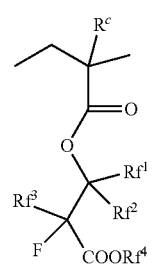
(f1-15)
[Chemical Formula 53.]
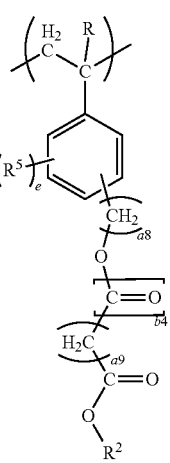
(f1-21)

(f1-22)
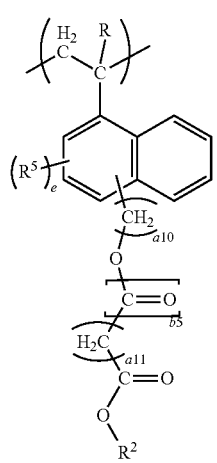

(f1-23)

(f1-24)
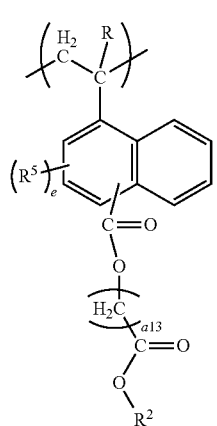

[Chemical Formula 54.]

(f1-25)
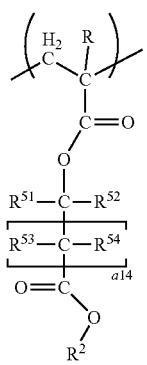

(f1-26)

(f1-27)

In general formulas (f1-11) to (f1-14), (f1-21) to (f1-24) and (f1-25) to (f1-27), R and $R^2$ are the same as defined above; each of $R^{51}$ and $R^{52}$ independently represents an alkyl group of 1 to 10 carbon atoms; each of $R^{53}$ and $R^{54}$ independently represents a hydrogen atom or an alkyl group of 1 to 10 carbon atoms; each of a1, a2, a3, a5, a7 a9 and a11 to a13 independently represents an integer of 1 to 5; each of a4, a6, a8 and a10 independently represents an integer of 0 to 5; each of a14 to a16 independently represents an integer of 0 to 5; each of b1 to b5 independently represents 0 or 1; $R^5$ represents a substituent; and e represents an integer of 0 to 2.

In general formulas (f1-11) to (f1-14), (f1-21) to (f1-24) and (f1-25) to (f1-27), as R, a hydrogen atom or a methyl group is preferable.

In general formula (f1-11), a1 is preferably an integer of 1 to 3, more preferably 1 or 2.

In general formula (f1-12), it is preferable that each of a2 and a3 independently represent an integer of 1 to 3, more preferably 1 or 2.

In general formula (f1-13), a4 is preferably an integer of 0 to 3, more preferably an integer of 0 to 2, and most preferably 0 or 1.

a5 is preferably an integer of 1 to 3, and more preferably 1 or 2.

Examples of the substituent represented by $R^5$ include a halogen atom, an alkyl group of 1 to 5 carbon atoms, an alkoxy group of 1 to 5 carbon atoms, a halogenated alkyl group of 1 to 5 carbon atoms and an oxygen atom (=O). Examples of the alkyl group of 1 to 5 carbon atoms include the same alkyl group of 1 to 5 carbon atoms as those described above for R. Examples of the halogen atom include a fluorine atom, a chlorine atom, an iodine atom and a bromine atom. Examples of the halogenated alkyl group of 1 to 5 carbon atoms include the same halogenated alkyl group of 1 to 5 carbon atoms as those described above for R.

e is preferably 0 or 1, and most preferably 0 from an industrial viewpoint.

b2 is preferably 0.

In general formula (f1-14), a6 is preferably an integer of 0 to 3, more preferably an integer of 0 to 2, and most preferably 0 or 1.

a7 is preferably an integer of 1 to 3, and more preferably 1 or 2.

b3 is preferably 0.

$R^5$ and e are the same as defined above.

In general formula (f1-21), a8 is preferably an integer of 0 to 3, more preferably an integer of 0 to 2, and most preferably 0 or 1.

a9 is preferably an integer of 1 to 3, and more preferably 1 or 2.

b4 is preferably 0.

R5 and e are the same as defined above.

In general formula (f1-22), a10 is preferably an integer of 0 to 3, more preferably an integer of 0 to 2, and most preferably 0 or 1.

a11 is preferably an integer of 1 to 3, and more preferably 1 or 2.

b5 is preferably 0.

$R^5$ and e are the same as defined above.

In general formula (f1-23), a12 is preferably an integer of 1 to 3, more preferably 1 or 2.

$R^5$ and e are the same as defined above.

In general formula (f1-24), a13 is preferably an integer of 1 to 3, more preferably 1 or 2.

$R^5$ and e are the same as defined above.

In general formulas (f1-25) to (f1-27), it is preferable that each of a14, a15 and a16 independently represent 0 to 3, more preferably 0 to 2, and most preferably 0 or 1.

It is preferable that each of $R^{51}$ and $R^{52}$ independently represent a linear, branched or cyclic alkyl group of 1 to 10 carbon atoms, and specific examples thereof include a methyl group, an ethyl group, an n-propyl group, an isopropyl group, an n-butyl group, an isobutyl group, a tert-butyl group, a tert-amyl group, a cyclopentyl group, a cyclohexyl group, a cyclooctyl group, a norbornyl group, an isobornyl group, a tricyclodecanyl group, an adamantyl group and a tetracyclododecanyl group. Of these, an alkyl group of 1 to 6 carbon atoms is preferable, more preferably an alkyl group of 1 to 4 carbon atoms, and most preferably a methyl group or an ethyl group.

It is preferable that each of $R^{53}$ and $R^{54}$ independently represent a hydrogen atom or a linear, branched or cyclic alkyl group of 1 to 10 carbon atoms. For $R^{53}$ and R54, the linear, branched or cyclic alkyl group of 1 to 10 carbon atoms is the same as defined above for $R^{51}$ and $R^{52}$.

In general formulas (f1-26) and (f1-27), $R^5$ and e are the same as defined above.

In general formula (f1-15), $R^c$ represents a hydrogen atom or a methyl group.

In general formula (f1-15), each of $Rf^1$ and $Rf^2$ independently represents a hydrogen atom, an alkyl group of 1 to 4 carbon atoms or a fluorinated alkyl group of 1 to 4 carbon atoms.

The alkyl group of 1 to 4 carbon atoms for $Rf^1$ and $Rf^2$ may be linear, branched or cyclic, and a linear or branched alkyl group is preferable. Specific examples thereof include a methyl group and an ethyl group, and an ethyl group is particularly desirable.

The fluorinated alkyl group of 1 to 4 carbon atoms for $Rf^1$ and $Rf^2$ is an alkyl group of 1 to 4 carbon atoms in which part or all of the hydrogen atoms have been substituted with a fluorine atom. In the fluorinated alkyl group, the alkyl group prior to being substituted with a fluorine atom may be linear, branched or cyclic, and examples thereof include the same groups as those described above for the "alkyl group of 1 to 4 carbon atoms for $Rf^1$ and $Rf^2$"

Among these, as $Rf^1$ and $Rf^2$, a hydrogen atom or an alkyl group of 1 to 4 carbon atoms is preferable, and it is particularly desirable that one of $Rf^1$ and $Rf^2$ represents a hydrogen atom, and the other represents an alkyl group of 1 to 4 carbon atoms.

In general formula (f1-15), $Rf^3$ represents a fluorine atom or a fluorinated alkyl group of 1 to 4 carbon atoms.

The fluorinated alkyl group of 1 to 4 carbon atoms represented by $Rf^3$ is the same as defined for the "fluorinated alkyl group of 1 to 4 carbon atoms for $Rf^1$ and $Rf^2$", preferably having 1 to 3 carbon atoms, and more preferably having 1 or 2 carbon atoms.

In the fluorinated alkyl group represented by $Rf^3$, the percentage of the number of fluorine atoms based on the total number of hydrogen atoms and fluorine atoms (fluorination ratio (%)) is preferably 30 to 100%, and more preferably 50 to 100%. The higher the fluorination ratio, the higher the hydrophobicity of the resist film.

In general formula (f1-15), Re represents a linear or branched alkyl group of 1 to 4 carbon atoms or a linear fluorinated alkyl group of 1 to 4 carbon atoms, and a linear alkyl group of 1 to 4 carbon atoms or a linear fluorinated alkyl group of 1 to 4 carbon atoms is preferable.

Specific examples of the alkyl group for $Rf^4$ include a methyl group, an ethyl group, a propyl group, an isopropyl group, an n-butyl group, an isobutyl group and a tert-butyl group. Among these, a methyl group or an ethyl group is preferable, and a methyl group is particularly desirable.

Specific examples of preferable fluorinated alkyl group for $Rf^4$ include —$CH_2$—$CF_3$, —$CH_2$—$CF_2$—$CF_3$, and —$CH_2$—$CF_2$—$CF_2$—$CF_3$. Among these examples, —$CH_2$—$CF_3$ is most preferable.

Specific examples of structural units represented by general formulae (f1-11) to (f1-15) and (f1-21) to (f1-27) are shown below.

[Chemical Formula 55.]
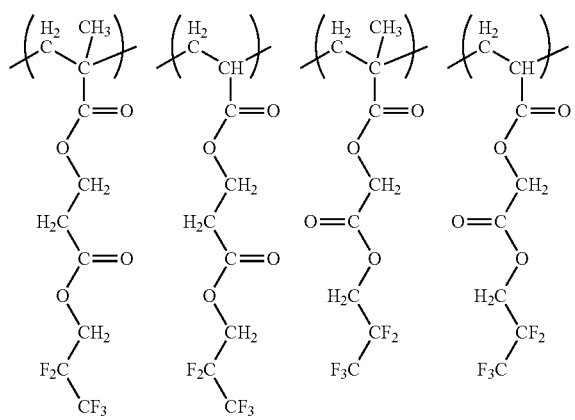
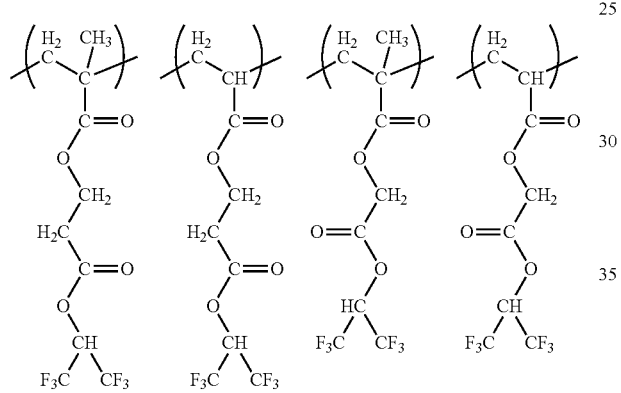
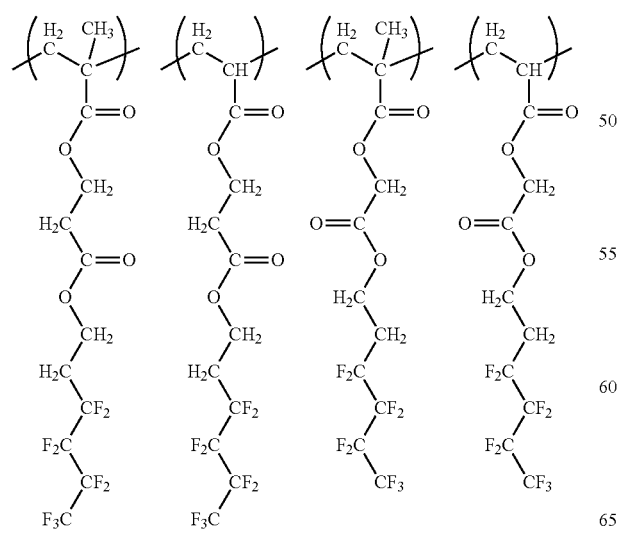
[Chemical Formula 56.]
-continued
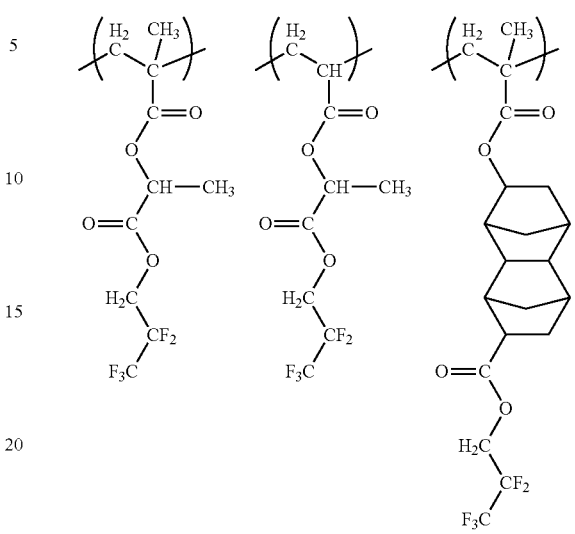
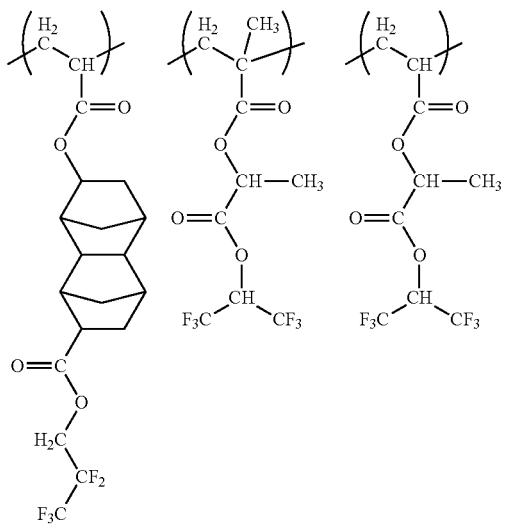
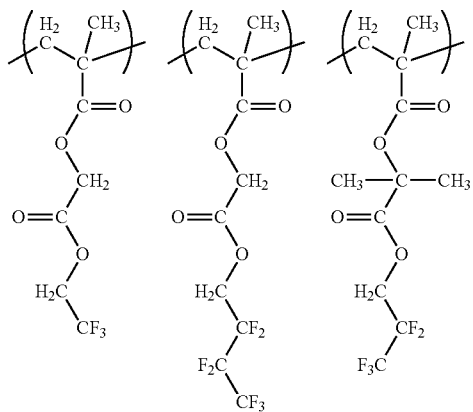

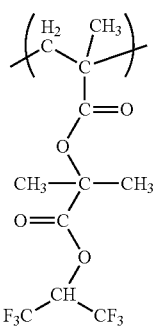
[Chemical Formula 57.]
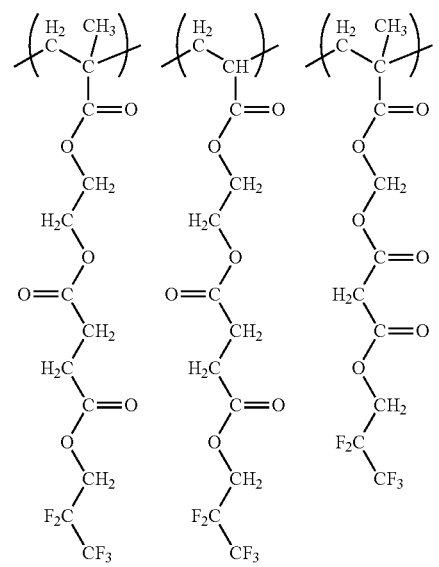
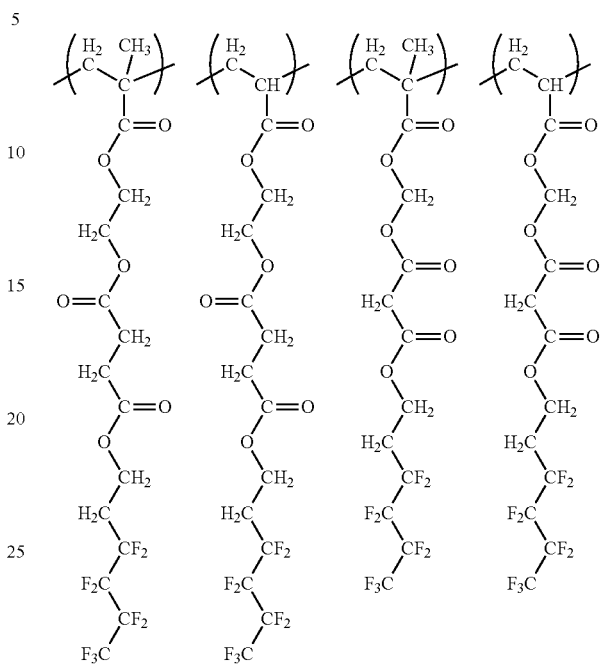
[Chemical Formula 58]
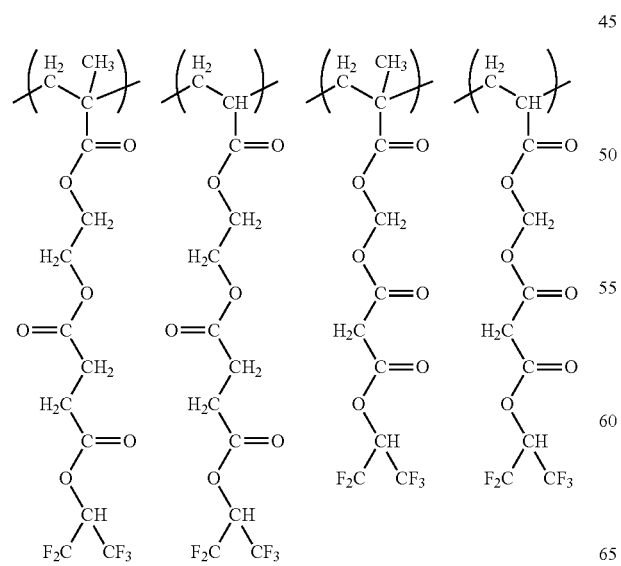
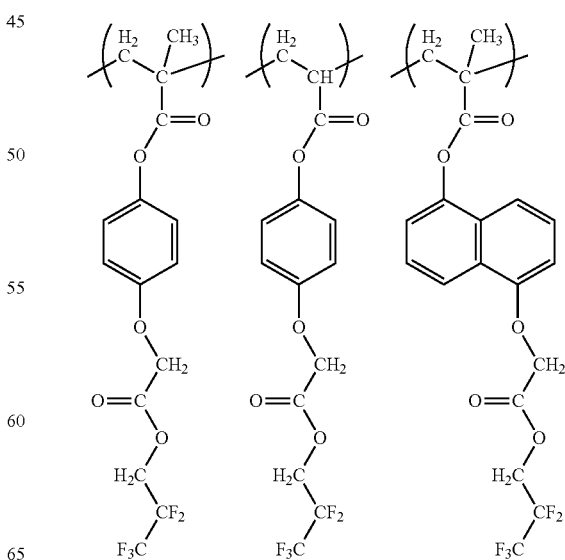

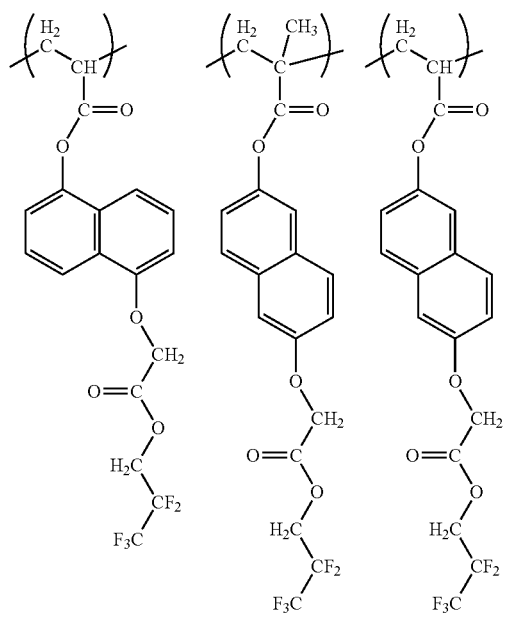
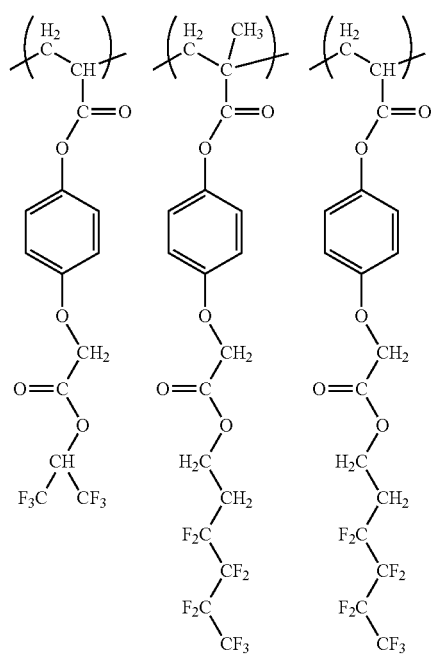
[Chemical Formula 59.]
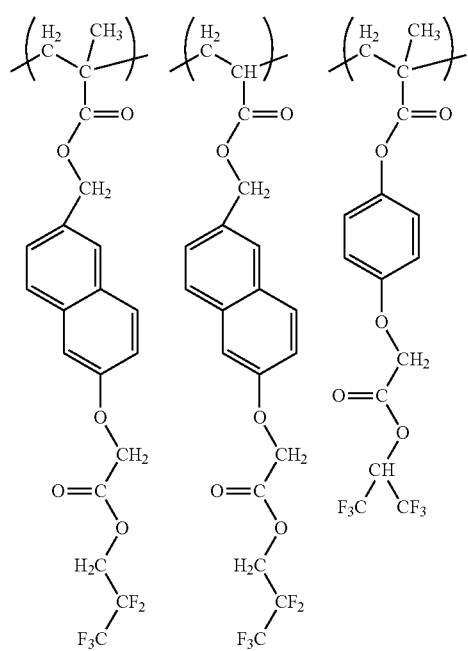
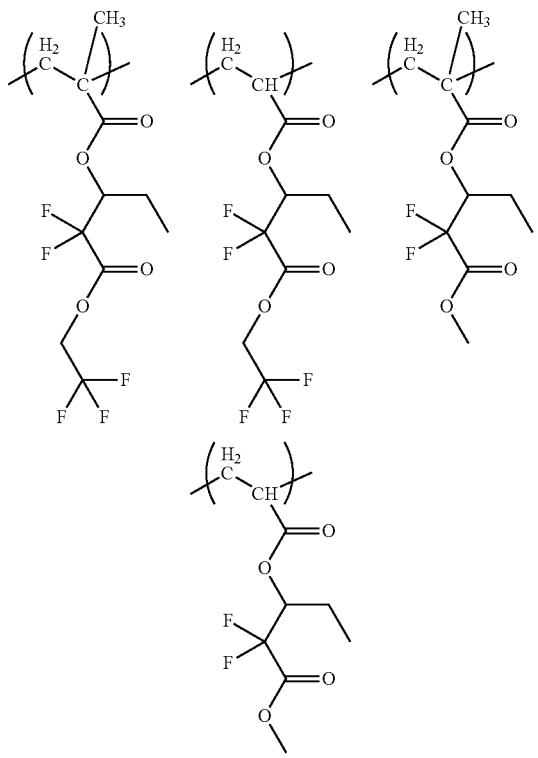

[Chemical Formula 60.]
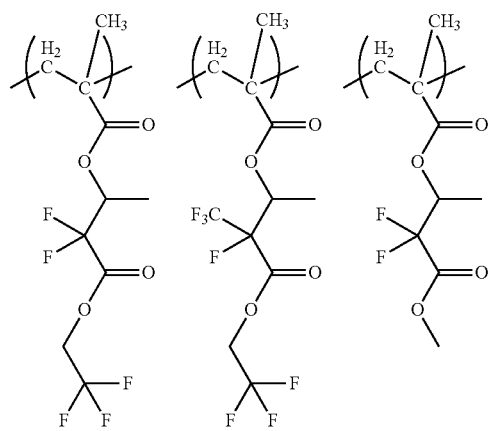
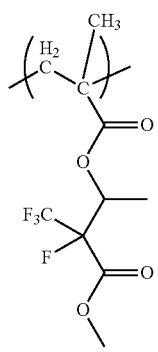
[Chemical Formula 61.]
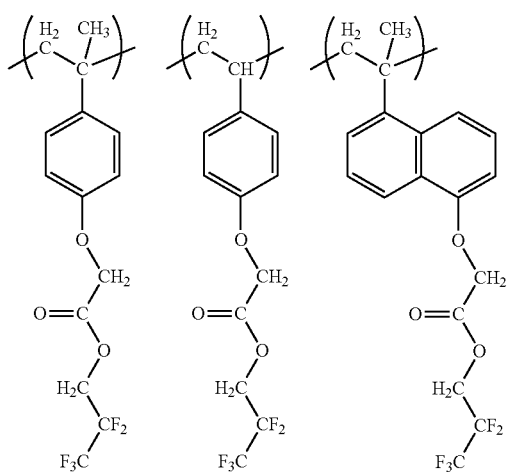
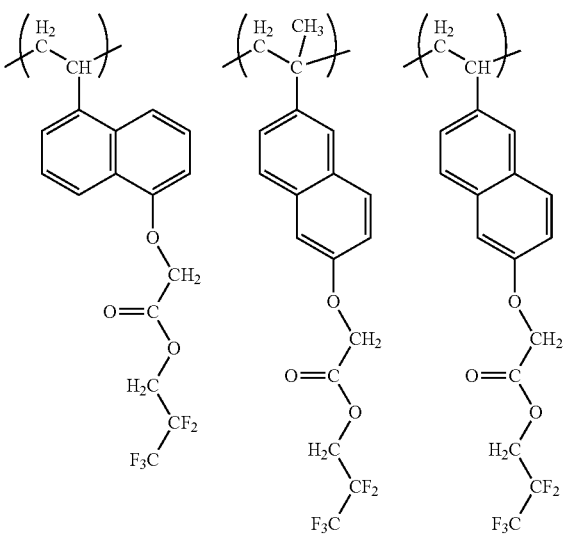
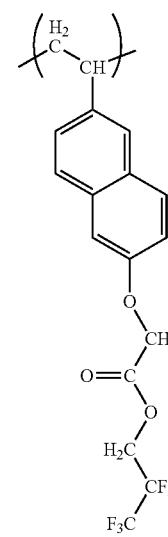

-continued

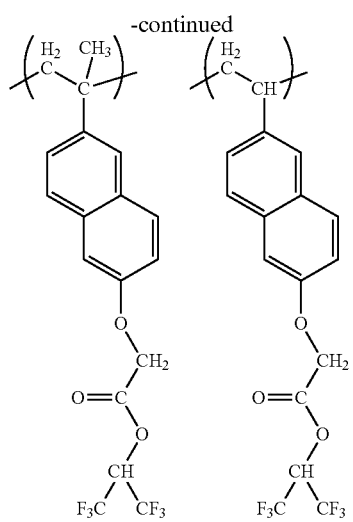

As the structural unit (f1), at least one structural unit selected from the group consisting of structural units represented by general formulas (f1-11) to (f1-15) and (f1-21) to (f1-24) is preferable, more preferably at least one structural unit selected from the group consisting of structural units represented by general formulas (f1-11) to (f1-13), (f1-15), (f1-21) and (f1-22), and most preferably at least one structural unit selected from the group consisting of structural units represented by general formulas (f1-11), (f1-15) and (f1-22).

In the component (F), as the structural unit (f1), one kind of structural unit may be used, or two or more kinds may be used in combination.

In the component (F), the amount of the structural unit (f1) based on the combined total (100 mol %) of all structural units constituting the component (F) is preferably 30 to 99 mol %, more preferably 40 to 90 mol %, and most preferably 55 to 85 mol %. When the amount of the structural unit (f1) is at least as large as the lower limit of the above-mentioned range, in the formation of a resist pattern, the component (F) becomes hydrophilic at the time of alkali developing, and generation of defects caused by adhered substance or the like on the surface of the resist pattern. On the other hand, when the amount of the structural unit (f1) is no more than the upper limit of the above-mentioned range, a good balance can be achieved with the other structural units.

(Structural Unit (f2))

The component (F1) includes, in addition to the structural unit (f1), a structural unit (f2) represented by general formula (f2-r-1) shown below.

[Chemical Formula 62.]

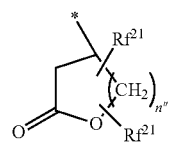

(f2-r-1)

In the formula, each $Rf^{21}$ independently represents a hydrogen atom, an alkyl group, an alkoxy group, a hydroxy group, a hydroxyalkyl group or a cyano group; n" represents an integer of 0 to 2; and * represents a valence bond.

In general formula (f2-r-1), the alkyl group, the alkoxy group or the hydroxyalkyl group for $Rf^{21}$ is the same as the alkyl group, the alkoxy group or the hydroxyalkyl group for $Ra'^{21}$ in the aforementioned general formulae (a2-r-1) to (a2-r-7).

As the structural unit (f2), a structural unit derived from an acrylate ester which may have the hydrogen atom bonded to the carbon atom on the α-position substituted with a substituent is preferable.

The structural unit (f2) is preferably a structural unit represented by general formula (f2-1) shown below.

[Chemical Formula 63.]

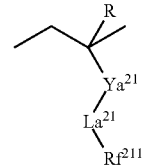

(f2-1)

In the formula, R represents a hydrogen atom, an alkyl group of 1 to 5 carbon atoms or a halogenated alkyl group of 1 to 5 carbon atoms; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group; provided that, when $La^{21}$ represents —O—, $Ya^{21}$ does not represents —CO—; and $Rf^{211}$ is a group represented by the aforementioned general formula (f2-r-1).

In general formula (f2-1), R, $Ya^{21}$, $La^{21}$ and R' are the same as defined for R, $Ya^{21}$, $La^{21}$ and R' in the aforementioned general formula (a2-1).

In general formula (f2-1), $Rf^{211}$ is a group represented by the aforementioned general formula (f2-r-1).

As the structural unit (f2) contained in the component (F1), 1 kind of structural unit may be used, or 2 or more kinds may be used.

When the component (F1) includes the structural unit (f2), the amount of the structural unit (f2) based on the combined total (100 mol %) of all structural units constituting the component (A1) is preferably 1 to 70 mol %, more preferably 10 to 60 mol %, and still more preferably 15 to 45 mol %.

When the amount of the structural unit (f2) is at least as large as the lower limit of the above-mentioned range, the effect of improving defects is enhanced. On the other hand, when the amount of the structural unit (f2) is no more than the upper limit of the above-mentioned range, a good balance can be achieved with the other structural units.

The component (F) can be obtained, for example, by a conventional radical polymerization or the like of the monomers corresponding with the desired structural units, using a radical polymerization initiator such as azobisisobutyronitrile (AIBN) or dimethyl 2,2'-azobis(isobutyrate).

The weight average molecular weight (Mw) (the polystyrene equivalent value determined by gel permeation chromatography) of the component (F) is preferably 1,000 to 50,000, more preferably 3,000 to 40,000, and most preferably 5,000 to 30,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5.

As the component (F), one kind may be used alone, or two or more kinds may be used in combination.

The amount of the component (F) relative to 100 parts by weight of the component (A) is preferably within a range from 0.1 to 20 parts by weight, more preferably 0.5 to 10 parts by weight, and still more preferably 1 to 5 parts by weight. When the amount of the component (F) is at least as large as the lower limit of the above-mentioned range, in the formation of a resist pattern, generation of defects can be suppressed. On the other hand, when the amount of the component (F) is no more than the upper limit of the above-mentioned range, lithography properties are improved.

<<Acid Generator Component; Component (B)>>

In the present embodiment, the resist composition may include an acid generator component (B) (hereafter, referred to as "component (B)") which generates acid upon exposure.

As the component (B), there is no particular limitation, and any of the known acid generators used in conventional chemically amplified resist compositions can be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators. Among these, it is preferable to use an onium salt acid generator.

As the onium salt acid generator, a compound represented by general formula (b-1) below (hereafter, sometimes referred to as "component (b-1)"), a compound represented by general formula (b-2) below (hereafter, sometimes referred to as "component (b-2)") or a compound represented by general formula (b-3) below (hereafter, sometimes referred to as "component (b-3)") may be used.

[Chemical Formula 64.]

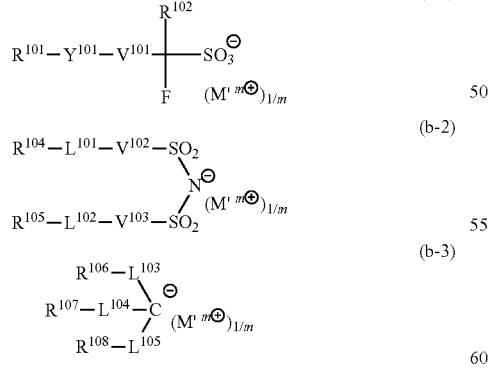

In the formulae, $R^{101}$ and $R^{104}$ to $R^{108}$ each independently represents a cyclic group which may have a substituent, a chain-like alkyl group which may have a substituent or a chain-like alkenyl group which may have a substituent, provided that $R^{104}$ and $R^{105}$ may be mutually bonded to form a ring; $R^{106}$ to $R^{108}$ may be mutually bonded to form a ring; $R^{102}$ represents a fluorine atom or a fluorinated alkyl group of 1 to 5 carbon atoms; $Y^{101}$ represents a single bond or a divalent linking group containing an oxygen atom; $V^{101}$ to $V^{103}$ each independently represents a single bond, an alkylene group or a fluorinated alkylene group; $L^{101}$ and $L^{102}$ each independently represents a single bond or an oxygen atom; $L^{103}$ to $L^{105}$ each independently represents a single bond, —CO— or —SO$_2$—; and $M'^{m+}$ represents an organic cation having a valency of m.

{Anion Moiety}

Anion Moiety of Component (b-1)

In the formula (b-1), $R^{101}$ represents a cyclic group which may have a substituent, a chain-like alkyl group which may have a substituent or a chain-like alkenyl group which may have a substituent.

Cyclic Group Which May Have a Substituent for $R^{101}$

The cyclic group is preferably a cyclic hydrocarbon group, and the cyclic hydrocarbon group may be either an aromatic hydrocarbon group or an aliphatic hydrocarbon group.

As the aromatic hydrocarbon group for $R^{101}$, groups in which one hydrogen atom has been removed from an aromatic hydrocarbon ring described above in relation to the divalent aromatic hydrocarbon group for Va$^1$ in the formula (a1-1) or an aromatic compound containing two or more aromatic ring can be mentioned, and a phenyl group or a naphthyl group is preferable.

As the cyclic aliphatic hydrocarbon group for $R^{101}$, groups in which one hydrogen atom has been removed from a monocycloalkane or a polycycloalkane exemplified above in the explanation of the divalent aliphatic hydrocarbon group for Va$^1$ in the formula (a1-1) can be mentioned, and an adamantyl group or a norbornyl group is preferable.

Further, the cyclic hydrocarbon group for $R^{101}$ may contain a hetero atom like as a heterocycle, and specific examples thereof include lactone-containing cyclic groups represented by the aforementioned general formulas (a2-r-1) to (a2-r-7), —SO$_2$— containing cyclic groups represented by the aforementioned formulas (a5-r-1) to (a5-r-4) and heterocyclic groups (r-hr-1) to (r-hr-16) shown below.

[Chemical Formula 65.]

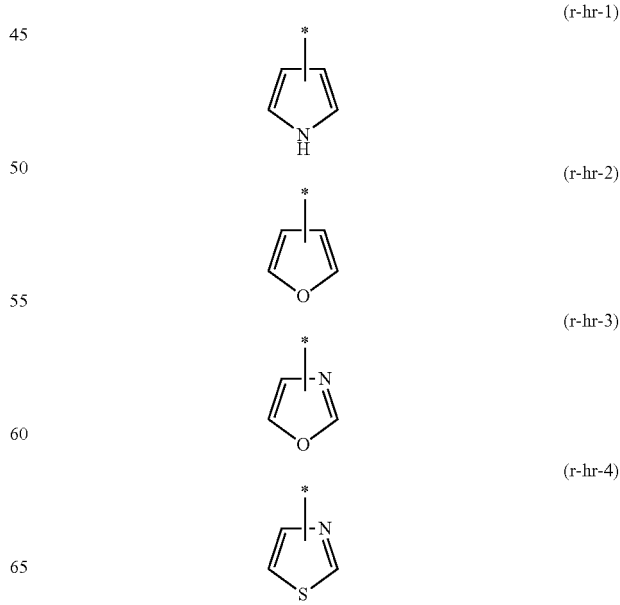

(r-hr-5) 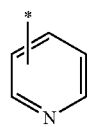

(r-hr-6) 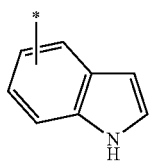

(r-hr-7) 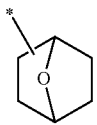

(r-hr-8) 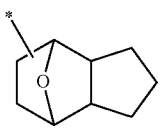

(r-hr-9) 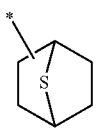

(r-hr-10) 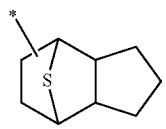

(r-hr-11) 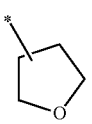

(r-hr-12) 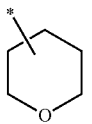

(r-hr-13) 

(r-hr-14) 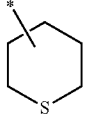

(r-hr-15) 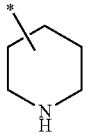

(r-hr-16) 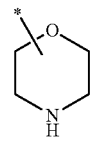

As the substituent for the cyclic hydrocarbon group for $R^{101}$, an alkyl group, an alkoxy group, a halogen atom, a halogenated alkyl group, a hydroxyl group, a carbonyl group, a nitro group or the like can be used.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

—Chain-Like Alkyl Group Which May Have a Substituent for $R^{101}$

The chain-like alkyl group for $R^{101}$ may be linear or branched.

The linear alkyl group preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

Chain-Like Alkenyl group Which May Have a Substituent for $R^{101}$

The chain-like alkenyl group for $R^{101}$ may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylpropenyl group and a 2-methylpropenyl group.

Among the above-mentioned examples, as the chain-like alkenyl group, a propenyl group is particularly desirable.

As the substituent for the chain-like alkyl group or alkenyl group for $R^{101}$, an alkoxy group, a halogen atom, a halogenated alkyl group, a hydroxyl group, a carbonyl group, a nitro group, an amino group, a cyclic group for $R^{101}$ or the like can be used.

Among these examples, as $R^{101}$, a cyclic group which may have a substituent is preferable, and a cyclic hydrocarbon group which may have a substituent is more preferable. Specifically, a phenyl group, a naphthyl group, a group in which one or more hydrogen atoms have been removed from a polycycloalkane, a lactone-containing cyclic group represented by any one of the aforementioned formula (a2-r-1) to (a2-r-7), and an —$SO_2$— containing cyclic group represented by any one of the aforementioned formula (a5-r-1) to (a5-r-4).

In formula (b-1), $Y^{101}$ represents a single bond or a divalent linking group containing an oxygen atom.

In the case where $Y^{101}$ is a divalent linking group containing an oxygen atom, $Y^{101}$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an oxycarbonyl group (—O—C(=O)—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group. Furthermore, the combinations may have a sulfonyl group (—$SO_2$—) bonded thereto. As the combination, the linking group represented by formulas (y-al-1) to (y-al-7) shown below can be mentioned.

[Chemical Formula 66.]

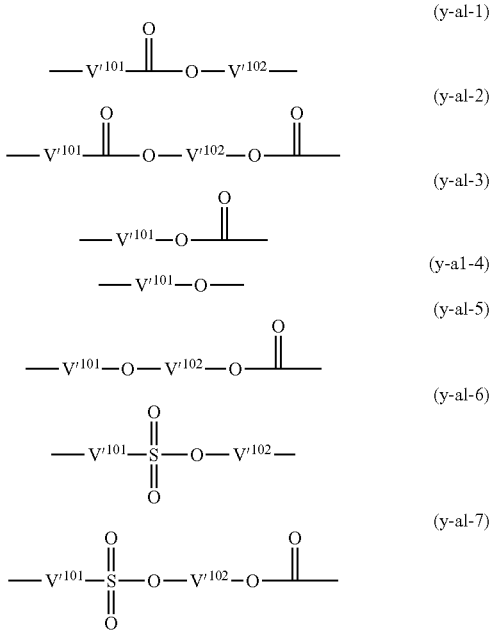

In the formulae, $V'^{101}$ represents a single bond or an alkylene group of 1 to 5 carbon atoms; $V'^{102}$ represents a divalent saturated hydrocarbon group of 1 to 30 carbon atoms.

The divalent saturated hydrocarbon group for $V'^{102}$ is preferably an alkylene group of 1 to 30 carbon atoms.

The alkylene group for $V'^{101}$ and $V'^{102}$ may be a linear alkylene group or a branched alkylene group, and a linear alkylene group is preferable.

Specific examples of the alkylene group for $V'^{101}$ and $V'^{102}$ include a methylene group [—$CH_2$—]; an alkylmethylene group, such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— and —$C(CH_2CH_3)_2$—; an ethylene group [—$CH_2CH_2$—]; an alkylethylene group, such as —$CH(CH_3)CH_2$—, —$CH(CH_3)CH(CH_3)$—, —$C(CH_3)_2CH_2$— and —$CH(CH_2CH_3)CH_2$—; a trimethylene group (n-propylene group) [—$CH_2CH_2CH_2$—]; an alkyltrimethylene group, such as —$CH(CH_3)CH_2CH_2$— and —$CH_2CH(CH_3)CH_2$—; a tetramethylene group [—$CH_2CH_2CH_2CH_2$—]; an alkyltetramethylene group, such as —$CH(CH_3)CH_2CH_2CH_2$—, —$CH_2CH(CH_3)CH_2CH_2$—; and a pentamethylene group [—$CH_2CH_2CH_2CH_2CH_2$—].

Further, part of methylene group within the alkylene group for $V'^{101}$ and $V'^{102}$ may be substituted with a divalent aliphatic cyclic group of 5 to 10 carbon atoms. The aliphatic cyclic group is preferably a divalent group in which one hydrogen atom has been removed from the cyclic aliphatic hydrocarbon group for $Ra^{t3}$ in the aforementioned formula (a1-r-1), and a cyclohexylene group, 1,5-adamantylene group or 2,6-adamantylene group is preferable.

$Y^{101}$ is preferably a divalent linking group containing an ether bond or an ester bond, and groups represented by the aforementioned formulas (y-a1-1) to (y-a1-5) are preferable.

In formula (b-1), $V^{101}$ represents a single bond, an alkylene group or a fluorinated alkylene group. The alkylene group and the fluorinated alkylene group for $V^{101}$ on preferably has 1 to 4 carbon atoms. Examples of the fluorinated alkylene group for $V^{101}$ include a group in which part or all of the hydrogen atoms within the alkylene group for $V^{101}$ have been substituted with fluorine. Among these examples, as $V^{101}$, a single bond or a fluorinated alkylene group of 1 to 4 carbon atoms is preferable.

In formula (b-1), $R^{102}$ represents a fluorine atom or a fluorinated alkyl group of 1 to 5 carbon atoms. $R^{102}$ is preferably a fluorine atom or a perfluoroalkyl group of 1 to 5 carbon atoms, and more preferably a fluorine atom.

As a specific example of the anion moiety for the component (b-1), in the case where $Y^{101}$ a single bond, a fluorinated alkylsulfonate anion such as a trifluoromethanesulfonate anion or a perfluorobutanesulfonate anion can be mentioned; and in the case where $Y^{101}$ represents a divalent linking group containing an oxygen atom, anions represented by formulae (an-1) to (an-3) shown below can be mentioned.

[Chemical Formula 67.]

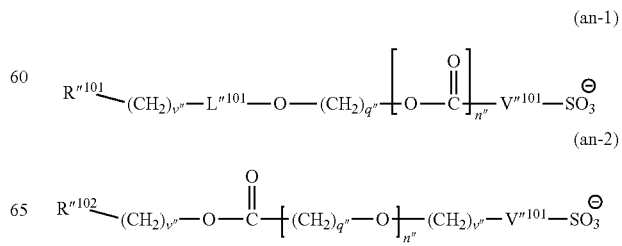

-continued

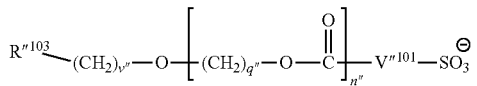
(an-3)

In the formulae, $R''^{101}$ represents an aliphatic cyclic group which may have a substituent, a group represented by any one of the aforementioned formulae (r-hr-1) to (r-hr-6) or a chain-like alkyl group which may have a substituent; $R''^{102}$ represents an aliphatic cyclic group which may have a substituent, a lactone-containing cyclic group represented by any one of the aforementioned general formulae (a2-r-1) to (a2-r-7) or an —$SO_2$— containing cyclic group represented by any one of the aforementioned general formulae (a5-r-1) to (a5-r-4); $R''^{103}$ represents an aromatic cyclic group which may have a substituent, an aliphatic cyclic group which may have a substituent or a chain-like alkenyl group which may have a substituent; $V''^{101}$ represents a fluorinated alkylene group; $L''^{101}$ represents —C(=O)— or —$SO_2$—; v" represents an integer of 0 to 3; q" represents an integer of 1 to 20; and n" represents 0 or 1.

As the aliphatic cyclic group for $R''^{101}$, $R''^{102}$ and $R''^{103}$ which may have a substituent, the same groups as the cyclic aliphatic hydrocarbon group for $R^{101}$ described above are preferable. As the substituent, the same groups as those described above for substituting the cyclic aliphatic hydrocarbon group for $R^{101}$ can be mentioned.

As the aromatic cyclic group for $R''^{103}$ which may have a substituent, the same groups as the aromatic hydrocarbon group for the cyclic hydrocarbon group represented by $R^{101}$ described above are preferable. The substituent is the same as defined for the substituent for the aromatic hydrocarbon group represented by $R^{101}$.

As the chain-like alkyl group for $R''^{101}$ which may have a substituent, the same groups as those described above for $R^{101}$ are preferable. As the chain-like alkenyl group for $R''^{103}$ which may have a substituent, the same groups as those described above for $R^{101}$ are preferable. $V''^{101}$ is preferably a fluorinated alkylene group of 1 to 3 carbon atoms, and most preferably —$CF_2$—, —$CF_2CF_2$—, —$CHFCF_2$—, —$CF(CF_3)CF_2$— or —$CH(CF_3)CF_2$—.

Anion Moiety of Component (b-2)

In formula (b-2), $R^{104}$ and $R^{105}$ each independently represents a cyclic group which may have a substituent, a chain-like alkyl group which may have a substituent or a chain-like alkenyl group which may have a substituent, and is the same as defined for $R^{101}$ in formula (b-1). $R^{104}$ and $R^{105}$ may be mutually bonded to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. The smaller the number of carbon atoms of the chain-like alkyl group for $R^{104}$ and $R^{105}$, the more the solubility in a resist solvent is improved. Further, in the chain-like alkyl group for $R^{104}$ and $R^{105}$, it is preferable that the number of hydrogen atoms substituted with fluorine atoms is as large as possible because the acid strength increases and the transparency to high energy radiation of 200 nm or less or electron beam is improved. The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

In formula (b-2), $V^{102}$ and $V^{103}$ each independently represents a single bond, an alkylene group or a fluorinated alkylene group, and is the same as defined for $V^{101}$ in formula (b-1).

In formula (b-2), $L^{101}$ and $L^{102}$ each independently represents a single bond or an oxygen atom.

Anion Moiety of Component (b-3)

In formula (b-3), $R^{106}$ to $R^{108}$ each independently represents a cyclic group which may have a substituent, a chain-like alkyl group which may have a substituent or a chain-like alkenyl group which may have a substituent, and is the same as defined for $R^{101}$ in formula (b-1).

$L^{103}$ to $L^{105}$ each independently represents a single bond, —CO— or —$SO_2$—.

{Cation Moiety}

In formulae (b-1), (b-2) and (b-3), $M'^{m+}$ represents an organic cation having a valency of m, preferably a sulfonium cation or an iodonium cation, and most preferably a cation represented by any one of formulae (ca-1) to (ca-4) shown below.

[Chemical Formula 68.]

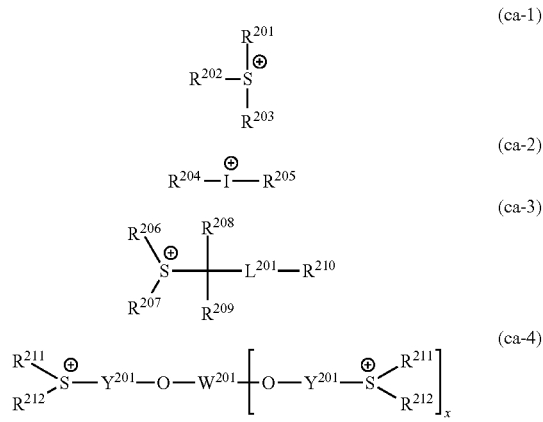

In the formulae, $R^{201}$ to $R^{207}$, $R^{211}$ and $R^{212}$ each independently represents an aryl group, an alkyl group or an alkenyl group, provided that two of $R^{201}$ to $R^{203}$, $R^{206}$ and $R^{207}$, or $R^{211}$ and $R^{212}$ may be mutually bonded to form a ring with the sulfur atom; $R^{208}$ and $R^{209}$ each independently represents a hydrogen atom or an alkyl group of 1 to 5 carbon atoms; $R^{210}$ represents an aryl group which may have a substituent, an alkyl group which may have a substituent, an alkenyl group which may have a substituent or an —$SO_2$— containing cyclic group which may have a substituent; $L^{201}$ represents —C(=O)— or —C(=O)—O—; $Y^{201}$ each independently represents an arylene group, an alkylene group or an alkenylene group; x represents 1 or 2; and $W^{201}$ represents a linking group having a valency of (x+1).

As the aryl group for $R^{201}$ to $R^{207}$, $R^{211}$ and $R^{212}$ an unsubstituted aryl group of 6 to 20 carbon atoms can be mentioned, and a phenyl group or a naphthyl group is preferable.

The alkyl group for $R^{201}$ to $R^{207}$, $R^{211}$ and $R^{212}$ preferably a chain-like or cyclic alkyl group having 1 to 30 carbon atoms.

The alkenyl group for $R^{201}$ to $R^{207}$, $R^{211}$ and $R^{212}$ preferably has 2 to 10 carbon atoms.

Specific examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, an arylthio group and groups represented by formulae (ca-r-1) to (ca-r-7) shown below.

The aryl group within the arylthio group as the substituent is the same as defined for $R^{101}$, and specific examples include a phenylthio group and a biphenylthio group.

[Chemical Formula 69.]

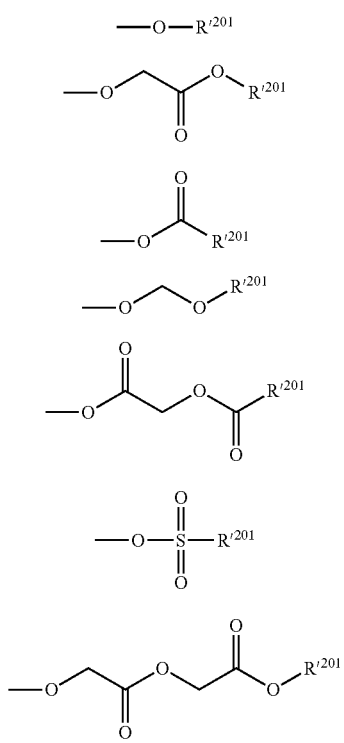

In the formulae, $R'^{201}$ each independently represents a hydrogen atom, a cyclic group which may have a substituent, a chain-like alkyl group which may have a substituent or a chain-like alkenyl group which may have a substituent.

As the cyclic group which may have a substituent, the chain-like alkyl group which may have a substituent and the chain-like alkenyl group which may have a substituent for $R'^{201}$ the same groups as those described above for $R^{101}$ can be mentioned.

As the cyclic group which may have a substituent and chain-like alkyl group which may have a substituent, the same groups as those described above for the acid dissociable group represented by the aforementioned formula (a1-r-2) can be also mentioned.

When $R^{201}$ to $R^{203}$, $R^{206}$, $R^{207}$, $R^{211}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(R$_N$)— (wherein R$_N$ represents an alkyl group of 1 to 5 carbon atoms). The ring containing the sulfur atom in the skeleton thereof is preferably a 3 to 10-membered ring, and most preferably a 5 to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

$R^{208}$ and $R^{209}$ each independently represents a hydrogen atom or an alkyl group of 1 to 5 carbon atoms, preferably a hydrogen atom or an alkyl group of 1 to 3 carbon atoms, and when $R^{208}$ and $R^{209}$ each represents an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent, or an —SO$_2$— containing cyclic group which may have a substituent.

Examples of the aryl group for $R^{210}$ include an unsubstituted aryl group of 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms.

As the —SO$_2$— containing cyclic group for $R^{210}$ which may have a substituent, the same "—SO$_2$— containing cyclic groups" as those described above may be mentioned, and a group represented by the aforementioned general formula (a5-r-1) is preferable.

Each $Y^{201}$ independently represents an arylene group, an alkylene group or an alkenylene group.

Examples of the arylene group for $Y^{201}$ include groups in which one hydrogen atom has been removed from an aryl group given as an example of the aromatic hydrocarbon group for $R^{101}$ in the aforementioned formula (b-1).

The alkylene group and the alkenylene group for $Y^{201}$ is the same as defined for the aliphatic hydrocarbon group as the divalent linking group represented by Va$^1$ in the aforementioned general formula (a1-1).

In the formula (ca-4), x represents 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups as those described above for Ya$^{21}$ in the general formula (a2-1) can be mentioned. The divalent linking group for $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly desirable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Specific examples of preferable cations represented by formula (ca-1) include cations represented by formulae (ca-1-1) to (ca-1-63) shown below.

[Chemical Formula 70.]
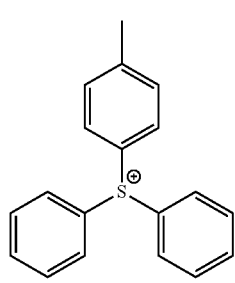 (ca-1-1)
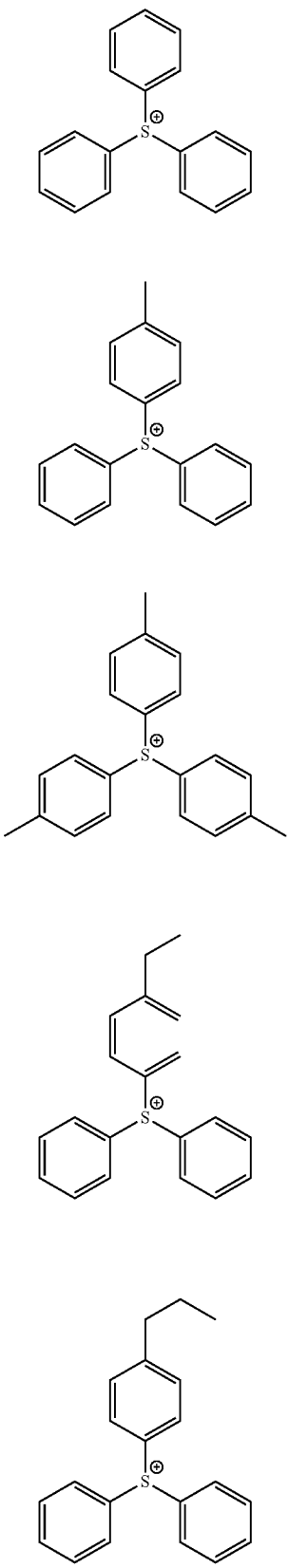
(ca-1-2)
(ca-1-3)
(ca-1-4)
(ca-1-5)
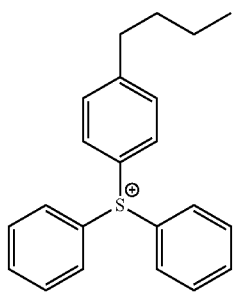 (ca-1-6)
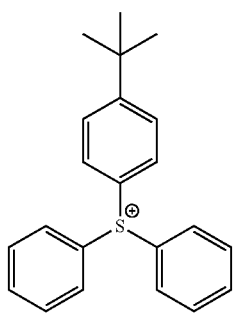 (ca-1-7)
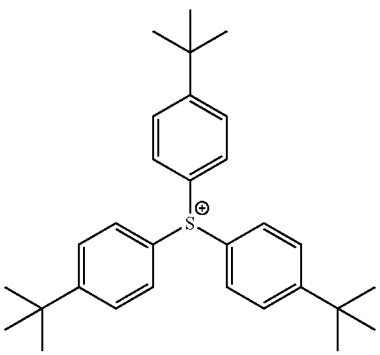 (ca-1-8)
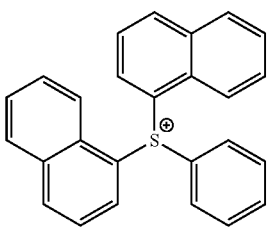 (ca-1-9)
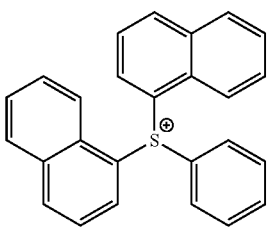 (ca-1-10)

(ca-1-11)
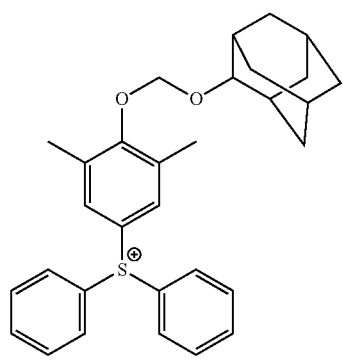
(ca-1-12)
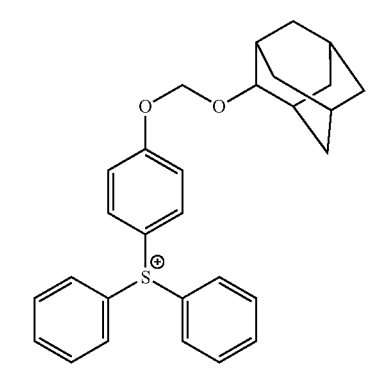
(ca-1-13)
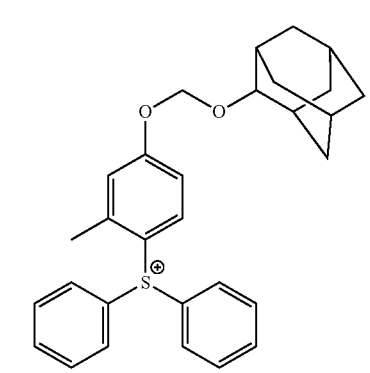
(ca-1-14)
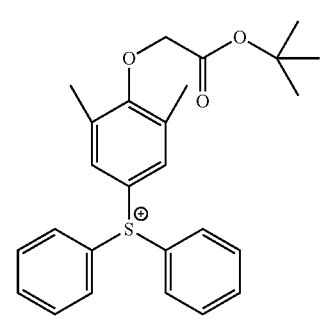
(ca-1-15)
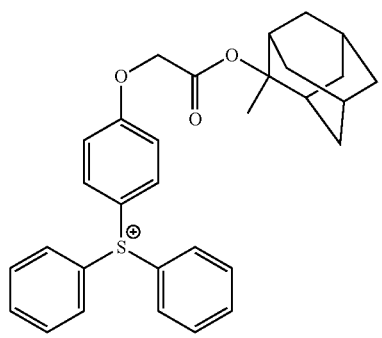
(ca-1-16)
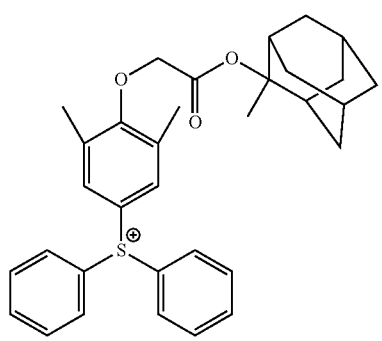
[Chemical Formula 71.]
(ca-1-17)
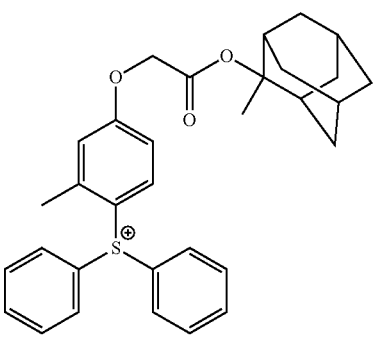
(ca-1-18)
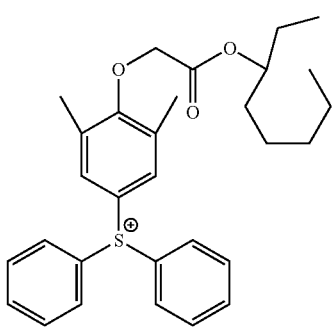

115
-continued
(ca-1-19)
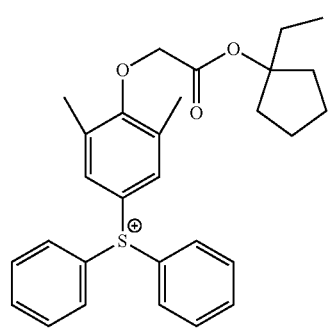
(ca-1-20)
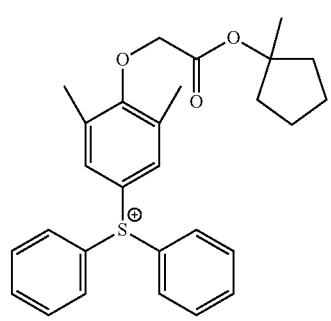
(ca-1-21)
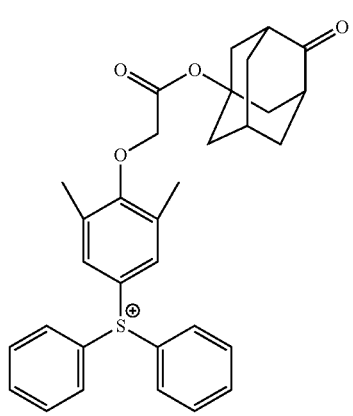
(ca-1-22)
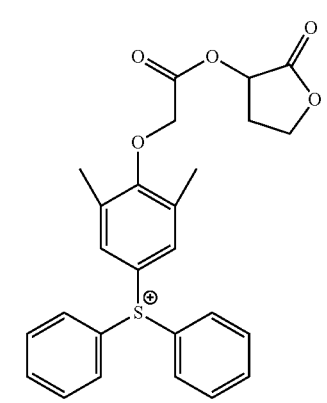
116
-continued
(ca-1-23)
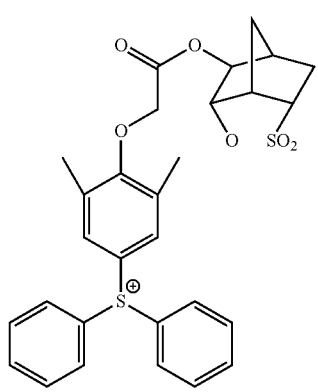
(ca-1-24)
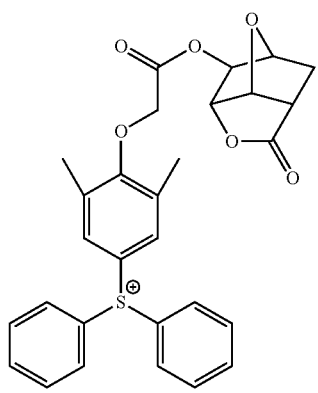
(ca-1-25)
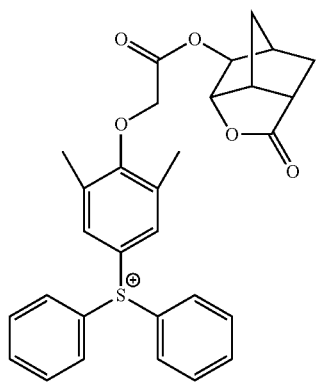
(ca-1-26)
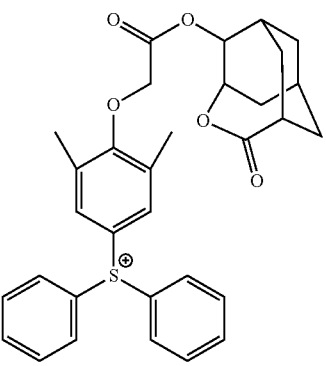

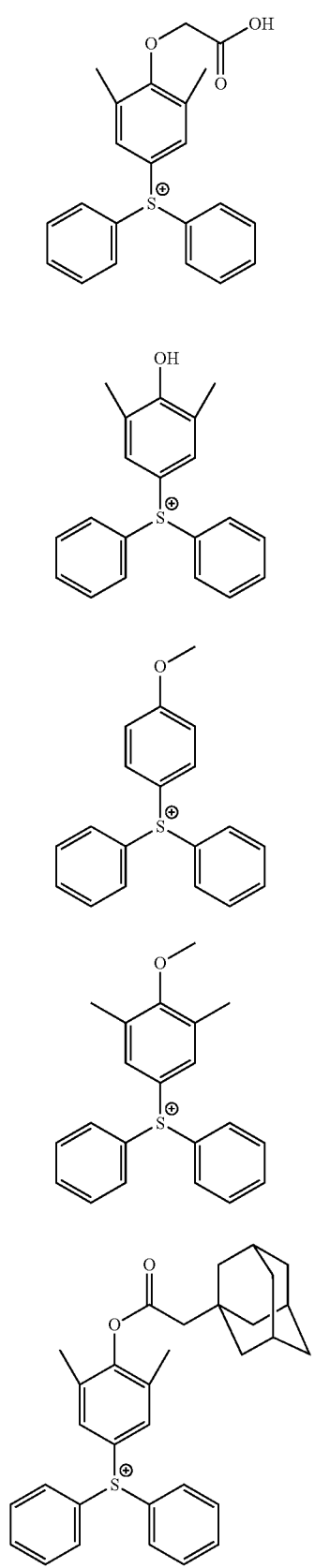
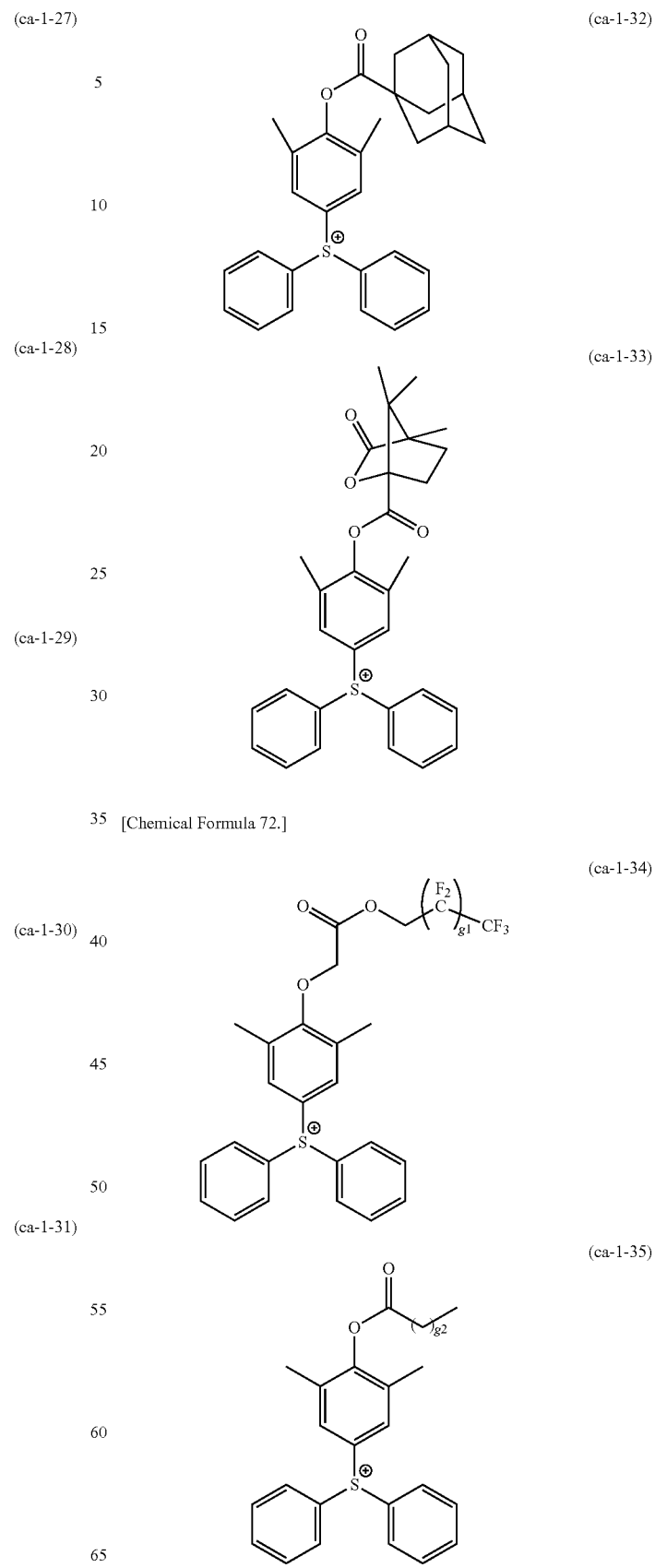
[Chemical Formula 72.]

(ca-1-36)
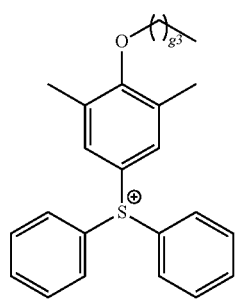
(ca-1-37)
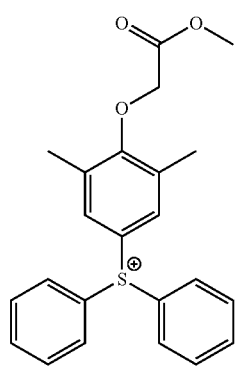
(ca-1-38)
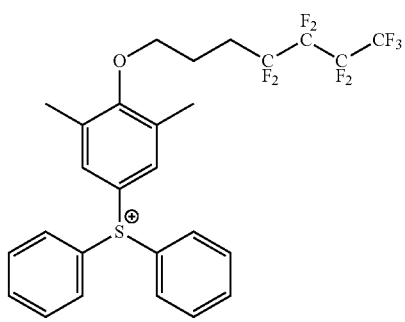
(ca-1-39)
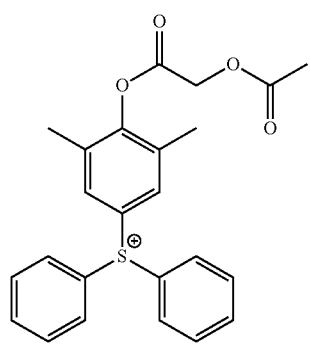
(ca-1-40)
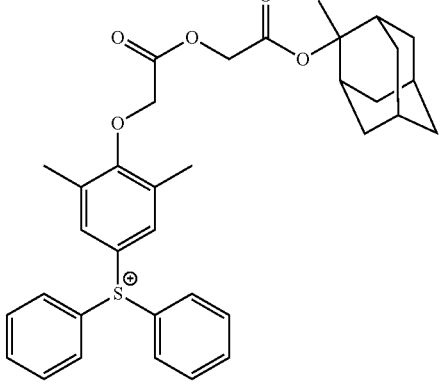
(ca-1-41)
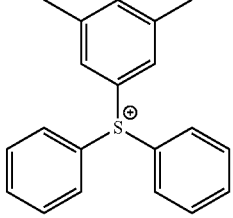
(ca-1-42)
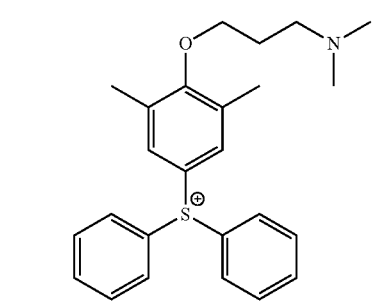
(ca-1-43)
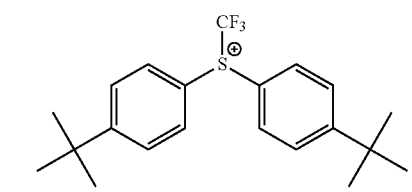
(ca-1-44)
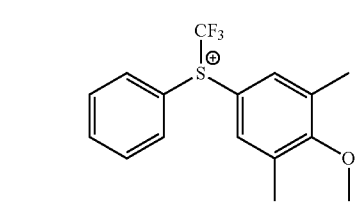
(ca-1-45)
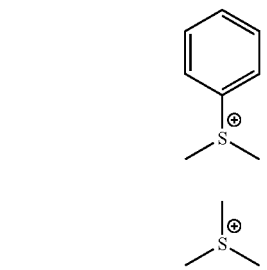
(ca-1-46)

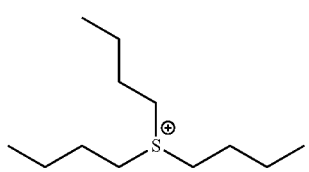 (ca-1-47)
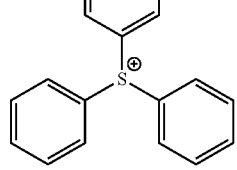 (ca-1-48)
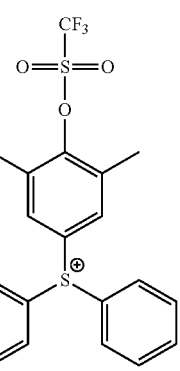
In the formulae, g1, g2 and g3 represent recurring numbers, wherein g1 is an integer of 1 to 5, g2 is an integer of 0 to 20, and g3 is an integer of 0 to 20.
[Chemical Formula 73.]
(ca-1-49)
(ca-1-50)
(ca-1-51)
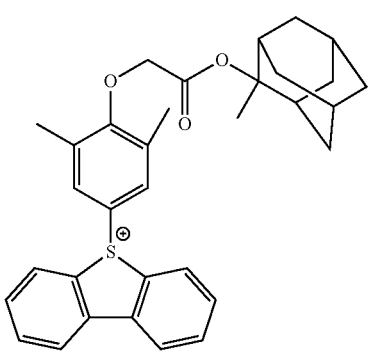 (ca-1-52)
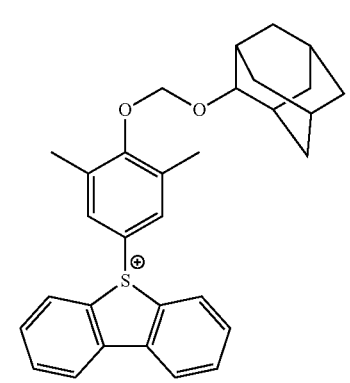 (ca-1-53)
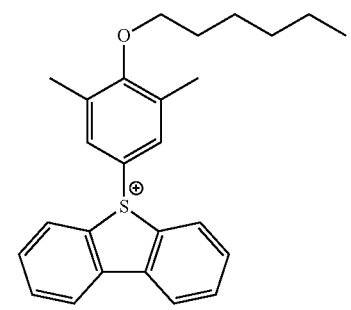 (ca-1-54)
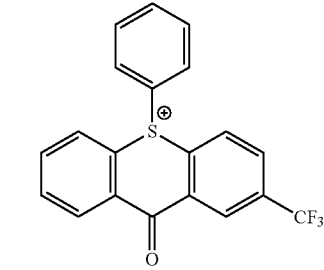 (ca-1-55)
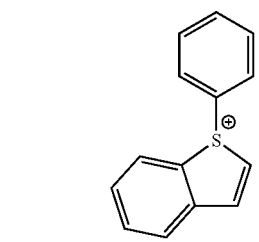 (ca-1-56)

(ca-1-57)

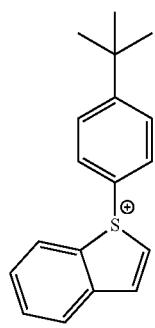

(ca-1-58)

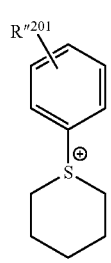

(ca-1-59)

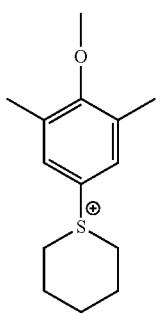

(ca-1-60)

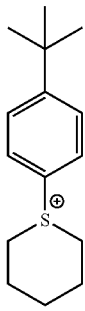

(ca-1-61)

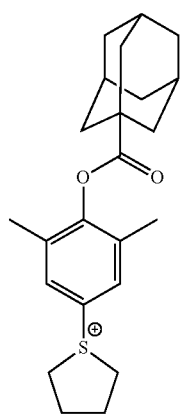

(ca-1-62)

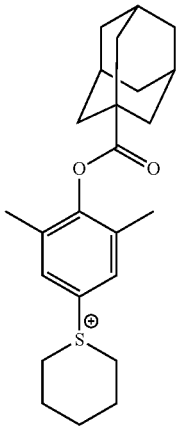

(ca-1-63)

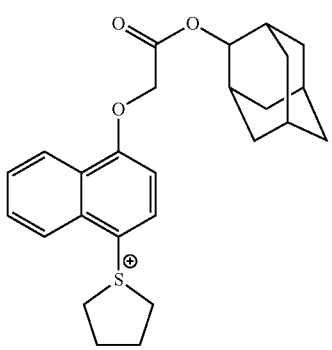

In the formulae, $R''^{201}$ represents a hydrogen atom or a substituent, and as the substituent, the same groups as those described above for substituting $R^{201}$ to $R^{207}$ and $R^{210}$ to $R^{212}$ can be mentioned.

Specific examples of preferable cations represented by formula (ca-3) include cations represented by formulae (ca-3-1) to (ca-3-6) shown below.

[Chemical Formula 74.]

(ca-3-1)

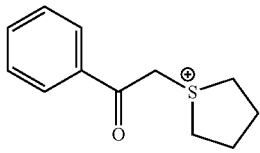

(ca-3-2)

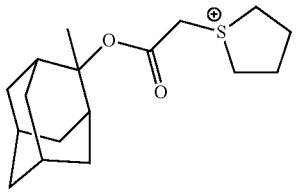

(ca-3-3)

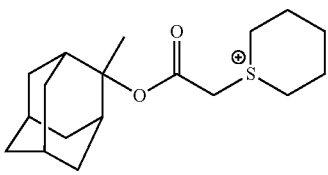

(ca-3-4)
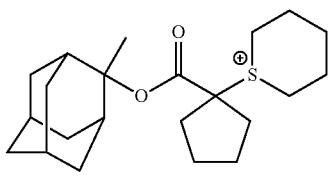

(ca-3-5)
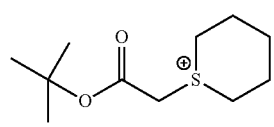

(ca-3-6)
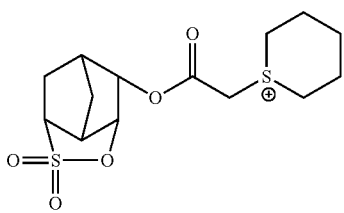

Specific examples of preferable cations represented by formula (ca-4) include cations represented by formulae (ca-4-1) and (ca-4-2) shown below.

[Chemical Formula 75.]

(ca-4-1)

(ca-4-2)

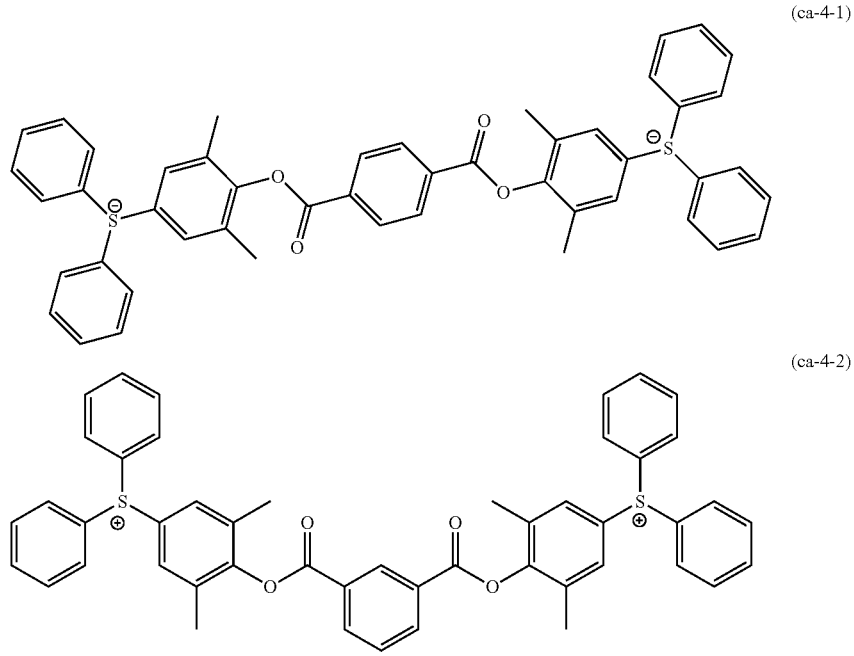

As the component (B), one kind of these acid generators may be used alone, or two or more kinds may be used in combination.

In the present embodiment, when the resist composition contains the component (B), the amount of the component (B) relative to 100 parts by weight of the component (A) is preferably within a range from 0.5 to 60 parts by weight, more preferably from 1 to 50 parts by weight, and still more preferably from 1 to 40 parts by weight.

When the amount of the component (B) is within the above-mentioned range, formation of a resist pattern can be satisfactorily performed. Further, by virtue of the above-mentioned range, when each of the components are dissolved in an organic solvent, a uniform solution can be obtained and the storage stability becomes satisfactory.

<<Other Components>>

In the present embodiment, the resist composition may further contain, in addition to the component (A), or in addition to the component (A) and (B), any other optional components.

Examples of the other components include the component (D), the component (E) and the component (S) described below.

Component (D):

In the present embodiment, the resist composition may further contain an acid diffusion control agent (hereafter, referred to as "component (D)").

The component (D) functions as an acid diffusion control agent, i.e., a quencher which traps the acid generated from the component (B) and the like upon exposure.

In the present embodiment, the component (D) may be a photodecomposable base (D1) (hereafter, referred to as "component (D1)") which is decomposed upon exposure and then loses the ability of controlling of acid diffusion, or a nitrogen-containing organic compound (D2) (hereafter, referred to as "component (D2)") which does not fall under the definition of component (D1).

Component (D1)

When a resist pattern is formed using a resist composition containing the component (D1), the contrast between exposed portions and unexposed portions is improved.

The component (D1) is not particularly limited, as long as it is decomposed upon exposure and then loses the ability of controlling of acid diffusion. As the component (D1), at least one compound selected from the group consisting of a compound represented by general formula (d1-1) shown below (hereafter, referred to as "component (d1-1)"), a compound represented by general formula (d1-2) shown below (hereafter, referred to as "component (d1-2)") and a compound represented by general formula (d1-3) shown below (hereafter, referred to as "component (d1-3)") is preferably used.

At exposed portions, the components (d1-1) to (d1-3) are decomposed and then lose the ability of controlling of acid diffusion (i.e., basicity), and therefore the components (d1-1) to (d1-3) cannot function as a quencher, whereas at unexposed portions, the components (d1-1) to (d1-3) functions as a quencher.

[Chemical Formula 76.]

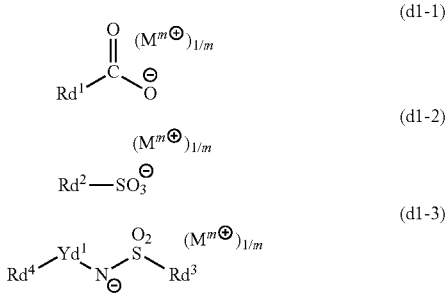

In the formulae, $Rd^1$ to $Rd^4$ represent a cyclic group which may have a substituent, a chain-like alkyl group which may have a substituent or a chain-like alkenyl group which may have a substituent, provided that, the carbon atom adjacent to the sulfur atom within the $Rd^2$ in the formula (d1-2) has no fluorine atom bonded thereto; $Yd^1$ represents a single bond or a divalent linking group; and $M^{m+}$ each independently represents a cation having a valency of m.

{Component (d1-1)}
Anion Moiety

In formula (d1-1), $Rd^1$ represents a cyclic group which may have a substituent, a chain-like alkyl group which may have a substituent or a chain-like alkenyl group which may have a substituent, and is the same groups as those defined above for $R^{101}$.

Among these, as the group for $Rd^1$, an aromatic hydrocarbon group which may have a substituent, an aliphatic cyclic group which may have a substituent and a chain-like hydrocarbon group which may have a substituent are preferable. As the substituents which these groups may have, a fluorine atom or a fluorinated alkyl group is preferable.

The aromatic hydrocarbon group is preferably a phenyl group or a naphthyl group.

Examples of the aliphatic cyclic group include groups in which one or more hydrogen atoms have been removed from a polycycloalkane such as adamantane, norbornane, isobornane, tricyclodecane or tetracyclododecane.

As the chain-like hydrocarbon group, a chain-like alkyl group is preferable. The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

In the case where the chain-like alkyl group is a fluorinated alkyl group having a fluorine atom or a fluorinated alkyl group, the fluorinated alkyl group preferably has 1 to 11 carbon atoms, more preferably 1 to 8 carbon atoms, and still more preferably 1 to 4 carbon atoms. The fluorinated alkyl group may contain an atom other than fluorine. Examples of the atom other than fluorine include an oxygen atom, a carbon atom, a hydrogen atom, a sulfur atom and a nitrogen atom.

As $Rd^1$, a fluorinated alkyl group in which part or all of the hydrogen atoms constituting a linear alkyl group have been substituted with fluorine atom(s) is preferable, and a fluorinated alkyl group in which all of the hydrogen atoms constituting a linear alkyl group have been substituted with fluorine atoms (i.e., a linear perfluoroalkyl group) is more preferable.

Specific examples of preferable anion moieties for the component (d1-1) are shown below.

[Chemical Formula 77.]

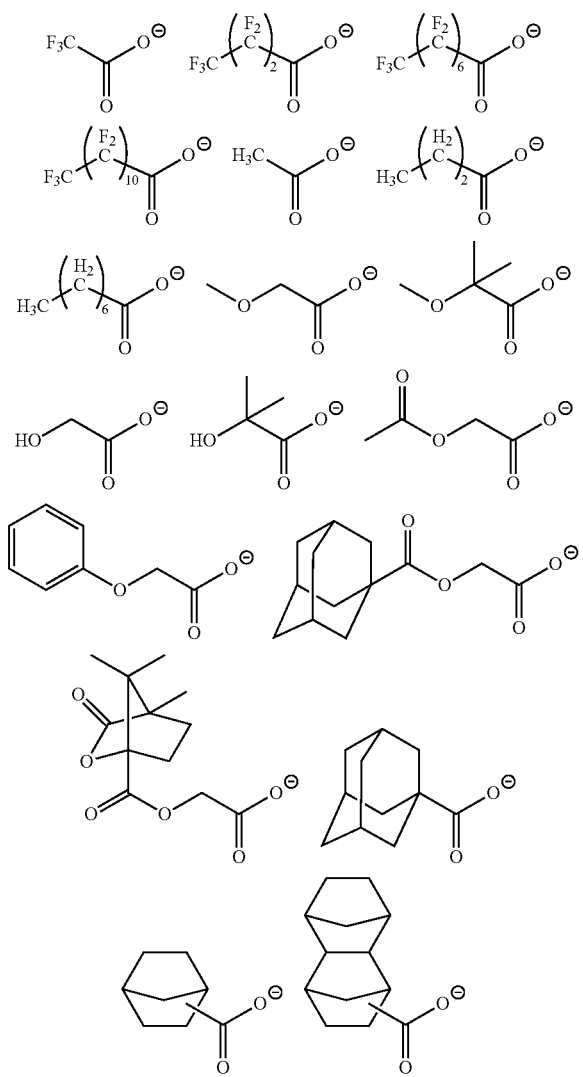

-continued

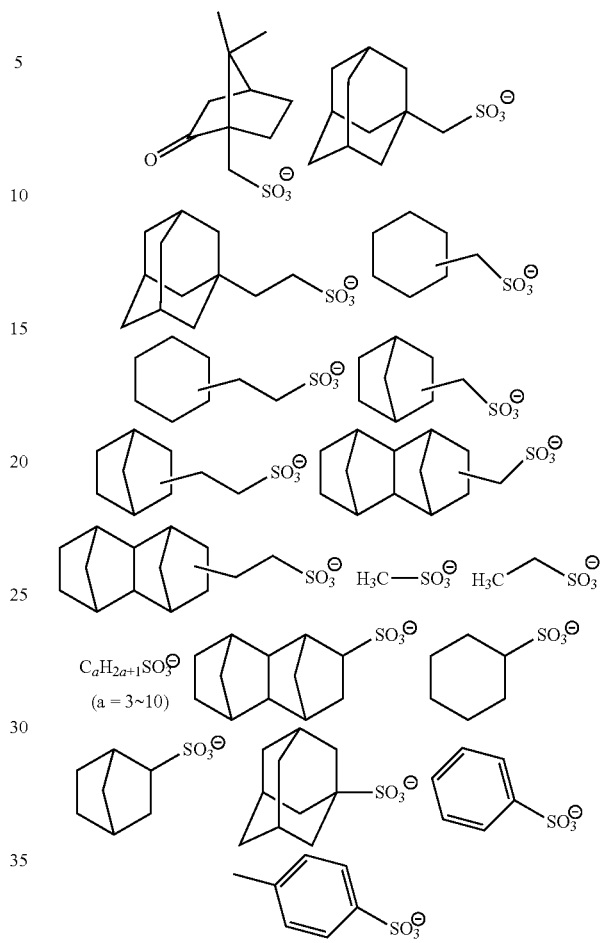

[Chemical Formula 78.]

Cation Moiety

In formula (d1-1), $M^{m+}$ represents an organic cation having a valency of m.

The organic cation for $M^{m+}$ is not particularly limited, and examples thereof include the same cation moieties as those represented by the aforementioned formulas (ca-1) to (ca-4), and cation moieties represented by the aforementioned formulas (ca-1-1) to (ca-1-63) are preferable.

As the component (d1-1), one kind of compound may be used, or two or more kinds of compounds may be used in combination.

{Component (d1-2)}

Anion Moiety

In formula (d1-2), $Rd^2$ represents a cyclic group which may have a substituent, a chain-like alkyl group which may have a substituent or a chain-like alkenyl group which may have a substituent, and is the same groups as those defined above for $R^{101}$, provided that, the carbon atom adjacent to the sulfur atom within $Rd^2$ group has no fluorine atom bonded thereto (i.e., the carbon atom adjacent to the sulfur atom within $Rd^2$ group does not substituted with a fluorine atom). As a result, the anion of the component (d1-2) becomes an appropriately weak acid anion, thereby improving the quenching ability of the component (D).

As $Rd^2$, an aliphatic cyclic group which may have a substituent is preferable, and a group in which one or more hydrogen atoms have been removed from adamantane, norbornane, isobornane, tricyclodecane, tetracyclododecane or camphor (which may have a substituent) is more preferable.

The hydrocarbon group for $Rd^2$ may have a substituent. As the substituent, the same groups as those described above for substituting the hydrocarbon group (e.g., aromatic hydrocarbon group, aliphatic hydrocarbon group) for $Rd^{101}$ in the formula (d1-1) can be mentioned.

Specific examples of preferable anion moieties for the component (d1-2) are shown below.

Cation Moiety

In formula (d1-2), $M^{m+}$ is an organic cation having a valency of m, and is the same as defined for $M^{m+}$ in the aforementioned formula (d1-1).

As the component (d1-2), one kind of compound may be used, or two or more kinds of compounds may be used in combination.

{Component (d1-3)}

Anion Moiety

In formula (d1-3), $Rd^3$ represents a cyclic group which may have a substituent, a chain-like alkyl group which may have a substituent or a chain-like alkenyl group which may have a substituent, and is the same groups as those defined above for $R^{101}$, and a cyclic group containing a fluorine atom, a chain-like alkyl group or a chain-like alkenyl group is preferable. Among these, a fluorinated alkyl group is preferable, and more preferably the same fluorinated alkyl groups as those described above for $Rd^1$.

In formula (d1-3), $Rd^4$ represents a cyclic group which may have a substituent, a chain-like alkyl group which may have a substituent or a chain-like alkenyl group which may have a substituent, and is the same groups as those defined above for $R^{101}$.

Among these, an alkyl group which may have substituent, an alkoxy group which may have substituent, an alkenyl group which may have substituent or a cyclic group which may have substituent is preferable.

The alkyl group for $Rd^4$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $Rd^4$ may be substituted with a hydroxy group, a cyano group or the like.

The alkoxy group for $Rd^4$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are preferable.

As the alkenyl group for $Rd^4$, the same groups as those described above for $R^{101}$ can be mentioned, and a vinyl group, a propenyl group (an allyl group), a 1-methylpropenyl group and a 2-methylpropenyl group are preferable. These groups may have an alkyl group of 1 to 5 carbon atoms or a halogenated alkyl group of 1 to 5 carbon atoms as a substituent.

As the cyclic group for $Rd^4$, the same groups as those described above for $R^{101}$ can be mentioned. Among these, as the cyclic group, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $Rd^4$ is an alicyclic group, the resist composition can be satisfactorily dissolved in an organic solvent, thereby improving the lithography properties. Alternatively, when $Rd^4$ is an aromatic group, the resist composition exhibits an excellent photoabsorption efficiency in a lithography process using EUV or the like as the exposure source, thereby resulting in the improvement of the sensitivity and the lithography properties.

In formula (d1-3), $Yd^1$ represents a single bond or a divalent linking group.

The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. As such groups, the same divalent linking groups as those described above for $Ya^{21}$ in the formula (a2-1) can be mentioned.

As $Yd^1$, a carbonyl group, an ester bond, an amide bond, an alkylene group or a combination of these is preferable. As the alkylene group, a linear or branched alkylene group is more preferable, and a methylene group or an ethylene group is still more preferable.

Specific examples of preferable anion moieties for the component (d1-3) are shown below.

[Chemical Formula 79.]

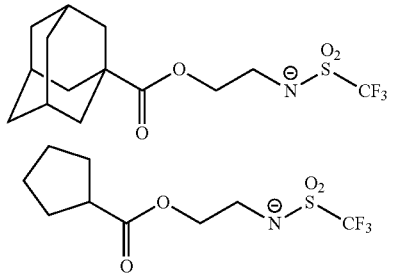

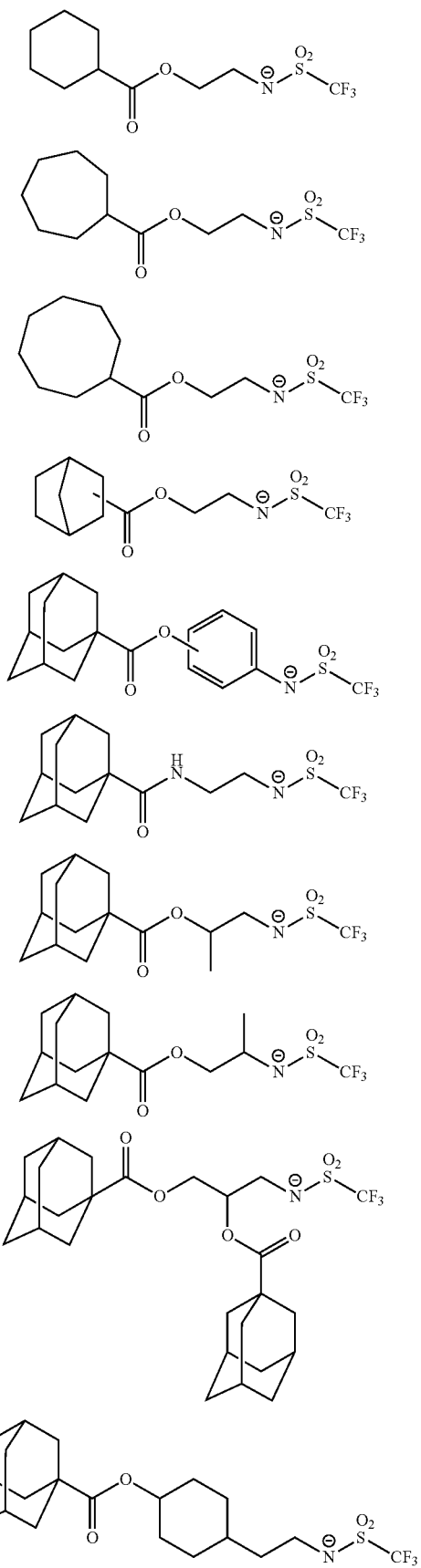

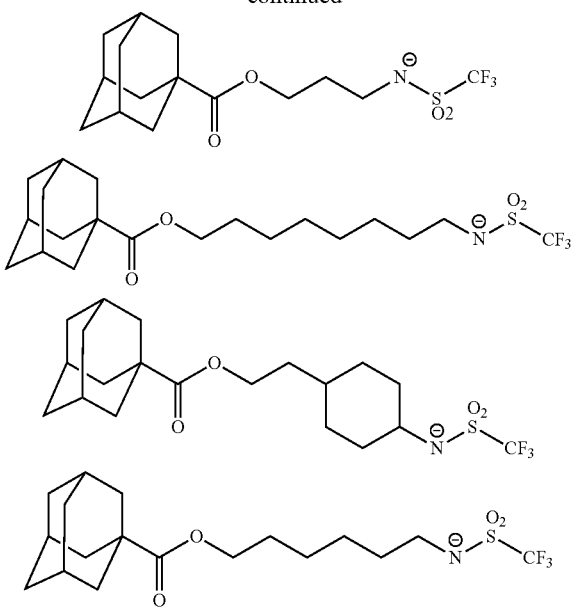

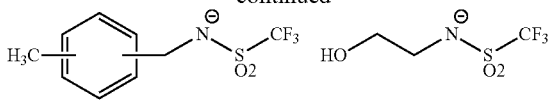

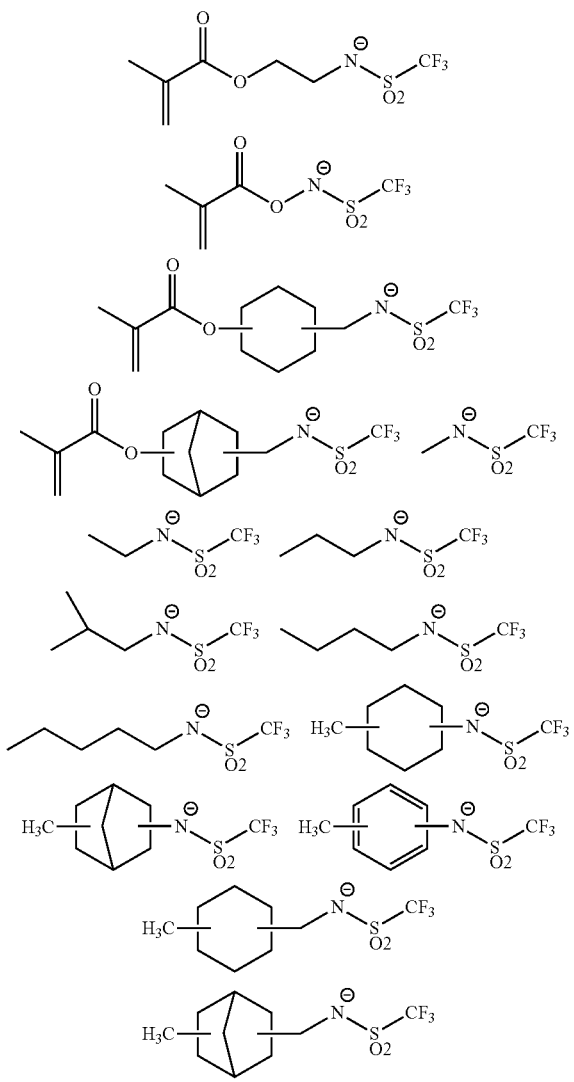

Cation Moiety

In formula (d1-3), $M^{m+}$ is an organic cation having a valency of m, and is the same as defined for $M^{m+}$ in the aforementioned formula (d1-1).

As the component (d1-3), one kind of compound may be used, or two or more kinds of compounds may be used in combination.

As the component (D1), one kind of the aforementioned components (d1-1) to (d1-3), or at least two kinds of the aforementioned components (d1-1) to (d1-3) can be used in combination.

The amount of the component (D1) relative to 100 parts by weight of the component (A) is preferably within a range from 0.5 to 10 parts by weight, more preferably from 0.5 to 8 parts by weight, and still more preferably from 1 to 8 parts by weight.

When the amount of the component (D1) is at least as large as the lower limit of the above-mentioned range, excellent lithography properties and excellent resist pattern shape can be obtained. On the other hand, when the amount of the component (D1) is no more than the upper limit of the above-mentioned range, sensitivity can be maintained at a satisfactory level, and through-put becomes excellent.

The production methods of the components (d1-1) and (d1-2) are not particularly limited, and the components (d1-1) and (d1-2) can be produced by conventional methods.

The amount of the component (D1) relative to 100 parts by weight of the component (A) is preferably within a range from 0.5 to 10.0 parts by weight, more preferably from 0.5 to 8.0 parts by weight, and still more preferably from 1.0 to 8.0 parts by weight. When the amount of at least as large as the lower limit of the above-mentioned range, excellent lithography properties and excellent resist pattern shape can be obtained. On the other hand, when the amount of the component (D) is no more than the upper limit of the above-mentioned range, sensitivity can be maintained at a satisfactory level, and through-put becomes excellent.

Component (D2)

The component (D) may contain a nitrogen-containing organic compound (D2) (hereafter, referred to as component (D2)) which does not fall under the definition of component (D1).

The component (D2) is not particularly limited, as long as it functions as an acid diffusion control agent, and does not fall under the definition of the component (D1). As the component (D2), any of the conventionally known compounds may be selected for use. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine;

dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxy ethoxy)ethyl}amine, tris{2-(2-methoxyethoxymethoxy)ethyl}amine, tris{2-(1-methoxy ethoxy)ethyl}amine, tris{2-(1-ethoxy ethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D2), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (D2), one kind of compound may be used alone, or two or more kinds may be used in combination.

The component (D2) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

As the component (D), one kind of compound may be used, or two or more kinds of compounds may be used in combination.

In the present embodiment, when the resist composition contains the component (D), the amount of the component (D) relative to 100 parts by weight of the component (A) is preferably within a range from 0.1 to 15 parts by weight, more preferably from 0.3 to 12 parts by weight, and still more preferably from 0.5 to 12 parts by weight.

When the amount of the component (D) is at least as large as the lower limit of the above-mentioned range, various lithography properties (such as LWR) of the resist composition are improved. Further, a resist pattern having an excellent shape can be obtained. On the other hand, when the amount of the component (D) is no more than the upper limit of the above-mentioned range, sensitivity can be maintained at a satisfactory level, and through-put becomes excellent.

Component (E):

Furthermore, in the resist composition of the present embodiment, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof may be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

As the component (E), one kind may be used alone, or two or more kinds may be used in combination.

The component (E) is typically used in an amount within a range from 0.01 to 5.0 parts by weight, relative to 100 parts by weight of the component (A).

Component (S):

In the present embodiment, the resist composition can be prepared by dissolving the materials for the resist composition in an organic solvent (hereafter, frequently referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone (MEK), cyclohexanone, methyl-n-pentyl ketone (2-heptanone), and methyl isopentyl ketone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These solvents can be used individually, or in combination as a mixed solvent.

Among these, PGMEA, PGME, γ-butyrolactone and EL are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL or cyclohexanone weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate In general, the organic solvent is used in an amount such that the solid content of the resist composition becomes within the range from 1 to 20% by weight, and preferably from 2 to 15% by weight.

If desired, other miscible additives can also be added to the resist composition of the present invention. Examples of such miscible additives include additive resins for improving the performance of the resist film, dissolution inhibitors, plasticizers, stabilizers, colorants, halation prevention agents, and dyes.

(Method of Forming a Resist Pattern)

The method of forming a resist pattern according to the present embodiment includes: forming a resist film on a substrate using a resist composition of the aforementioned embodiment; conducting exposure of the resist film; and developing the resist film to form a resist pattern.

The method for forming a resist pattern according to the present embodiment can be performed, for example, as follows.

Firstly, a resist composition of the first aspect is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment. The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing.

In this manner, a resist pattern can be formed.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present embodiment is effective to KrF excimer laser, ArF excimer laser, EB and EUV, and more effective to ArF excimer laser, EB and EUV, and most effective to EB and EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium)

that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used which are capable of dissolving the component (A) (prior to exposure). Specific examples of the organic solvent include polar solvents such as ketone solvents, ester solvents, alcohol solvents, nitrile solvents, amide solvents and ether solvents, and hydrocarbon solvents.

A ketone solvent is an organic solvent containing C—C(=O)—C within the structure thereof. An ester solvent is an organic solvent containing C—C(=O)—O—C within the structure thereof. An alcohol solvent is an organic solvent containing an alcoholic hydroxy group in the structure thereof. An "alcoholic hydroxy group" refers to a hydroxy group bonded to a carbon atom of an aliphatic hydrocarbon group. A nitrile solvent is an organic solvent containing a nitrile group in the structure thereof. An amide solvent is an organic solvent containing an amide group within the structure thereof. An ether solvent is an organic solvent containing C—O—C within the structure thereof.

Some organic solvents have a plurality of the functional groups which characterizes the aforementioned solvents within the structure thereof. In such a case, the organic solvent can be classified as any kind of the solvent having the characteristic functional group. For example, diethyleneglycol monomethylether can be classified as either an alcohol solvent or an ether solvent.

A hydrocarbon solvent consists of a hydrocarbon which may be halogenated, and does not have any substituent other than a halogen atom. Examples of the halogen atom include a fluorine atom, a chlorine atom, a bromine atom and an iodine atom, and a fluorine atom is preferable.

As the organic solvent contained in the organic developing solution, among these, a polar solvent is preferable, and ketone solvents, ester solvents and nitrile solvents are preferable.

Examples of ketone solvents include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonylalcohol, acetylcarbinol, acetophenone, methyl naphthyl ketone, isophorone, propylenecarbonate, γ-butyrolactone and methyl amyl ketone (2-heptanone). Among these examples, as a ketone solvent, methyl amyl ketone (2-heptanone) is preferable.

Examples of ester solvents include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate and propyl-3-methoxypropionate. Among these examples, as an ester solvent, butyl acetate is preferable.

Examples of nitrile solvents include acetonitrile, propionitrile, valeronitrile, butyronitrile and the like.

If desired, the organic developing solution may have a conventional additive blended. Examples of the additive include surfactants. The surfactant is not particularly limited, and for example, an ionic or non-ionic fluorine and/or silicon surfactant can be used.

As the surfactant, a non-ionic surfactant is preferable, and a non-ionic fluorine surfactant or a non-ionic silicon surfactant is more preferable.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly desirable.

The alcohol solvent used for the rinse liquid is preferably a monohydric alcohol of 6 to 8 carbon atoms, and the monohydric alcohol may be linear, branched or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol and benzyl alcohol. Among these, 1-hexanol, 2-heptanol and 2-hexanol are preferable, and 1 hexanol and 2-hexanol are more preferable.

As the organic solvent, one kind of solvent may be used alone, or two or more kinds of solvents may be used in combination. Further, an organic solvent other than the aforementioned examples or water may be mixed together. However, in consideration of the development characteristics, the amount of water within the rinse liquid, based on the total amount of the rinse liquid is preferably 30% by weight or less, more preferably 10% by weight or less, still more preferably 5% by weight or less, and most preferably 3% by weight or less.

If desired, the rinse solution may have a conventional additive blended. Examples of the additive include surfactants. Examples of the additive include surfactants. As the surfactant, the same surfactants as those described above can be mentioned, a non-ionic surfactant is preferable, and a non-ionic fluorine surfactant or a non-ionic silicon surfactant is more preferable.

When a surfactant is added, the amount thereof based on the total amount of the rinse liquid is generally 0.001 to 5% by weight, preferably 0.005 to 2% by weight, and more preferably 0.01 to 0.5% by weight.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

As described above, the resist composition according to the present embodiment contains the base component (A) and the fluorine additive component (F).

The component (F) contains the fluorine resin component (F1) having the structural unit (f1) and the structural unit (f2). In EUV lithography or EB lithography, it is required to not only improve various lithography properties, but also suppress generation of defects. One of the causes of the generation of defects is considered to be deposited substance during developing process (e.g., a substance hardly soluble in an alkali developing solution) adhering to the surface of the resist pattern. The component (F1) which segregates on the surface of the pattern is decomposed by action of a base (e.g., an alkali developing solution), and a hydrophilic group is generated. Therefore, the component (F1) can be hydrophilized during developing. As a result, it is presumed that adhesion of deposited substance and the like can be suppressed, and generation of defects can be reduced.

Further, the structural unit (f2) has a structure which is highly hydrophilic itself, and is also highly hydrophilic after developing (after alkali decomposition). Therefore, by virtue of using the component (F1) having the structural unit (f1) and the structural unit (f2), not only is the component (F1) segregated on the surface of the resist by the structural unit (f1), but also the surface of the resist is hydrophilized by the structural unit ($f^2$).

As a result, it is presumed that defects on the surface of the resist can be reduced. Further, by virtue of the component (F1) having the structural unit (f2) which is highly hydrophilic, the affinity of the resist composition for the developing solution is enhanced, thereby contributing to improvement of various lithography properties such as resolution and LWR.

EXAMPLES

As follows is a description of examples of the present invention, although the scope of the present invention is by no way limited by these examples.

Polymer Synthesis Example

The following monomers (02), (10), (01) and (03) were subjected to radical polymerization with the molar ratio shown in Table 1, so as to obtain polymers (A)-1 to (A)-6.

With respect to the polymers (A)-1 to (A)-6, the compositional ratio of the polymers (the molar ratio of the respective structural units in the polymeric compound) as determined by $^{13}$C-NMR, the weight average molecular weight (Mw) and the polydispersity (Mw/Mn) determined by the polystyrene equivalent value as measured by GPC are also shown in Table 1.

[Chemical Formula 81.]

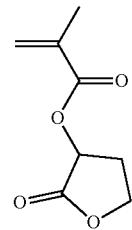

(02)

-continued

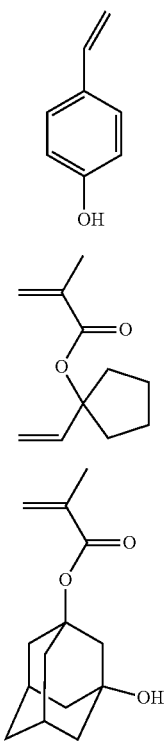

(10)

(01)

(03)

TABLE 1

| Polymer | Monomer (molar ratio) | | | | Mw | Mw/Mn |
| --- | --- | --- | --- | --- | --- | --- |
|  | (02) | (10) | (01) | (03) |  |  |
| (A)-1 | 20 | 20 | 50 | 10 | 7000 | 1.6 |
| (A)-2 | 30 | 20 | 40 | 10 | 7000 | 1.6 |
| (A)-3 | 40 | 20 | 30 | 10 | 7000 | 1.6 |
| (A)-4 | 40 | 10 | 40 | 10 | 7000 | 1.6 |
| (A)-5 | 30 | 20 | 40 | 10 | 7000 | 1.6 |
| (A)-6 | 50 | 0 | 40 | 10 | 7000 | 1.6 |

<Production of Resist Composition>

The components shown in Table 2 were mixed together and dissolved to obtain each resist composition.

TABLE 2

| | Component (A) | Component (B) | Component (D) | Component (F) | Component (S) |
| --- | --- | --- | --- | --- | --- |
| Example 1 | (A)-1 [100] | (B)-1 [14] | (D)-1 [3.0] | (F)-1 [3] | (S)-1 [70] |
| Comparative Example 1 | (A)-1 [100] | (B)-1 [14] | (D)-1 [3.0] | (F)-2 [3] | (S)-1 [70] |
| Example 2 | (A)-2 [100] | (B)-1 [14] | (D)-1 [3.0] | (F)-1 [3] | (S)-1 [70] |
| Comparative Example 2 | (A)-2 [100] | (B)-1 [14] | (D)-1 [3.0] | (F)-2 [3] | (S)-1 [70] |
| Example 3 | (A)-3 [100] | (B)-1 [14] | (D)-1 [3.0] | (F)-1 [3] | (S)-1 [70] |
| Comparative Example 3 | (A)-3 [100] | (B)-1 [14] | (D)-1 [3.0] | (F)-2 [3] | (S)-1 [70] |
| Example 4 | (A)-4 [100] | (B)-1 [14] | (D)-1 [3.0] | (F)-1 [3] | (S)-1 [70] |
| Comparative Example 4 | (A)-4 [100] | (B)-1 [14] | (D)-1 [3.0] | (F)-2 [3] | (S)-1 [70] |
| Example 5 | (A)-5 [100] | (B)-1 [14] | (D)-2 [1.5] | (F)-1 [3] | (S)-1 [70] |
| Comparative Example 5 | (A)-5 [100] | (B)-1 [14] | (D)-1 [3.0] | (F)-3 [3] | (S)-1 [70] |
| Comparative Example 6 | (A)-5 [100] | (B)-1 [14] | (D)-1 [3.0] | (F)-4 [3] | (S)-1 [70] |
| Comparative Example 7 | (A)-5 [100] | (B)-1 [14] | (D)-1 [3.0] | (F)-5 [3] | (S)-1 [v] |
| Comparative Example 8 | (A)-5 [100] | (B)-1 [14] | (D)-1 [3.0] | (F)-6 [3] | (S)-1 [70] |
| Comparative Example 9 | (A)-5 [100] | (B)-1 [14] | (D)-1 [3.0] | — | (S)-1 [70] |
| Example 6 | (A)-6 [100] | (B)-1 [14] | (D)-1 [3.0] | (F)-1 [3] | (S)-1 [70] |
| Comparative Example 10 | (A)-6 [100] | (B)-1 [14] | (D)-1 [3.0] | (F)-2 [3] | (S)-1 [70] |

In Table 2, the reference characters indicate the following. The values in brackets [ ] indicate the amount (in terms of parts by weight) of the component added.

(A)-1 to (A)-6: the aforementioned polymers (A)-1 to (A)-6

(B)-1: an acid generator represented by chemical formula (B)-1 shown below (D)-1: acid diffusion control agent represented by chemical formula (D)-1 below (F)-1: fluorine-containing polymeric compound represented by chemical formula (F)-1 below. The weight average molecular weight (Mw) and the dispersity (Mw/Mn) in terms of the polystyrene equivalent value measured by gel permeation chromatography (GPC) were 20,000 and 1.6, respectively. The composition of the copolymer (ratio (molar ratio) of the respective structural units within the structural formula) as determined by $^{13}$C-NMR was l/m=80/20.

(F)-2: fluorine-containing polymeric compound represented by chemical formula (F)-2 below. The weight average molecular weight (Mw) and the dispersity (Mw/Mn) in terms of the polystyrene equivalent value measured by gel permeation chromatography (GPC) were 20,000 and 1.6, respectively. The composition of the copolymer (ratio (molar ratio) of the respective structural units within the structural formula) as determined by $^{13}$C-NMR was l/m=80/20.

(F)-3: fluorine-containing polymeric compound (homopolymer) represented by chemical formula (F)-3 below. The weight average molecular weight (Mw) and the dispersity (Mw/Mn) in terms of the polystyrene equivalent value measured by gel permeation chromatography (GPC) were 20,000 and 1.6, respectively.

(F)-4: fluorine-containing polymeric compound represented by chemical formula (F)-4 below. The weight average molecular weight (Mw) and the dispersity (Mw/Mn) in terms of the polystyrene equivalent value measured by gel permeation chromatography (GPC) were 20,000 and 1.6, respectively. The composition of the copolymer (ratio (molar ratio) of the respective structural units within the structural formula) as determined by $^{13}$C-NMR was l/m/n=70/20/10.

(F)-5: fluorine-containing polymeric compound represented by chemical formula (F)-5 below. The weight average molecular weight (Mw) and the dispersity (Mw/Mn) in terms of the polystyrene equivalent value measured by gel permeation chromatography (GPC) were 20,000 and 1.6, respectively. The composition of the copolymer (ratio (molar ratio) of the respective structural units within the structural formula) as determined by $^{13}$C-NMR was l/m=70/30.

(F)-6: fluorine-containing polymeric compound represented by chemical formula (F)-6 below. The weight average molecular weight (Mw) and the dispersity (Mw/Mn) in terms of the polystyrene equivalent value measured by gel permeation chromatography (GPC) were 20,000 and 1.6, respectively. The composition of the copolymer (ratio (molar ratio) of the respective structural units within the structural formula) as determined by $^{13}$C-NMR was l/m=80/20.

(S)-1: a mixed solvent of propylene glycol monomethyl ether acetate/propylene glycol monomethyl ether=60/40 (weight ratio).

[Chemical Formula 82.]

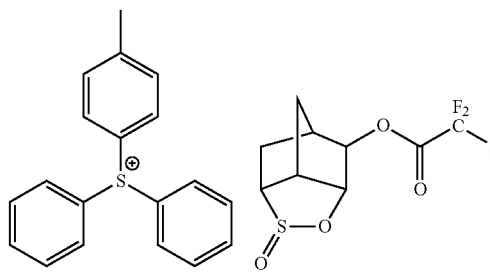
(B)-1

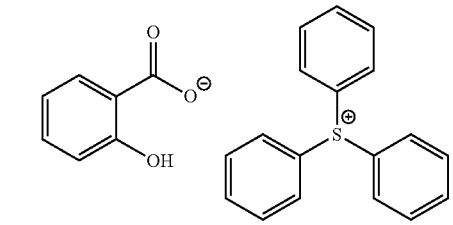
(D)-1

[Chemical Formula 83.]

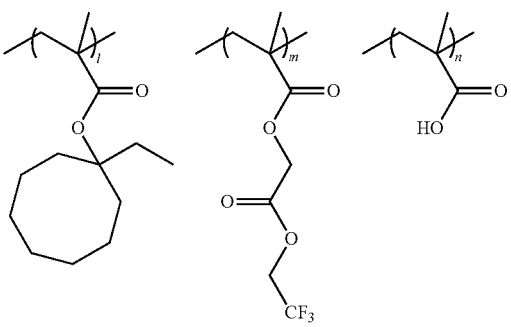
(F)-1

(F)-2

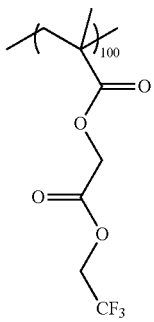
(F)-3

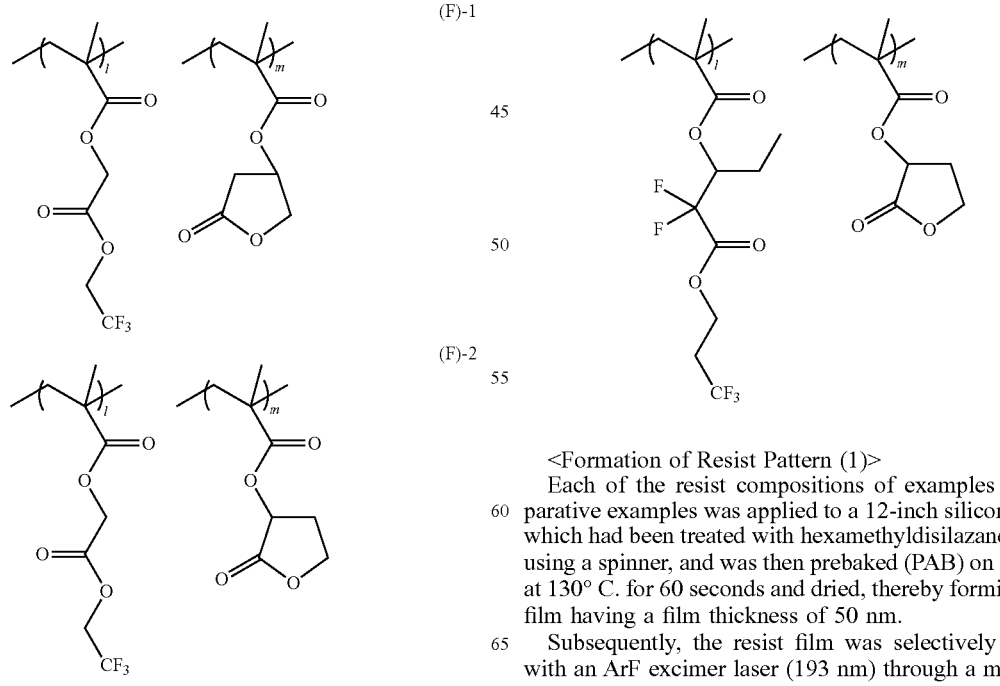
(F)-4

(F)-5

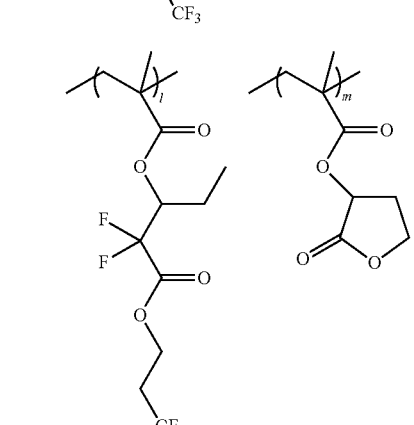
(F)-6

<Formation of Resist Pattern (1)>

Each of the resist compositions of examples and comparative examples was applied to a 12-inch silicon substrate which had been treated with hexamethyldisilazane (HMDS) using a spinner, and was then prebaked (PAB) on a hot plate at 130° C. for 60 seconds and dried, thereby forming a resist film having a film thickness of 50 nm.

Subsequently, the resist film was selectively irradiated with an ArF excimer laser (193 nm) through a mask, using an ArF exposure apparatus NSR-5308F (manufactured by Nikon Corporation, NA (numerical aperture)=0.92). Then, a post exposure bake (PEB) treatment was conducted at 130° C. for 60 seconds.

Thereafter, alkali developing was conducted for 10 seconds using a 2.38 wt % aqueous tetramethylammonium hydroxide (TMAH) solution "NMD-3" (product name; manufactured by Tokyo Ohka Kogyo Co., Ltd.) at 23° C.

Then, water rinsing was conducted for 15 seconds using pure water.

As a result, a 1:1 line and space pattern (LS pattern) having a line width of 65 nm was formed. The above procedure was conducted to form pseudo exposed portions which would be formed by EB or EUV exposure.

[Evaluation of Defect]

With respect to the large area unexposed portions adjacent to the pattern areas obtained in <Formation of resist pattern (1)>, the total number of defects within the wafer was determined using a surface defect observing apparatus (product name: KLA2371; manufactured by KLA Tencor). The results are shown in Table 3.

<Formation of Resist Pattern (2)>

Each of the resist compositions of examples and comparative examples was applied to a 12-inch silicon substrate which had been treated with hexamethyldisilazane (HMDS) using a spinner, and was then prebaked (PAB) on a hot plate at 110° C. for 60 seconds and dried, thereby forming a resist film having a film thickness of 30 nm.

Subsequently, the resist film was subjected to drawing (exposure) using an electron beam lithography apparatus JEOL-JBX-9300FS (manufactured by JEOL Ltd.) at an acceleration voltage of 100 kV, targeting a 1:1 line and space pattern (hereafter, referred to as "LS pattern") having lines with a width of 50 to 26 nm. Then, a post exposure bake (PEB) treatment was conducted at 110° C. for 60 seconds.

Thereafter, alkali developing was conducted for 60 seconds at 23° C. in a 2.38 wt % by weight aqueous solution of tetramethylammonium hydroxide (TMAH) (product name: NMD-3; manufactured by Tokyo Ohka Kogyo Co., Ltd.).

Then, water rinsing was conducted for 15 seconds using pure water.

As a result, a 1:1 LS pattern having a line width of 50 to 26 nm was formed.

[Evaluation of Resolution]

The critical resolution (nm) with the above Eop was determined using a scanning electron microscope (product name: S-9380, manufactured by Hitachi High-Technologies Corporation). Specifically, the exposure dose was gradually increased from the optimum exposure dose Eop, and the minimum size of the pattern which resolves without collapse (fall) was determined. The results are indicated under "Resolution performance (nm)" in Table 3.

[Evaluation of Line Width Roughness (LWR)]

With respect to the LS pattern formed in <Formation of resist pattern (2)>, 3σ was determined as a yardstick for LWR. The results are indicated under "LWR (nm)" in table.

"3σ" indicates a value of 3 times the standard deviation (σ) (i.e., 3σ) (unit: nm) determined by measuring the line positions at 400 points in the lengthwise direction of the line using a scanning electron microscope (product name: S-9380, manufactured by Hitachi High-Technologies Corporation; acceleration voltage: 800V).

The smaller this 3σ value is, the lower the level of roughness on the side walls of the line, indicating that an LS pattern with a uniform width was obtained.

TABLE 3

|  | Defect | Resolution (nm) | LWR (nm) |
| --- | --- | --- | --- |
| Example 1 | 500 | 30 | 6.5 |
| Comparative Example 1 | 1300 | 32 | 7.2 |
| Example 2 | 300 | 32 | 6.9 |
| Comparative Example 2 | 1000 | 35 | 7.4 |
| Example 3 | 200 | 32 | 7.5 |
| Comparative Example 3 | 800 | 35 | 8.2 |
| Example 4 | 300 | 32 | 7.2 |
| Comparative Example 4 | 900 | 35 | 7.8 |
| Example 5 | 800 | 32 | 7.1 |
| Comparative Example 5 | 2100 | 35 | 7.5 |
| Comparative Example 6 | 1500 | 35 | 7.6 |
| Comparative Example 7 | 100 | 35 | 7.6 |
| Comparative Example 8 | 1200 | 35 | 7.4 |
| Comparative Example 9 | 7700 | 35 | 7.5 |
| Example 6 | 1000 | 40 | 9.0 |
| Comparative Example 10 | 2000 | 40 | 9.6 |

As seen from the results shown in Table 3, it was confirmed that the resist composition of Example 1 which applied the present invention could reduce defects, and also exhibit good lithography properties as compared to the resist composition of Comparative Example 1 which had the same formulation except for the fluorine additive component (F).

It was further confirmed that the resist composition of Example 2 which applied the present invention could reduce defects, and also exhibit good lithography properties as compared to the resist composition of Comparative Example 2 which had the same formulation except for the fluorine additive component (F).

It was further confirmed that the resist composition of Example 3 which applied the present invention could reduce defects, and also exhibit good lithography properties as compared to the resist composition of Comparative Example 3 which had the same formulation except for the fluorine additive component (F).

It was further confirmed that the resist composition of Example 4 which applied the present invention could reduce defects, and also exhibit good lithography properties as compared to the resist composition of Comparative Example 4 which had the same formulation except for the fluorine additive component (F).

It was further confirmed that the resist composition of Example 5 which applied the present invention could reduce defects, and also exhibit good lithography properties as compared to the resist compositions of Comparative Examples 5 to 9 which had the same formulation except for the fluorine additive component (F).

It was further confirmed that the resist composition of Example 6 which applied the present invention could reduce defects, and also exhibit good lithography properties as compared to the resist composition of Comparative Example 10 which had the same formulation except for the fluorine additive component (F).

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition which generates acid upon exposure and exhibits changed solubility in a developing solution under action of acid, the resist composition comprising:
a base component (A) which exhibits changed solubility in a developing solution under action of acid;
an acid generator component (B) which generates acid upon exposure,
a fluorine additive component (F) which exhibits decomposability to an alkali developing solution, and
an organic solvent (S),
wherein the fluorine additive component (F) comprises a fluorine resin component (F1) comprising a structural unit (f1) which comprises a structural unit represented by general formula (f1-1) shown below or a structural unit represented by general formula (f1-2) shown below, and a structural unit (f2) containing a group represented by general formula (f2-r-1) shown below:

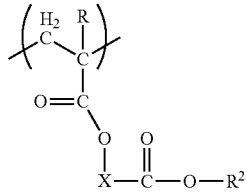

(f1-1)

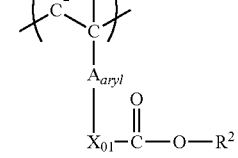

(f1-2)

wherein each R independently represents a hydrogen atom, an alkyl group of 1 to 5 carbon atoms or a halogenated alkyl group of 1 to 5 carbon atoms; X represents a divalent linking group having no acid dissociable portion; $A_{aryl}$ represents a divalent aromatic cyclic group which may have a substituent; $X_{01}$ represents a single bond or a divalent linking group; and each $R^2$ independently represents an organic group having a fluorine atom;

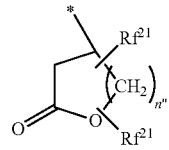

(f2-r-1)

wherein each $Rf^{21}$ independently represents a hydrogen atom, an alkyl group, an alkoxy group, a hydroxy group, a hydroxyalkyl group or a cyano group; n" represents an integer of 0 to 2; and * represents a valence bond.

2. The resist composition according to claim 1, wherein the amount of the fluorine resin component (F1) relative to 100 parts by weight of the base component (A) is within a range from 0.1 to 20 parts by weight.

3. The resist composition according to claim 1, wherein structural unit (f2) is represented by general formula (f2-1) shown below:

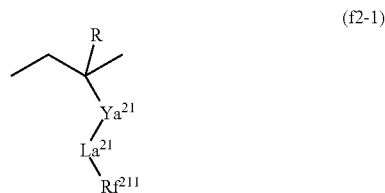

(f2-1)

In the formula, R represents a hydrogen atom, an alkyl group of 1 to 5 carbon atoms or a halogenated alkyl group of 1 to 5 carbon atoms; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group; provided that, when $La^{21}$ represents —O—, $Ya^{21}$ does not represents —CO—; and $Rf^{211}$ is a group represented by general formula (f2-r-1).

4. The resist composition according to claim 2, wherein structural unit (f2) is represented by general formula (f2-1) shown below:

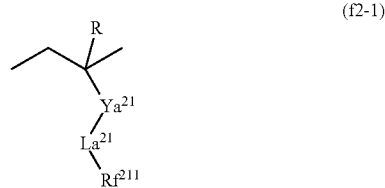

(f2-1)

In the formula, R represents a hydrogen atom, an alkyl group of 1 to 5 carbon atoms or a halogenated alkyl group of 1 to 5 carbon atoms; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group; provided that, when $La^{21}$ represents —O—, $Ya^{21}$ does not represents —CO—; and $Rf^{211}$ is a group represented by general formula (f2-r-1).

5. The resist composition according to claim 1, wherein the base component (A) comprises a resin component (A1) comprising a structural unit (a1) containing an acid decomposable group that exhibits increased polarity by the action of acid, and a structural unit (a10) represented by general formula (a10-1) shown below:

of acid, and a structural unit (a10) represented by general formula (a10-1) shown below:

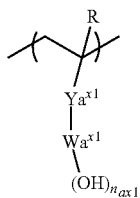

(a10-1)

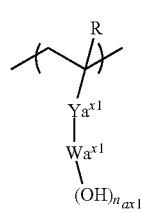

(a10-1)

wherein R represents a hydrogen atom, an alkyl group of 1 to 5 carbon atoms or a halogenated alkyl group of 1 to 5 carbon atoms; $Ya^{x1}$ represents a single bond or a divalent linking group; $Wa^{x1}$ represents an aromatic hydrocarbon group having a valency of $(na_{x1}+1)$, optionally having a substituent; and $na_{x1}$ represents an integer of 1 to 3.

6. The resist composition according to claim 5, wherein the structural unit (a1) is represented by general formula (a1-1-1) shown below:

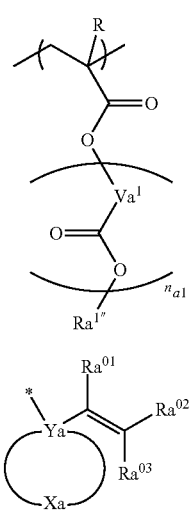

(a1-1-1)

(a1-r2-2)

wherein R represents a hydrogen atom, an alkyl group of 1 to 5 carbon atoms or a halogenated alkyl group of 1 to 5 carbon atoms; $Va^1$ represents a divalent hydrocarbon group optionally having an ether bond; $n_{a1}$ represents an integer of 0 to 2; $Ra^{1\prime\prime\prime}$ is an acid dissociable group represented by general formula (a1-r2-2); Ya represents a carbon atom; Xa represents a group which forms a cyclic hydrocarbon group together with Ya, provided that part or all of the hydrogen atoms of the cyclic hydrocarbon group may be substituted; $Ra^{01}$ to $Ra^{03}$ each independently represents a hydrogen atom, a monovalent saturated chain hydrocarbon group of 1 to 10 carbon atoms or a monovalent saturated aliphatic cyclic hydrocarbon group of 3 to 20 carbon atoms, provided that part or all of the hydrogen atoms of the saturated chain hydrocarbon or the saturated aliphatic cyclic hydrocarbon may be substituted; two or more of $Ra^{01}$ to $Ra^{03}$ may be mutually bonded to form a cyclic structure; and * represents a valence bond.

7. The resist composition according to claim 2, wherein the base component (A) comprises a resin component (A1) comprising a structural unit (a1) containing an acid decomposable group that exhibits increased polarity by the action wherein R represents a hydrogen atom, an alkyl group of 1 to 5 carbon atoms or a halogenated alkyl group of 1 to 5 carbon atoms; $Ya^{a1}$ represents a single bond or a divalent linking group; $Wa^{x1}$ represents an aromatic hydrocarbon group having a valency of $(na_{x1}+1)$, optionally having a substituent; and $na_{x1}$ represents an integer of 1 to 3.

8. The resist composition according to claim 7, wherein the structural unit (a1) is represented by general formula (a1-1-1) shown below:

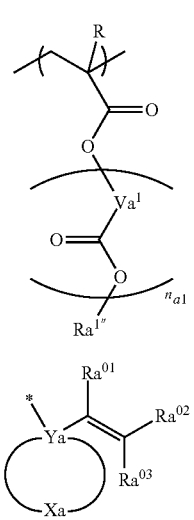

(a1-1-1)

(a1-r2-2)

wherein R represents a hydrogen atom, an alkyl group of 1 to 5 carbon atoms or a halogenated alkyl group of 1 to 5 carbon atoms; $Va^1$ represents a divalent hydrocarbon group optionally having an ether bond; $n_{a1}$ represents an integer of 0 to 2; $Ra^{1\prime\prime\prime}$ is an acid dissociable group represented by general formula (a1-r2-2); Ya represents a carbon atom; Xa represents a group which forms a cyclic hydrocarbon group together with Ya, provided that part or all of the hydrogen atoms of the cyclic hydrocarbon group may be substituted; $Ra^{01}$ to $Ra^{03}$ each independently represents a hydrogen atom, a monovalent saturated chain hydrocarbon group of 1 to 10 carbon atoms or a monovalent saturated aliphatic cyclic hydrocarbon group of 3 to 20 carbon atoms, provided that part or all of the hydrogen atoms of the saturated chain hydrocarbon or the saturated aliphatic cyclic hydrocarbon may be substituted; two or more of $Ra^{01}$ to $Ra^{03}$ may be mutually bonded to form a cyclic structure; and * represents a valence bond.

9. The resist composition according to claim 3, wherein the base component (A) comprises a resin component (A1) comprising a structural unit (a1) containing an acid decomposable group that exhibits increased polarity by the action of acid, and a structural unit (a10) represented by general formula (a10-1) shown below:

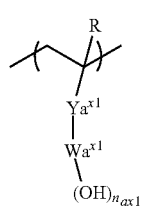

(a10-1)

wherein R represents a hydrogen atom, an alkyl group of 1 to 5 carbon atoms or a halogenated alkyl group of 1 to 5 carbon atoms; $Ya^{x1}$ represents a single bond or a divalent linking group; $Wa^{x1}$ represents an aromatic hydrocarbon group having a valency of $(na_{x1}+1)$, optionally having a substituent; and $na_{x1}$ represents an integer of 1 to 3.

10. The resist composition according to claim 9, wherein the structural unit (a1) is represented by general formula (a1-1-1) shown below:

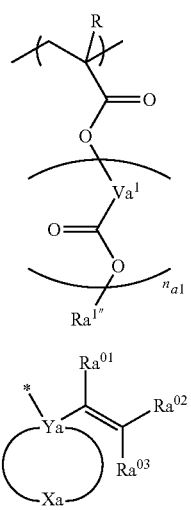

(a1-1-1)

(a1-r2-2)

wherein R represents a hydrogen atom, an alkyl group of 1 to 5 carbon atoms or a halogenated alkyl group of 1 to 5 carbon atoms; $Va^1$ represents a divalent hydrocarbon group optionally having an ether bond; $n_{a1}$ represents an integer of 0 to 2; $Ra^{1'''}$ is an acid dissociable group represented by general formula (a1-r2-2); Ya represents a carbon atom; Xa represents a group which forms a cyclic hydrocarbon group together with Ya, provided that part or all of the hydrogen atoms of the cyclic hydrocarbon group may be substituted; $Ra^{01}$ to $Ra^{03}$ each independently represents a hydrogen atom, a monovalent saturated chain hydrocarbon group of 1 to 10 carbon atoms or a monovalent saturated aliphatic cyclic hydrocarbon group of 3 to 20 carbon atoms, provided that part or all of the hydrogen atoms of the saturated chain hydrocarbon or the saturated aliphatic cyclic hydrocarbon may be substituted; two or more of $Ra^{01}$ to $Ra^{03}$ may be mutually bonded to form a cyclic structure; and * represents a valence bond.

11. The resist composition according to claim 4, wherein the base component (A) comprises a resin component (A1) comprising a structural unit (a1) containing an acid decomposable group that exhibits increased polarity by the action of acid, and a structural unit (a10) represented by general formula (a10-1) shown below:

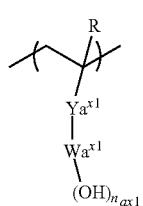

(a10-1)

wherein R represents a hydrogen atom, an alkyl group of 1 to 5 carbon atoms or a halogenated alkyl group of 1 to 5 carbon atoms; $Ya^{x1}$ represents a single bond or a divalent linking group; $Wa^{x1}$ represents an aromatic hydrocarbon group having a valency of $(na_{x1}+1)$, optionally having a substituent; and $na_{x1}$ represents an integer of 1 to 3.

12. The resist composition according to claim 11, wherein the structural unit (a1) is represented by general formula (a1-1-1) shown below:

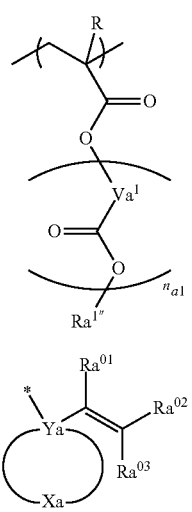

(a1-1-1)

(a1-r2-2)

wherein R represents a hydrogen atom, an alkyl group of 1 to 5 carbon atoms or a halogenated alkyl group of 1 to 5 carbon atoms; $Va^1$ represents a divalent hydrocarbon group optionally having an ether bond; $n_{a1}$ represents an integer of 0 to 2; $Ra^{1'''}$ is an acid dissociable group represented by general formula (a1-r2-2); Ya represents a carbon atom; Xa represents a group which forms a cyclic hydrocarbon group together with Ya, provided that part or all of the hydrogen atoms of the cyclic hydrocarbon group may be substituted; $Ra^{01}$ to $Ra^{03}$ each independently represents a hydrogen atom, a monovalent saturated chain hydrocarbon group of 1 to 10 carbon atoms or a monovalent saturated aliphatic cyclic hydrocarbon group of 3 to 20 carbon atoms, provided that part or all of the hydrogen atoms of the saturated chain hydrocarbon or the saturated aliphatic cyclic hydrocarbon may be substituted; two or more of $Ra^{01}$ to $Ra^{03}$ may be mutually bonded to form a cyclic structure; and * represents a valence bond.

13. A method of forming a resist pattern, comprising:
forming a resist film on a substrate using the resist composition according to claim 1;
exposing the resist film; and
developing the exposed resist film with alkali to form a resist pattern.

14. The method according to claim 13, wherein exposing the resist film is exposed by electron beam or extreme ultraviolet radiation.

15. A resist composition which generates acid upon exposure and exhibits changed solubility in a developing solution under action of acid,
the resist composition comprising:
a base component (A) which exhibits changed solubility in a developing solution under action of acid,
an acid generator component (B) which generates acid upon exposure,
a fluorine additive component (F) which exhibits decomposability to an alkali developing solution, and
an organic solvent (S),
the base component (A) comprises a resin component (A1) comprising a structural unit (a1) represented by general formula (a1-1-1) shown below, and a structural unit (a10) represented by general formula (a10-1) shown below:

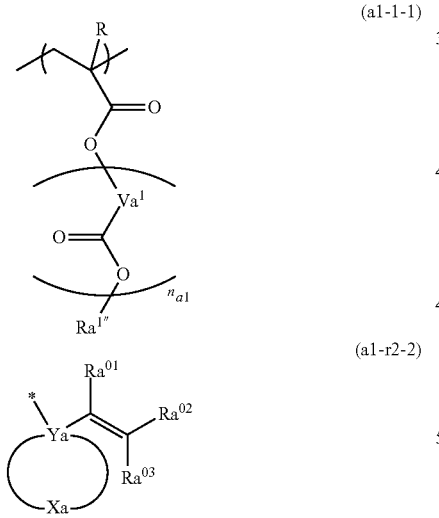

(a1-1-1)

(a1-r2-2)

wherein R represents a hydrogen atom, an alkyl group of 1 to 5 carbon atoms or a halogenated alkyl group of 1 to 5 carbon atoms; $Va^1$ represents a divalent hydrocarbon group optionally having an ether bond; $n_{a1}$ represents an integer of 0 to 2; $Ra^{1\prime\prime\prime}$ is an acid dissociable group represented by general formula (a1-r2-2); Ya represents a carbon atom; Xa represents a group which forms a cyclic hydrocarbon group together with Ya, provided that part or all of the hydrogen atoms of the cyclic hydrocarbon group may be substituted; $Ra^{01}$ to $Ra^{03}$ each independently represents a hydrogen atom, a monovalent saturated chain hydrocarbon group of 1 to 10 carbon atoms or a monovalent saturated aliphatic cyclic hydrocarbon group of 3 to 20 carbon atoms, provided that part or all of the hydrogen atoms of the saturated chain hydrocarbon or the saturated aliphatic cyclic hydrocarbon may be substituted; two or more of $Ra^{01}$ to $Ra^{03}$ may be mutually bonded to form a cyclic structure; and * represents a valence bond;

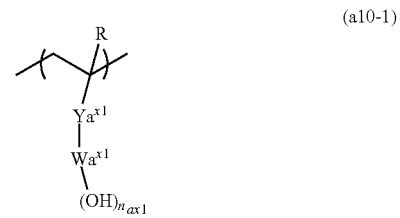

(a10-1)

wherein R represents a hydrogen atom, an alkyl group of 1 to 5 carbon atoms or a halogenated alkyl group of 1 to 5 carbon atoms; $Ya^{x1}$ represents a single bond or a divalent linking group; $Wa^{x1}$ represents an aromatic hydrocarbon group having a valency of $(na_{x1}+1)$, optionally having a substituent; and $na_{x1}$ represents an integer of 1 to 3; and
the fluorine additive component (F) comprising a fluorine resin component (F1) comprising a structural unit (f1) containing a base dissociable group and a structural unit (f2) containing a group represented by general formula (f2-r-1) shown below:

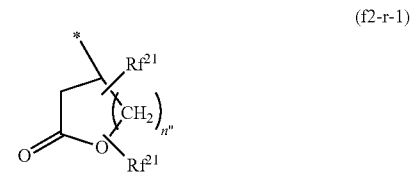

(f2-r-1)

wherein each $Rf^{21}$ independently represents a hydrogen atom, an alkyl group, an alkoxy group, a hydroxy group, a hydroxyalkyl group or a cyano group; n" represents an integer of 0 to 2; and * represents a valence bond.

16. The resist composition according to claim 15, wherein the amount of the fluorine resin component (F1) relative to 100 parts by weight of the base component (A) is within a range from 0.1 to 20 parts by weight.

17. The resist composition according to claim 15, wherein structural unit (f2) is represented by general formula (f2-1) shown below:

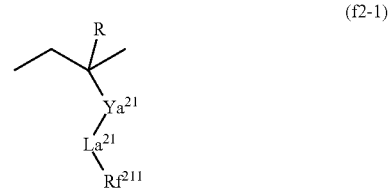

(f2-1)

In the formula, R represents a hydrogen atom, an alkyl group of 1 to 5 carbon atoms or a halogenated alkyl group of 1 to 5 carbon atoms; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group; provided that, when $La^{21}$ represents —O—, $Ya^{21}$ does not represents —CO—; and $Rf^{211}$ is a group represented by general formula (f2-r-1).

* * * * *